(12) United States Patent
Peak et al.

(10) Patent No.: US 8,034,358 B2
(45) Date of Patent: *Oct. 11, 2011

(54) SURFACE ANTIGEN

(75) Inventors: Ian Richard Anselm Peak, St. Lucia (AU); Michael Paul Jennings, Carina (AU); E. Richard Moxon, Oxfordshire (GB)

(73) Assignee: The University of Queesland, St. Lucia (AT)

( * ) Notice: Subject to any disclaimer, the term of this patent is extended or adjusted under 35 U.S.C. 154(b) by 874 days.

This patent is subject to a terminal disclaimer.

(21) Appl. No.: 11/776,709

(22) Filed: Jul. 12, 2007

(65) Prior Publication Data

US 2009/0270591 A1  Oct. 29, 2009

Related U.S. Application Data

(63) Continuation of application No. 10/637,659, filed on Aug. 11, 2003, which is a continuation of application No. 09/797,862, filed on Mar. 5, 2001, now Pat. No. 6,607,729, which is a continuation of application No. 09/377,155, filed on Aug. 19, 1999, now Pat. No. 6,197,312, which is a continuation of application No. PCT/AU98/01031, filed on Dec. 14, 1998.

(30) Foreign Application Priority Data

Dec. 12, 1997 (GB) ................................. 9726398.2

(51) Int. Cl.
*A61K 39/095* (2006.01)
(52) U.S. Cl. ............... 424/250.1; 424/185.1; 424/190.1; 424/234.1; 435/69.1; 435/69.3; 435/71.1; 530/300; 530/350
(58) Field of Classification Search .................. None
See application file for complete search history.

(56) References Cited

U.S. PATENT DOCUMENTS

| 4,702,911 A | 10/1987 | McMichael |
| 4,769,240 A | 9/1988 | Brinton |
| 5,618,541 A | 4/1997 | Quentin-Millet |
| 5,646,259 A | 7/1997 | St. Geme, III |
| 6,197,312 B1 | 3/2001 | Peak |
| 6,495,345 B1 | 12/2002 | Peak |
| 6,607,729 B2 | 8/2003 | Peak |
| 6,709,660 B1 | 3/2004 | Scarlato |
| 6,780,419 B1 | 8/2004 | Ruelle |

FOREIGN PATENT DOCUMENTS

| EP | 0 301 992 | 2/1989 |
| WO | WO 92/03467 | 3/1992 |
| WO | WO 93/06861 | 4/1993 |
| WO | WO 96/29412 | 9/1996 |
| WO | WO 97/26359 | 7/1997 |
| WO | WO 99/31132 | 6/1999 |
| WO | WO 99/58683 | 11/1999 |

OTHER PUBLICATIONS

Stephen J. Barenkamp and Joseph W. St. Geme III, "Identification of a Second Family of High-molecular-Weight Adhesion Proteins Expressed by Non-Typable *Haemophilus Influenzae*," Molecular Microbiology, 1996, 19(6), pp. 1215-1223.
Feng et al., "J. Mol. Evol." 25: 351-380, 1987.
Higgins et al., Cabios Communications 5(2): 151-153, 1989.
Hopp et al., Molecular Immunology 20(4): 483-489, 1983.
Kolaskar et al., FEBS 276(1,2): 172-174, 1990.
Welling et al., FEBS 188(2): 215-218, 1985.
Sacchi et al., "Considerations on the Use of *Neisseria meningitidis* Class 5 Proteins as Meningococcal BC Vaccine Components," *Vaccine*, 1995, vol. 13, No. 1, pp. 112-118, Elsevier Science Ltd.
Rudinger et al., in "Peptide Hormones," edited by Parsons, J.A., University Park Press, Jun. 1976, p. 6.
Burgess et al., The Journal of Cell Biology, 111:2129-2138, 1990.
Lazar et al., Molecular and Cellular Biology, 8(3):1247-1252, 1988.
Jobling et al., Mol. Microbiol. 1991, 5(7): 1755-67.
St. Geme et al., Characterization of the Genetic Locus Encoding Haemophilus Influence Type B Surface Fibrils, J. Bacteriol., Nov. 1996, pp. 6281-6287, vol. 178, No. 21.

*Primary Examiner* — Jennifer Graser
(74) *Attorney, Agent, or Firm* — Perkins Coie LLP

(57) ABSTRACT

The invention provides a novel surface polypeptide from *Neisseria meningitidis* as well as nucleic acid and nucleic acid sequence homologues encoding this protein. Pharmaceutical compositions containing the polypeptide and nucleic acids of the invention are also disclosed as well as methods useful in the treatment, prevention and diagnosis of *N. meningitidis* infection.

9 Claims, 15 Drawing Sheets

FIG. 6

```
            1                                                    50
    Hsf   MNKIFNVIWN VMTQTWVVVS ELTRTHTKRA SATVETAVLA TLLFATVQAN
    Hia   MNKIFNVIWN VVTQTWVVVS ELTRTHTKCA SATVAVAVLA TLLSATVEAN
    HiaNm MNKIYRIIWN SALNAWVVVS ELTRNHTKRA SATVKTAVLA TLLFATVQAS 51                                                   100
    Hsf   ATDEDEELDP VVRTAPVLSF HSDKEGTGEK EVTENSNWGI YFDNKGVLKA
    Hia   .......... .......... .......... .......... ..........
    HiaNm A......... .......... .......... .......... ..........

101                                                  150
    Hsf   GAITLKAGDN LKIKQNTDES TNASSFTYSL KKDLTDLTSV ATEKLSFGAN
    Hia   .......... .......... .......... .......... ..........
    HiaNm .......... .......... .......... .......... ..........

151                                                  200
    Hsf   GDKVDITSDA NGLKLAKTGN GNVHLNGLDS TLPDAVTNTG VLSSSSFTPN
    Hia   .......... .......... .......... ......NNTP V.........
    HiaNm .......... .......... .......... .......... ..........

201                                                  250
    Hsf   DVEKTRAATV KDVLNAGWNI KGAKTAGGNV ESVDLVSAYN NVEFITGDKN
    Hia   .......... .......... .......... .......... ..........
    HiaNm .......... .......... .......... .......... ..........

251                                                  300
    Hsf   TLDVVLTAKE NGKTTEVKFT PKTSVIKEKD GKLFTGKENN DTNKVTSNTA
    Hia   .......... .......... .......... .......... .TNK......
    HiaNm .......... .......... .......... .......... ..........

301                                                  350
    Hsf   TDNTDEGNGL VTAKAVIDAV NKAGWRVKTT TANGQNGDFA TVASGTNVTF
    Hia   .......... .......... .......... .......... ..........
    HiaNm .......... .......... .......... .......... ..........

351                                                  400
    Hsf   ESGDGTTASV TKDTNGNGIT VKYDAKVGDG LKFDSDKKIV ADTTALTVTG
    Hia   .......... .......... .......... .......... ..........
    HiaNm .......... .......... .......... .......... ..........

401                                                  450
    Hsf   GKVAEIAKED DKKKLVNAGD LVTALGNLSW KAKAEADTDG ALEGISKDQE
    Hia   .......... .......... .......... .......... ..........
    HiaNm .......... .......... .......... .......... ..........

451                                                  500
    Hsf   VKAGETVTFK AGKNLKVKQD GANFTYSLQD ALTGLTSITL GGTTNGGNDA
    Hia   .......... .......... .......... .......... ..........
    HiaNm .......... .......... .......... .......... ..........

501                                                  550
    Hsf   KTVINKDGLT ITPAGNGGTT GTNTISVTKD GIKAGNKAIT NVASGLRAYD
    Hia   .......... .......... .......... .......... ......LKAYG
    HiaNm .......... .......... .......... .......... ..........
```

FIG. 6 cont'd

```
            551                                                         600
    Hsf     DANFDVLNNS  ATDLNRHVED  AYKGLLNLNE  KNANKQPLVT  DSTAATVGDL
    Hia     DANFNFTNNS  IADAEKQVQE  AYKGLLNLNE  KNASDKLLVE  DNTAATVGNL
    HiaNm   ..........  ..........  ........NN  ERPRKKDLYL  DPVQRTVAVL 601                                                         650
    Hsf     RKLGWVVSTK  NGTKEE.SNQ  VKQAD.EVLF  TGAGAATVTS  KSENGKHTIT
    Hia     RKLGWVLSSK  NGTRNEKSQQ  VKHAD.EVLF  EGKGGVQVTS  TSENGKHT..
    HiaNm   I....VNSDK  EGT.GEKEKV  EENSDWAVYF  NEKGVLT...  ..........

651                                                         700
    Hsf     VSVAETKADC  GLEKDGDTIK  LKVDNQNTDN  VLTVGNNGTA  VTKGGFETVK
    Hia     ..........  ..........  ..........  ..........  ..........
    HiaNm   ..........  ..........  ..........  ..........  ..........

701                                                         750
    Hsf     TGATDADRGK  VTVKDATAND  ADKKVATVKD  VATAINSAAT  FVKTENLTTS
    Hia     ..........  ..........  ..........  ..........  ..........
    HiaNm   ..........  ..........  ..........  ..........  ..........

751                                                         800
    Hsf     IDEDNPTDNG  KDDALKAGDT  LTFKAGKNLK  VKRDGKNITF  DLAKNLEVKT
    Hia     ..........  ..........  ..........  .......ITF  ALAKDLGVKT
    HiaNm   ..........  .......ARE  ITLKAGDNLK  IKQNGTNFTY  SLKKDLTDLT 801                                                         850
    Hsf     AKVSDTLTIG  GNTPTGGTTA  TPKVNITSTA  DGLNFAKETA  DASGSKNVYL
    Hia     ATVSDTLTIG  GGAAAGATT.  TPKVNVTSTT  DGLKFAKDAA  GANG......
    HiaNm   SVGTEKLSFS  ANGN......  ..KVNITSDT  KGLNFAKETA  GTNG......

851                                                         900
    Hsf     KGIATTLTEP  SAGAKSSHVD  LNVDATKKSN  AASIEDVLRA  GWNIQGNGNN
    Hia     ..........  ..........  ..........  ..........  ..........
    HiaNm   ..........  ..........  ..........  ..........  ..........

901                                                         950
    Hsf     VDYVATYDTV  NFTDDSTGTT  TVTVTQKADG  KGADVKIGAK  TSVIKDHNGK
    Hia     ..........  ..........  ..........  ..........  ..........
    HiaNm   ..........  ..........  ..........  ..........  ..........

951                                                        1000
    Hsf     LFTGKDLKDA  NNGATVSEDD  GKDTGTGLVT  AKTVIDAVNK  SGWRVTGEGA
    Hia     ..........  ..........  ..........  ..........  ..........
    HiaNm   ..........  ..........  ..........  ..........  ..........

1001                                                       1050
    Hsf     TAETGATAVN  AGNAETVTSG  TSVNFKNGNA  TTATVSKDNG  NINVKYDVNV
    Hia     ..........  ..........  ..........  ..........  ..........
    HiaNm   ..........  ..........  ..........  ..........  ..........

1051                                                       1100
    Hsf     GDGLKIGDDK  KIVADTTTLT  VTGGKVSVPA  GANSVNNKK   LVNAEGLATA
    Hia     ..........  ....DTT...  ..........  ..........  ..........
    HiaNm   ..........  ....DTT...  ..........  ..........  ..........
```

FIG. 6 cont'd

```
       1101                                                     1150
Hsf    LNNLSWTAKA DKYADGESEG ETDQEVKAGD KVTFKAGKNL KVKQSEKDFT
Hia    .......... .......... .......... .......... ..........
HiaNm  .......... .......... .......... .......... ..........

1151                                                     1200
Hsf    YSLQDTLTGL TSITLGGTAN GRNDTGTVIN KDGLTITLAN GAAAGTDASN
Hia    .......... .......... .......... .......... ..........
HiaNm  .......... .......... .......... .......... ..........

1201                                                     1250
Hsf    GNTISVTKDG ISAGNKEITN VKSALKTYKD TQNTADETQD KEFHAAVKNA
Hia    .......... .......... .......... .......... ..........
HiaNm  .......... .......... .......... .......... ..........

1251                                                     1300
Hsf    NEVEFVGKNG ATVSAKTDNN GKHTVTIDVA EAKVGDGLEK DTDGKIKLKV
Hia    .......... .......... .......... .......... ..........
HiaNm  .......... .......... .......... .......... ..........

1301                                                     1350
Hsf    DNTDGNNLLT VDATKGASVA KGEFNAVTTD ATTAQGTNAN ERGKVVVKGS
Hia    .......... .......... .......... .......... ..........
HiaNm  .......... .......... .......... .......... ..........

1351                                                     1400
Hsf    NGATATETDK KKVATVGDVA KAINDAATFV KVENDDSATI DDSPTDDGAN
Hia    .......... .......... .......... .......... ..........
HiaNm  .......... .......... .......... .......... ..........

1401                                                     1450
Hsf    DALKAGDTLT LKAGKNLKVK RDGKNITFAL ANDLSVKSAT VSDKLSLGTN
Hia    .......... .......... .......... .......... ..........
HiaNm  .......... .......... .......... .......... ..........

1451                                                     1500
Hsf    GNKVNITSDT KGLNFAKDSK TGDDANIHLN GIASTLTDTL LNSGATTNLG
Hia    .......... .......... ......VHLN GIGSTETDTL VGSPATHIDG
HiaNm  .......... .......... ......VHLN GIGSTLTDTL LNTGATTNVT 1501                                                     1550
Hsf    GNGITDNEKK RAASVKDVLN AGWNVRGVKP ASANNQVENI DFVATYDTVD
Hia    GDQSTHY..T RAASIKDVLN AGWNIKGVKA GSTTGQSENV DFVHTYDTVE
HiaNm  NDNVTDDEKK RAASVKDVLN AGWNIKGVKP GTTA...SDNV DFVRTYDTVE 1551                                                     1600
Hsf    FVSGDKDTTS VTVESKDNGK RTEVKIGAKT SVIKDHNGKL FTGKELKDAN
Hia    FLSADTETTT VTVDSKENGK RTEVKIGAKT SVIKEKDGKL FTGKANKETN
HiaNm  FLSADTKTTT VNVESKDNGK KTEVKIGVKT SVIKEKDGKL VTGKD.KGEN 1601                                                     1650
Hsf    NNGVTVTETD GKDEGNGLVT AKAVIDAVNK AGWRVKTTGA NGQNDD...F
Hia    KVD.GANATE DADEGKGLVT AKDVIDAVNK TGWRIKTTDA NGQNGD...F
HiaNm  ........GS STDEGEGLVT AKEVIDAVNK AGWRMKTTTA NGQTGQADKF
```

FIG. 6 cont'd

```
          1651                                                    1700
   Hsf    ATVASGTNVT FADGNGTTAE VTKANDGSIT VKYNVKVADG LKLDGDKIVA
   Hia    ATVASGTNVT FASGNGTTAT VTNGTDG.IT VKYDAKVGDG LKLDGDKIAA
   HiaNm  ETVTSGTNVT FASGKGTTAT VSKDDQGNIT VMYDVNVGDA LNVNQ.....

1701                                                    1750
   Hsf    DTTVLTVAD. .......GKV TAPNNGDGKK FVDASGLADA LNKLSWTATA
   Hia    DTTALTVNDG KNANNPKGKV ADVASTDEKK LVTAKGLVTA LNSLSWTTTA
   HiaNm  .......... .......... .......... .LQNSGW... ..NLDSKAVA 1751                                                    1800
   Hsf    GKEGTGEVDP ANSAGQEVKA GDKVTFKAGD NLKIKQSGKD FTYSLKKELK
   Hia    AEADGGTLD. GNASEQEVKA GDKVTFKAGK NLKVKQEGAN FTYSLQDALT
   HiaNm  G..SSGKVIS GNVSPSKGKM DETVNINAGN NIEITRNGKN I..DIATSMT 1801                                                    1850
   Hsf    .DLTSVEFKD ANGGTGSEST KITKDGLTIT PANGAGAAGA NTANTISVTK
   Hia    .GLTSITLGT GNNGA...KT EINKDGLTIT PANG...AGA NNANTISVTK
   HiaNm  PQFSSVSLG. .......... .......... .......AGA D.APTLSV..

1851                                                    1900
   Hsf    DGISAGNKAV TNVVSGLKKF GDGHTLANGT VAD.FEKHYD NAYKDLTNLD
   Hia    DGISAGGQSV KNVVSGLKKF GDANFDPLTS SADNLTKQND DAYKGLTNLD
   HiaNm  .......... .......... .......... .......... ..........

1901                                                    1950
   Hsf    EKGADNN.PT VADNTAATVG DLRGLGWVIS ADKTTGEPNQ EYNAQVRNAN
   Hia    EKGTDKQTPV VADNTAATVG DLRGLGWVIS ADKTTGGST. EYHDQVRNAN
   HiaNm  .......... .......... .......... .......... ..........

1951                                                    2000
   Hsf    EVKFKSGNGI NVSGKTLNGT RVITFELAKG EVVKSNEFTV KNADGSETNL
   Hia    EVKFKSGNGI NVSGKTVNGR REITFELAKG EVVKSNEFTV KETNGKETSL
   HiaNm  .....DGDAL NVGSK..... .......... .......... ..........

2001                                                    2050
   Hsf    VKVGDMYYSK EDIDPATSKP ..MTGKT..E KYKVENGKVV SANGSKTEVT
   Hia    VKVGDKYYSK EDIDLTTGQP KLKDGNTVAA KYQDKGGKVV SVTD.NTEAT
   HiaNm  .......... .......... .......... ....KDNKPV R.........

2051                                                    2100
   Hsf    LTNKGSGYVT GNQVADAIAK SGFELGLADA AEAEKAFAES AKDKQLSKDK
   Hia    ITNKGSGYVT GNQVADAIAK SGFELGLADE ADAKRAFDD. .KTKALSAGT
   HiaNm  ITNVAPG... .......... .......... .......... ..........

2101                                                    2150
   Hsf    AETVNAHDKV RFANGLNTKV SAATVESTDA NGDKVTTTFV KTDVELPLTQ
   Hia    TEIVNAHDKV RFANGLNTKV SAATVESTDA NGDKVTTTFV KTDVELPLTQ
   HiaNm  .......... .......... .......... .......... ..........

2151                                                    2200
   Hsf    IYNTDANGNK I...VKKADG KWYELNADGT AS.NKEVTLG NVDANGKKVV
   Hia    IYNTDANGKK ITKVVKDGQT KWYELNADGT ADMTKEVTLG NVDSDGKKVV
   HiaNm  .......... ....VKEGD. .......... .......... ..........
```

FIG. 6 cont'd

```
              2201                                                      2250
    Hsf   KVTENGADKW  YYTNADGAAD  KTKGEVSNDK  VSTDEKHVVR  LDPNNQSNGK
    Hia   K...DNDGKW  YHAKADGTAD  KTKGEVSNDK  VSTDEKHVVS  LDPNDQSKGK
  HiaNm   ..........  ..........  ..........  ..........  ..........

2251                                                      2300
    Hsf   GVVIDNVANG  EISATSTDAI  NGSQLYAVAK  GVTNLAGQVN  NLEGKVNKVG
    Hia   GVVIDNVANG  DISATSTDAI  NGSQLYAVAK  GVTNLAGQVN  NLEGKVNKVG
  HiaNm   ...VTNVA..  ..........  ...QLKGVA.  .........Q  NLNNRIDNVD 2301                                                      2350
    Hsf   KRADAGTASA  LAASQLPQAT  MPGKSMVAIA  GSSYQGQNGL  AIGVSRISDN
    Hia   KRADAGTASA  LAASQLPQAT  MPGKSMVAIA  GSSYQGQNGL  AIGVSRISDN
  HiaNm   GNARAGIAQA  IATAGLVQAY  LPGKSMMAIG  GGTYRGEAGY  AIGYSSISDG 2351                        2378
    Hsf   GKVIIRLSGT  TNSQGKTGVA  AGVGYQW*
    Hia   GKVIIRLSGT  TNSQGKTGVA  AGVGYQW*
  HiaNm   GNWIIKGTAS  GNSRGHFGAS  ASVGYQW*
```

FIG. 7

```
              1                                                                          50
   eg329   MNEILRIIWN   SALNAWVVVS   ELTRNHTKRA   SATVKTAVLA   TLLFATVQAS
   pmc21   MNKIYRIIWN   SALNAWVVVS   ELTRNHTKRA   SATVKTAVLA   TLLFATVQAS
   HiaNm   MNKIYRIIWN   SALNAWVVVS   ELTRNHTKRA   SATVKTAVLA   TLLFATVQAS
     h15   MNKIYRIIWN   SALNAWVVVS   ELTRNHTKRA   SATVATAVLA   TLLFATVQAN
    BZ10   MNKISRIIWN   SALNAWVVVS   ELTRNHTKRA   SATVATAVLA   TLLFATVQAN
   bz198   MNKIYRIIWN   SALNAWVVVS   ELTRNHTKRA   SATVATAVLA   TLLFATVQAN
   eg327   MNKIYRIIWN   SALNAWVAVS   ELTRNHTKRA   SATVATAVLA   TLLFATVQAS
     h38   MNKIYRIIWN   SALNAWVAVS   ELTRNHTKRA   SATVKTAVLA   TLLFATVQAN
     h41   MNKIYRIIWN   SALNAWVAVS   ELTRNHTKRA   SATVKTAVLA   TLLFATVQAN
     p20   MNKIYRIIWN   SALNAWVVVS   ELTRNHTKRA   SATVATAVLA   TLLSATVQAN 51                                                                        100
   eg329   ANNE.EQEED   LYLDPVLRTV   AVLIVNSDKE   GTGEKEKVEE   NSDWAVYFNE
   pmc21   ANNE.EQEED   LYLDPVQRTV   AVLIVNSDKE   GTGEKEKVEE   NSDWAVYFNE
   HiaNm   ANNERPRKKD   LYLDPVQRTV   AVLIVNSDKE   GTGEKEKVEE   NSDWAVYFNE
     h15   ATD....DDD   LYLEPVQRTA   VVLSFRSDKE   GTGEKE.GTE   DSNWAVYFDE
    BZ10   ATD....DDD   LYLEPVQRTA   VVLSFRSDKE   GTGEKE.GTE   DSNWAVYFDE
   bz198   ATD....DDD   LYLEPVQRTA   VVLSFRSDKE   GTGEKE.GTE   DSNWAVYFDE
   eg327   TTD....DDD   LYLEPVQRTA   VVLSFRSDKE   GTGEKE.VTE   DSNWGVYFDK
     h38   ATDE...DEE   EELEPVVRSA   LVLQFMIDKE   GNGENE.STG   NIGWSIYYDN
     h41   ATDE...DEE   EELESVQRS.   VVGSIQASME   GSVELETI..   ...SLSMTNDS
     p20   ATDT...DED   EELESVARSA   LVLQFMIDKE   GNGEIE.STG   DIGWSIYYDD 101                                                                       150
   eg329   KGVLTA.REI   TLKAGDNLKI   KQ........   ..NGTNFTYS   LKKDLTDLTS
   pmc21   KGVLTA.REI   TLKAGDNLKI   KQ........   ..NGTNFTYS   LKKDLTDLTS
   HiaNm   KGVLTA.REI   TLKAGDNLKI   KQ........   ..NGTNFTYS   LKKDLTDLTS
     h15   KRVLKA.GAI   TLKAGDNLKI   KQNTNENTNE   NTNDSSFTYS   LKKDLTDLTS
    BZ10   KRVLKA.GAI   TLKAGDNLKI   KQNTNENTNE   NTNDSSFTYS   LKKDLTDLTS
   bz198   KRVLKA.GAI   TLKAGDNLKI   KQ....NTNE   NTNDSSFTYS   LKKDLTDLTS
   eg327   KGVLTA.GTI   TLKAGDNLKI   KQ....NTNE   NTNASSFTYS   LKKDLTDLTS
     h38   HNTLHG.ATV   TLKAGDNLKI   KQNTNKNTNE   NTNDSSFTYS   LKKDLTDLTS
     h41   KEFVDPYIVV   TLKAGDNLKI   KQ....NTNE   NTNASSFTYS   LKKDLTGLIN
     p20   HNTLHG.ATV   TLKAGDNLKI   KQ........   ..SGKDFTYS   LKKELKDLTS 151                                                                       200
   eg329   VGTEKLSFSA   NGNKVNITSD   TKGLNFAKET   AGTNGDTTVH   LNGIGSTLTD
   pmc21   VGTEKLSFSA   NGNKVNITSD   TKGLNFAKET   AGTNGDTTVH   LNGIGSTLTD
   HiaNm   VGTEKLSFSA   NGNKVNITSD   TKGLNFAKET   AGTNGDTTVH   LNGIGSTLTD
     h15   VETEKLSFGA   NGNKVNITSD   TKGLNFAKET   AGTNGDPTVH   LNGIGSTLTD
    BZ10   VETEKLSFGA   NGNKVNITSD   TKGLNFAKET   AGTNGDPTVH   LNGIGSTLTD
   bz198   VETEKLSFGA   NGNKVNITSD   TKGLNFAKET   AGTNGDPTVH   LNGIGSTLTD
   eg327   VGTEKLSFSA   NSNKVNITSD   TKGLNFAKKT   AETNGDTTVH   LNGIGSTLTD
     h38   VETEKLSFGA   NGNKVNITSD   TKGLNFAKET   AGTNGDTTVH   LNGIGSTLTD
     h41   VETEKLSFGA   NGKKVNIISD   TKGLNFAKET   AGTNGDTTVH   LNGIGSTLTD
     p20   VETEKLSFGA   NGNKVNITSD   TKGLNFAKET   AGTNGDPTVH   LNGIGSTLTD
```

FIG. 7 cont'd

```
        201                                                       250
eg329   TLLNTGATTN VTNDNVTDDE KKRAASVKDV LNAGWNIKGV KPGTTA..SD
pmc21   TLLNTGATTN VTNDNVTDDE KKRAASVKDV LNAGWNIKGV KPGTTA..SD
HiaNm   TLLNTGATTN VTNDNVTDDE KKRAASVKDV LNAGWNIKGV KPGTTA..SD
  h15   TLLNTGATTN VTNDNVTDDE KKRAASVKDV LNAGWNIKGV KPGTTA..SD
 BZ10   TLLNTGATTN VTNDNVTDDE KKRAASVKDV LNAGWNIKGV KPGTTA..SD
 bz198  TLLNTGATTN VTNDNVTDDE KKRAASVKDV LNAGWNIKGV KPGTTA..SD
 eg327  TLLNTGATTN VTNDNVTDDE KKRAASVKDV LNAGWNIKGV KPGTTA..SD
  h38   TLLNTGATTN VTNDNVTDDK KKRAASVKDV LNAGWNIKGV KPGTTA..SD
  h41   MLLNTGATTN VTNDNVTDDE KKRAASVKDV LNAGWNIKGV KPGTTA..SD
  p20   TLAGSSASHV DAGNQSTHY. .TRAASIKDV LNAGWNIKGV KTGSTTGQSE 251                                                       300
eg329   NVDFVRTYDT VEFLSADTKT TTVNVESKDN GKKTEVKIGA KTSVIKEKDG
pmc21   NVDFVRTYDT VEFLSADTKT TTVNVESKDN GKKTEVKIGA KTSVIKEKDG
HiaNm   NVDFVRTYDT VEFLSADTKT TTVNVESKDN GKKTEVKIGV KTSVIKEKDG
  h15   NVDFVRTYDT VEFLSADTKT TTVNVESKDN GKKTEVKIGA KTSVIKEKDG
 BZ10   NVDFVRTYDT VEFLSADTKT TTVNVESKDN GKRTEVKIGA KTSVIKEKDG
 bz198  NVDFVRTYDT VEFLSADTKT TTVNVESKDN GKKTEVKIGA KTSVIKEKDG
 eg327  NVDFVRTYDT VEFLSADTKT TTVNVESKDN GKRTEVKIGA KTSVIKEKDG
  h38   NVDFVHTYDT VEFLSADTKT TTVNVESKDN GKRTEVKIGA KTSVIKEKDG
  h41   NVDFVRTYDT VEFLSADTKT TTVNVESKDN GKKTEVKIGA KTSVIKEKDG
  p20   NVDFVRTYDT VEFLSADTKT TTVNVESKDN GKRTEVKIGA KTSVIKEKDG 301                                                       350
eg329   KLVTGKDKGE NGSSTDEGEG LVTAKEVIDA VNKAGWRMKT TTANGQTGQA
pmc21   KLVTGKDKGE NGSSTDEGEG LVTAKEVIDA VNKAGWRMKT TTANGQTGQA
HiaNm   KLVTGKDKGE NGSSTDEGEG LVTAKEVIDA VNKAGWRMKT TTANGQTGQA
  h15   KLVTGKGKDE NGSSTDEGEG LVTAKEVIDA VNKAGWRMKT TTANGQTGQA
 BZ10   KLVTGKGKGE NGSSTDEGEG LVTAKEVIDA VNKAGWRMKT TTANGQTGQA
 bz198  KLVTGKGKDE NGSSTDEGEG LVTAKEVIDA VNKAGWRMKT TTANGQTGQA
 eg327  KLVTGKDKGE NDSSTDKGEG LVTAKEVIDA VNKAGWRMKT TTANGQTGQA
  h38   KLVTGKGKGE NGSSTDEGEG LVTAKEVIDA VNKAGWRMKT TTANGQTGQA
  h41   KLVTGKGKGE NGSSTDEGEG LVTAKEVIDA VNKAGWRMKT TTANGQTGQA
  p20   KLVTGKGKGE NGSSTDEGEG LVTAKEVIDA VNKAGWRMKT TTANGQTGQA 351                                                       400
eg329   DKFETVTSGT NVTFASGKGT TATVSKDDQG NITVMYDVNV GDALNVNQLQ
pmc21   DKFETVTSGT NVTFASGKGT TATVSKDDQG NITVMYDVNV GDALNVNQLQ
HiaNm   DKFETVTSGT NVTFASGKGT TATVSKDDQG NITVMYDVNV GDALNVNQLQ
  h15   DKFETVTSGT KVTFASGNGT TATVSKDDQG NITVKYDVNV GDALNVNQLQ
 BZ10   DKFETVTSGT KVTFASGNGT TATVSKDDQG NITVKYDVNV GDALNVNQLQ
 bz198  DKFETVTSGT NVTFASGKGT TATVSKDDQG NITVKYDVNV GDALNVNQLQ
 eg327  DKFETVTSGT NVTFASGKGT TATVSKDDQG NITVMYDVNV GDALNVNQLQ
  h38   DKFETVTSGT NVTFASGKGT TATVSKDDQG NITVKYDVNV GDALNVNQLQ
  h41   DKFETVTSGT KVTFASGNGT TATVSKDDQG NITVKYDVNV GDALNVNQLQ
  p20   DKFETVTSGT KVTFASGNGT TATVSKDDQG NITVKYDVNV GDALNVNQLQ
```

FIG. 7 cont'd

```
        401                                                        450
eg329   NSGWNLDSKA VAGSSGKVIS GNVSPSKGKM DETVNINAGN NIEITRNGKN
pmc21   NSGWNLDSKA VAGSSGKVIS GNVSPSKGKM DETVNINAGN NIEITRNGKN
HiaNm   NSGWNLDSKA VAGSSGKVIS GNVSPSKGKM DETVNINAGN NIEITRNGKN
  h15   NSGWNLDSKA VAGSSGKVIS GNVSPSKGKM DETVNINAGN NIEITRNGKN
 BZ10   NSGWNLDSKA VAGSSGKVIS GNVSPSKGKM DETVNINAGN NIEITRNGKN
 bz198  NSGWNLDSKA VAGSSGKVIS GNVSPSKGKM DETVNINAGN NIEITRNGKN
 eg327  NSGWNLDSKA VAGSSGKVIS GNVSPSKGKM DETVNINAGN NIEITRNGKN
  h38   NSGWNLDSKA VAGSSGKVIS GNVSPSKGKM DETVNINAGN NIEITRNGKN
  h41   NSGWNLDSKA VAGSSGKVIS GNVSPSKGKM DETVNINAGN NIEITRNGKN
  p20   NSGWNLDSKA VAGSSGKVIS GNVSPSKGKM DETVNINAGN NIEITRNGKN 451                                                        500
eg329   IDIATSMTPQ FSSVSLGAGA DAPTLSVDGD .ALNVGSKKD NKPVRITNVA
pmc21   IDIATSMTPQ FSSVSLGAGA DAPTLSVDGD .ALNVGSKKD NKPVRITNVA
HiaNm   IDIATSMTPQ FSSVSLGAGA DAPTLSVDGD .ALNVGSKKD NKPVRITNVA
  h15   IDIATSMTPQ FSSVSLGAGA DAPTLSVDDE GALNVGSKDA NKPVRITNVA
 BZ10   IDIATSMTPQ FSSVSLGAGA DAPTLSVDDE GALNVGSKDA NKPVRITNVA
 bz198  IDIATSMAPQ FSSVSLGAGA DAPTLSVDDE GALNVGSKDT NKPVRITNVA
 eg327  IDIATSMTPQ FSSVSLGAGA DAPTLSVDDE GALNVGSKDA NKPVRITNVA
  h38   IDIATSMTPQ FSSVSLGAGA DAPTLSVDDK GALNVGSKDA NKPVRITNVA
  h41   IDIATSMTPQ FSSVSLGAGA DAPTLSVDDE GALNVGSKDA NKPVRITNVA
  p20   IDIATSMTPQ FSSVSLGAGA DAPTLSVDDE GALNVGSKDA NKPVRITNVA 501                                                        550
eg329   PGVKEGDVTN VAQLKGVAQN LNNRIDNVDG NARAGIAQAI ATAGLVQAYL
pmc21   PGVKEGDVTN VAQLKGVAQN LNNRIDNVDG NARAGIAQAI ATAGLVQAYL
HiaNm   PGVKEGDVTN VAQLKGVAQN LNNRIDNVDG NARAGIAQAI ATAGLVQAYL
  h15   PGVKEGDVTN VAQLKGVAQN LNNRIDNVDG NARAGIAQAI ATAGLAQAYL
 BZ10   PGVKEGDVTN VAQLKGVAQN LNNRIDNVDG NARAGIAQAI ATAGLAQAYL
 bz198  PGVKEGDVTN VAQLKGVAQN LNNRIDNVDG NARAGIAQAI ATAGLVQAYL
 eg327  PGVKEGDVTN VAQLKGVAQN LNNHIDNVDG NARAGIAQAI ATAGLVQAYL
  h38   PGVKEGDVTN VAQLKGVAQN LNNRIDNVDG NARAGIAQAI ATAGLVQAYL
  h41   PGVKEGDVTN VAQLKGVAQN LNNRIDNVNG NARAGIAQAI ATAGLVQAYL
  p20   PGVKEGDVTN VAQLKGVAQN LNNRIDNVNG NARAGIAQAI ATAGLAQAYL 551                                                        600
eg329   PGKSMMAIGG GTYRGEAGYA IGYSSISDGG NWIIKGTASG NSRGHFGASA
pmc21   PGKSMMAIGG GTYRGEAGYA IGYSSISDGG NWIIKGTASG NSRGHFGASA
HiaNm   PGKSMMAIGG GTYRGEAGYA IGYSSISDGG NWIIKGTASG NSRGHFGASA
  h15   PGKSMMAIGG GTYRGEAGYA IGYSSISDTG NWVIKGTASG NSRGHFGASA
 BZ10   PGKSMMAIGG GTYRGEAGYA IGYSSISDTG NWVIKGTASG NSRGHFGTSA
 bz198  PGKSMMAIGG DTYRGEAGYA IGYSSISDGG NWIIKGTASG NSRGHFGASA
 eg327  PGKSMMAIGG GTYRGEAGYA IGYSSISDGG NWIIKGTASG NSRGHFGASA
  h38   PGKSMMAIGG GTYRGEAGYA IGYSSISDGG NWIIKGTASG NSRGHFGASA
  h41   PGKSMMAIGG GTYLGEAGYA IGYSSISAGG NWIIKGTASG NSRGHFGASA
  p20   PGKSMMAIGG GTYLGEAGYA IGYSSISDTG NWVIKGTASG NSRGHFGTSA
```

FIG. 7 cont'd

```
         601
eg329    SVGYQW*
pmc21    SVGYQW*
HiaNm    SVGYQW*
  h15    SVGYQW*
 BZ10    SVGYQW*
bz198    SVGYQW*
eg327    SVGYQW*
  h38    SVGYQW*
  h41    SVGYQW*
  p20    SVGYQW*
```

SURFACE ANTIGEN

The application is a continuation of U.S. application Ser. No. 10/637,659, filed Aug. 11, 2003, which is a continuation of U.S. application Ser. No. 09/797,862, filed Mar. 5, 2001, now U.S. Pat. No. 6,607,729, which is a continuation of U.S. Ser. No. 09/377,155, filed Aug. 19, 1999, now U.S. Pat. No. 6,197,312, which is a continuation of PCT/AU98/01031, filed Dec. 14, 1998; the entireties of which are hereby incorporated by reference.

FIELD OF THE INVENTION

The present invention relates to novel polypeptides as for example obtainable from *Neisseria meningitidis*, to nucleotide sequences encoding such polypeptides, to the use of these in diagnostics, in therapeutic and prophylactic vaccines and in the design and/or screening of medicaments.

BACKGROUND OF THE INVENTION

*Neisseria meningitidis* is a Gram-negative bacterium and the causative agent of meningococcal meningitis and septicemia. Its only known host is the human, and it may be carried asymptomatically by approximately 10% of the population (Caugant, D. et al, 1994, *Journal of Clinical Microbiology*, 32:323-30).

*N. meningitides* may express a polysaccharide capsule, and this allows classification of the bacteria according to the nature of the capsule expressed. There are at least thirteen serogroups of *N. meningitidis*: A, B, C, 29-E, H, I, K, L, W135, X, Y and Z, of which serogroups A, B, and C cause 90% of meningococcal disease (Poolman, J. T. et al, 1995, *Infectious Agents and Disease*, 4:13-28). Vaccines directed against serogroups A and C are available, but the serogroup B capsular polysaccharide is poorly immunogenic and does not induce protection in humans.

Other membrane and extracellular components are therefore being examined for their suitability for inclusion in vaccines. Examples include the outer membrane proteins of classes 1, 2 and 3 (porins), and classes 4 (Rmp) and 5 (Opacity proteins). However, to date, none of these candidates is able to induce complete protection, particularly in children (Romero, J. D., 1994, *Clinical Microbiology Review*, 7:559-575; Poolman, J. T. et al, 1995, supra).

To create an effective vaccine, it is necessary to identify components of *N. meningitidis* which are present in a majority of strains, and which are capable of inducing a protective immune response (bactericidal antibodies). In this regard, reference may be made to Brodeur et al. (International Publication WO 96/29412) who disclose a 22 kDa surface protein which is highly conserved across 99% of all known strains of *N. meningitidis*. Injection of purified recombinant 22-kDa surface protein protected 80% of immunized mice against development of a lethal infection by *N. meningitidis*. Notwithstanding the discovery of this protein, there is still a need to isolate more surface proteins of *N. meningitidis* which are highly conserved across a plurality of strains, and which have immuno-protective profiles against *N. meningitidis*, and/or which may be used in combination with other components of *N. meningitidis* to enhance the efficacy of protection against this organism.

SUMMARY OF THE INVENTION

The present inventors have discovered a new gene which is present in all tested strains of *N. meningitidis* and which encodes a novel polypeptide having a predicted molecular weight of about 62 kDa. Based upon its sequence characteristics and homologies, this polypeptide is predicted to be an adhesin and this, together with experimental data suggests that it constitutes a surface protein which may be useful for the production of therapeutic and/or prophylactic vaccines against *N. meningitides* as described hereinafter.

Accordingly, in one aspect of the invention, there is provided an isolated polypeptide or fragment thereof, or variant or derivative of these, said polypeptide selected from the group consisting of:—
  (a) a polypeptide according to SEQ ID NO 2;
  (b) a polypeptide according to SEQ ID NO 5;
  (c) a polypeptide according to SEQ ID NO 7;
  (d) a polypeptide according to SEQ ID NO 9;
  (e) a polypeptide according to SEQ ID NO 11;
  (f) a polypeptide according to SEQ ID NO 13;
  (g) a polypeptide according to SEQ ID NO 15;
  (h) a polypeptide according to SEQ ID NO 17;
  (i) a polypeptide according to SEQ ID NO 19; and
  (j) a polypeptide according to SEQ ID NO 21.

Preferably, said polypeptide, fragment, variant or derivative elicits an immune response against one or more members selected from the group consisting of:—
  (i) *N. meningitidis;*
  (ii) said polypeptide;
  (iii) said fragment;
  (iv) said variant; and
  (v) said derivative;

According to another aspect, the invention provides an isolated nucleic acid sequence encoding a polypeptide or fragment thereof, or variant or derivative of said fragment or polypeptide, according to the first-mentioned aspect. Suitably, said sequence is selected from the group consisting of:—
  (1) the nucleotide sequence of SEQ ID NO 1;
  (2) the nucleotide sequence of SEQ ID NO 3;
  (3) the nucleotide sequence of SEQ ID NO 4;
  (4) the nucleotide sequence of SEQ ID NO 6;
  (5) the nucleotide sequence of SEQ ID NO 8;
  (6) the nucleotide sequence of SEQ ID NO 10;
  (7) the nucleotide sequence of SEQ ID NO 12;
  (8) the nucleotide sequence of SEQ ID NO 14;
  (9) the nucleotide sequence of SEQ ID NO 16;
  (10) the nucleotide sequence of SEQ ID NO 18;
  (11) the nucleotide sequence of SEQ ID NO 20;
  (12) a nucleotide sequence fragment of any one of SEQ ID NOS 1, 3, 4, 6, 8, 10, 12, 14, 16, 18 and 20; and
  (13) a nucleotide sequence homologue of any of the foregoing sequences Preferably, said sequences encode a product that elicits an immune response against one or more members selected from the group consisting of:—
  (i) *N. meningitidis;*
  (ii) said polypeptide of the first-mentioned aspect;
  (iii) said fragment of said first-mentioned aspect;
  (iv) said variant of said first-mentioned aspect; and
  (v) said derivative of said first-mentioned aspect.

In yet another aspect, the invention resides in an expression vector comprising a nucleic acid sequence according to the second-mentioned aspect wherein said sequence is operably linked to transcriptional and translational regulatory nucleic acid.

In a further aspect, the invention provides a host cell containing an expression vector according to the third-mentioned aspect.

In yet a further aspect of the invention, there is provided a method of producing a recombinant polypeptide according to the first-mentioned aspect, said method comprising the steps of:—
  (A) culturing a host cell containing an expression vector according to the third-mentioned aspect such that said recombinant polypeptide is expressed from said nucleic acid; and
  (B) isolating said recombinant polypeptide.

In a still further aspect, the invention provides an antibody or antibody fragment that binds to one or more members selected from the group consisting of:—
  (1) *N. meningitidis;*
  (2) said polypeptide of the first-mentioned aspect;
  (3) said fragment of the first-mentioned aspect;
  (4) said variant of the first-mentioned aspect; and
  (5) said derivative of the first-mentioned aspect.

In yet another aspect, the invention provides a method of detecting *N. meningitidis* in a biological sample suspected of containing same, said method comprising the steps of:—
  (A) isolating the biological sample from a patient;
  (B) mixing the above-mentioned antibody or antibody fragment with the biological sample to form a mixture; and
  (C) detecting specifically bound antibody or bound antibody fragment in the mixture which indicates the presence of *N. meningitidis.*

According to a further aspect, there is provided a method of detecting *N. meningitidis* bacteria in a biological sample suspected of containing said bacteria, said method comprising the steps of:—
  (I) isolating the biological sample from a patient;
  (II) detecting a nucleic acid sequence according to the second-mentioned aspect in said sample which indicates the presence of said bacteria.

The invention further contemplates a method for diagnosing infection of patients by *N. meningitidis*, said method comprising the steps of:—
  (1) contacting a biological sample from a patient with a polypeptide, fragment, variant or derivative of the invention; and
  (2) determining the presence or absence of a complex between said polypeptide, fragment, variant or derivative and *N. meningitidis*-specific antibodies in said sample, wherein the presence of said complex is indicative of said infection.

The invention also extends to the use of the polypeptide according to the first-mentioned aspect, the use of the nucleic acids according to the second-mentioned aspect or the use of the antibody or antibody fragment mentioned above in a kit for detecting *N. meningitidis* bacteria in a biological sample.

According to a further aspect of the invention, there is provided a pharmaceutical composition comprising an isolated polypeptide or fragment thereof, or a variant or derivative of these, according to the first mentioned aspect.

Preferably, said pharmaceutical composition is a vaccine.

In yet a further aspect, the invention provides a method of preventing infection of a patient by *N. meningitidis*, comprising the step of administrating a pharmaceutically effective amount of the above-mentioned vaccine.

In a further aspect, the invention provides a method of identifying an immunoreactive fragment of a polypeptide, variant or derivatives according to the first mentioned aspect, comprising the steps of:—
  (a) producing a fragment of said polypeptide, variant or derivative;
  (b) administering said fragment to a mammal; and
  (c) detecting an immune response in said mammal which response includes production of elements which specifically bind *N. meningitidis* and/or said polypeptide, variant or derivative, and/or a protective effect against *N. meningitidis* infection.

BRIEF DESCRIPTION OF THE DRAWINGS

FIG. 6 shows a sequence comparison of polypeptides of HiaNm (SEQ ID NO: 2), Hia (SEQ ID NO: 32), Hsf (SEQ ID NO: 33) using the PILEUP alignment program; and FIG. 7 shows a sequence comparison of polypeptide sequences of HiaNm from 10 strains of *N. meningitidis* using the PILEUP program. FIG. 7 discloses SEQ ID NOS 11, 21, 2, 13, 5, 7, 9, 15, 17 and 19, respectively, in order of appearance.

DETAILED DESCRIPTION OF THE INVENTION

Figure 1:
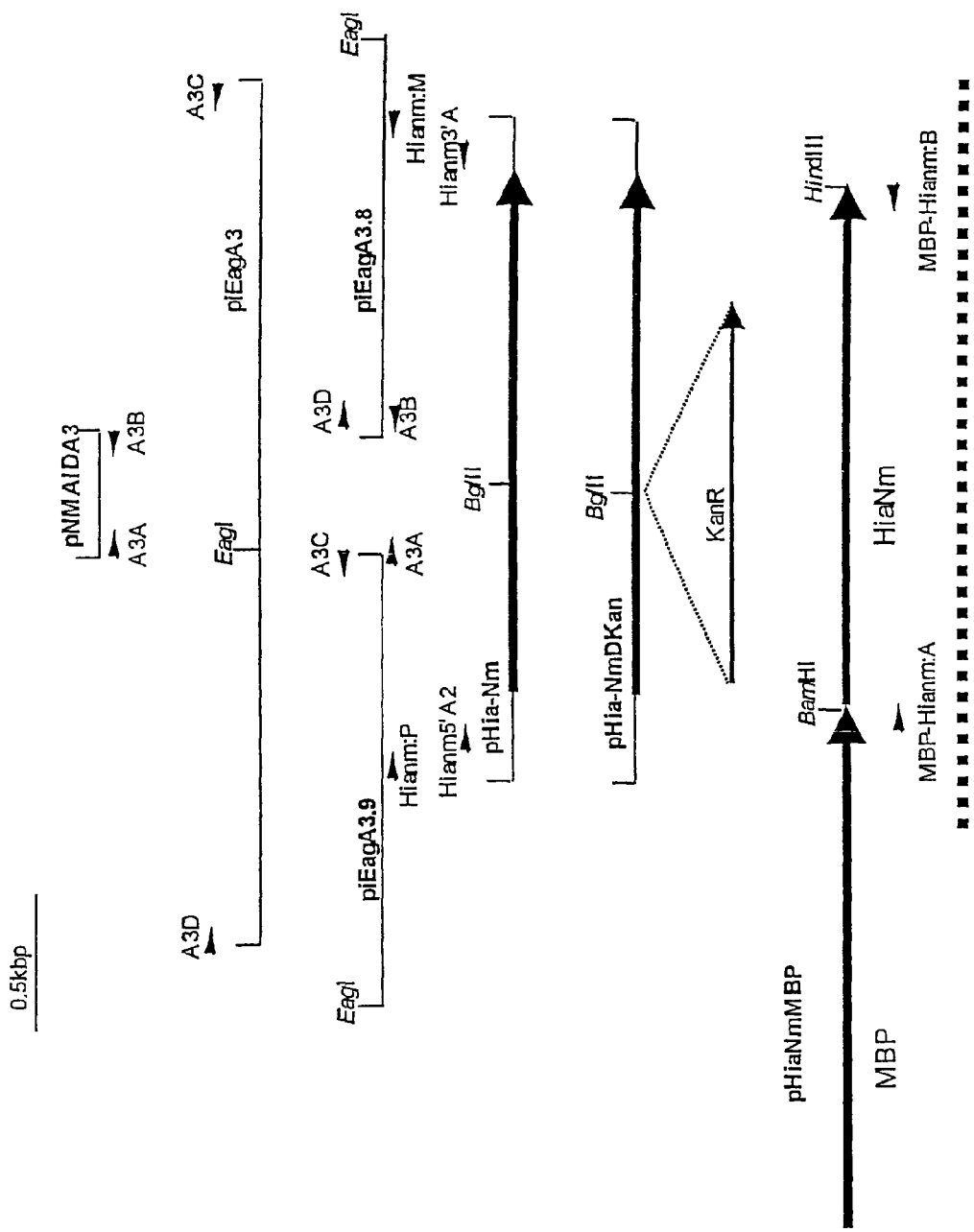
FIG. 1 depicts plasmid maps and cloning strategy. Primers A3A and A3B (SEQ ID NOS 28 and 29, respectively) were used to amplify from MC58 a region identified in preliminary sequence data as a homologue of AIDA-I (subsequently released by TIGR). PCR product was cloned to give pNMAIDA3. Primers A3C (SEQ ID NO 30) and A3D (SEQ ID NO 31) were used in inverse PCR to amplify a 3 kbp EagI fragment encompassing hiaNm. This product was cloned to give piEAGA3. piEAGA3 was subcloned to give piEagA3.8 and piEagA3.9. Primers HiaNm:M and HiaNm:P (SEQ ID NOS 22 and 23, respectively) were used to amplify the contiguous region from MC58 and the product cloned to create pHiaNm. Primers Hia-MBPA (SEQ ID NO 24) and Hia-MBPB (SEQ ID NO 25) were used to amplify the open reading frame of hiaNm, and the product was cloned into pMALC2 to create pMBP-HiaNm.
Figure 2A:
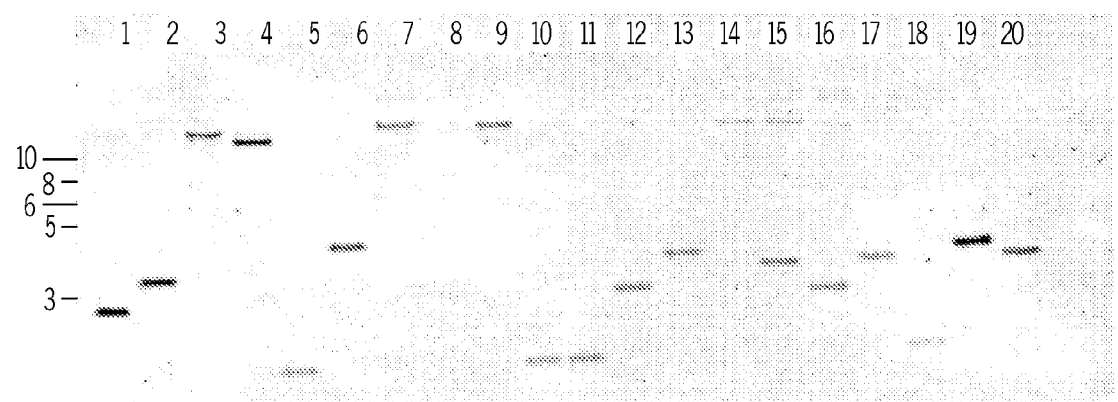
FIG. 2 is a Southern blot of genomic DNA of a number of strains of *N. meningitidis*. 2A: serogroup B strains. Lane 1 PMC28, Lane 2 PMC27, Lane 3 PMC25, Lane 4 PMC24, Lane 5 PMC16, Lane 6 PMC13, Lane 7 PMC12, Lane 8 MWt standards, Lane 9 2970, Lane 10 1000, Lane 11 528 Lane 12 SWZ107, Lane 13 H41, Lane 14 H38, Lane 15 NGH36, Lane 16 H15, Lane 17 NGG40, Lane 18 NGF26, Lane 19 NGE30, Lane 20 Lane NGE28 2B: Strains of serogroups other than B. Lane 1 PMC3, Lane 2 PMC17, Lane 3 PMC20, Lane 4 PMC23, Lane 5 PMC8, Lane 6 PMC9, Lane 7 PMC11, Lane 8 PMC14, Lane 9 PMC18, Lane 10 PMC21, Lane 11 PMC29, Lane 12 MWt standards, Lane 13 PMC19, Lane 14 PMC1, Lane 15 PMC6, Lane 16 PMC10, Lane 17 PMC22, Lane 18 PMC26, Lane 19 PMC2. Molecular weight markers indicated in kilobase pairs (kb). Genomic DNA was hybridized with a probe corresponding to ntp 276-2054 of SEQ ID NO 1.
Figure 2B:
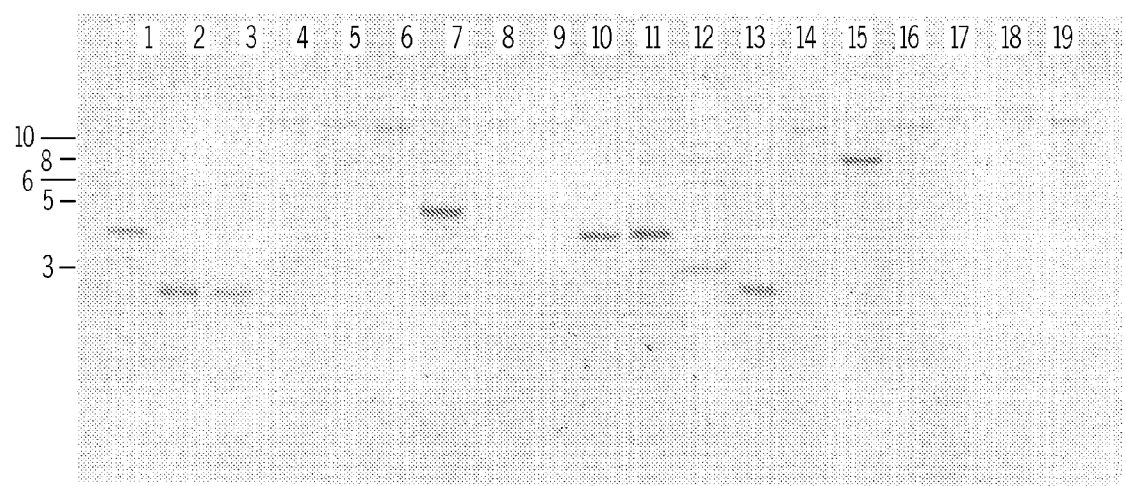
Figure 3:
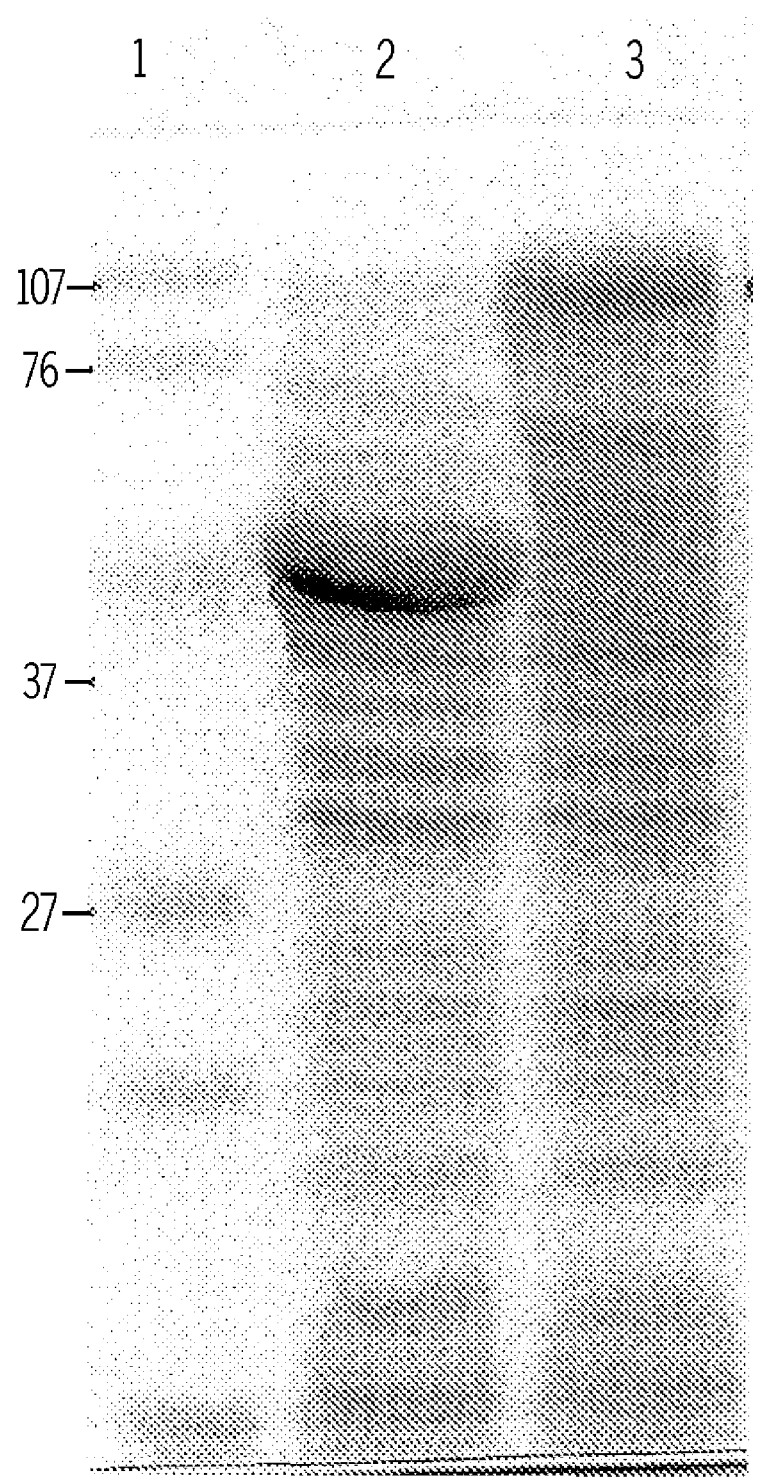
FIG. 3 shows a Coomassie stained gel of MBP-HiaNm. Cells containing pMALC2 (Lane 2) or pMBP-HiaNm (Lane 3) after induction with IPTG. Lane 1 molecular weight standards (kDa). Arrows indicate MBP and MBP-HiaNm.

Throughout this specification and the appendant claims, unless the context requires otherwise, the words "comprise", "comprises" and "comprising" will be understood to imply the inclusion of a stated integer or group of integers but not the exclusion of any other integer or group of integers.

Polypeptide Sequences

The present invention provides an isolated polypeptide according to SEQ ID NOS 2, 5, 7, 9, 11, 13, 15, 17, 19 and 21, or fragment respectively thereof, or variant or derivative of these. In a preferred embodiment, the polypeptide, fragments, variants and derivatives of the invention elicit an immune response against any one member selected from the group consisting of N. meningitidis, said polypeptide, said fragment, said variant and said derivative.

SEQ ID NO 2 corresponds to the novel about 62 kDa surface polypeptide of the hiaNm gene obtained from N. meningitidis strain MC58, as described more fully hereinafter. SEQ ID NOS 5, 7, 9, 11, 13, 15, 17, 19, and 21 correspond to homologous polypeptides deduced from nucleotide sequences obtained from N. meningitidis strains BZ10, BZ198, EG327, EG329, H15, H38, H41, P20, and PMC21, respectively.

For the purposes of this invention, the phrase "elicit(s) an immune response" refers to the ability of the aforementioned polypeptide, fragment, variant or derivative to produce an immune response in a mammal to which it is administered, wherein the response includes the production of elements which specifically bind N. meningitidis and/or said polypeptide, fragment, variant or derivative, and/or which provide a protective effect against N. meningitidis infection.

By "isolated" is meant material that is substantially or essentially free from components that normally accompany it in its native state.

By "polypeptide" is meant a long chain peptide including a protein.

As used herein, the term "fragment" includes deletion mutants and small peptides, for example of at least 6, preferably at least 10 and more preferably at least 20 amino acids in length, which comprise antigenic determinants or epitopes. Several such fragments may be joined together. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and staphylococcins V8-protease. The digested fragments can be purified by, for example, high performance liquid chromatographic (HPLC) techniques.

The term "variant" refers to polypeptides in which one or more amino acids halve been replaced by different amino acids. It is well understood in the art that some amino acids may be changed to others with broadly similar properties without changing the nature of the activity of the polypeptide (conservative substitutions). Exemplary conservative substitutions in the polypeptide may be made according to the following table:

TABLE 1

| Original Residue | Exemplary Substitutions |
| --- | --- |
| Ala | Ser |
| Arg | Lys |

TABLE 1-continued

| Original Residue | Exemplary Substitutions |
| --- | --- |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE 1. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

In general, variants will be at least 75% homologous, more suitably at least 80%, preferably at least 85%, and most preferably at least 90% homologous to the basic sequences as for example shown in SEQ ID NOS 2, 5, 7, 9, 11, 13, 15, 17, 19 and 21. Homology is defined as the percentage number of amino acids that are identical or constitute conservative substitutions as defined in Table 1. Homology may be determined using sequence comparison programs such as GAP (Deveraux et al. 1984, *Nucleic Acids Research* 12, 387-395) which is incorporated herein by reference. In this way sequences of a similar or substantially different length to those cited herein may be compared by insertion of gaps into the alignment, such gaps being determined, for example, by the comparison algorithm used by GAP. What constitutes suitable variants may be determined by conventional techniques. For example, nucleic acids encoding polypeptides according to SEQ ID NOS 2, 5, 7, 9, 11, 13, 15, 17, 19 and 21 can be mutated using either random mutagenesis for example using transposon mutagenesis, or site-directed mutagenesis. The resultant DNA fragments are then cloned into suitable expression hosts such as E. coli using conventional technology and clones that retain the desired activity are detected. Where the clones have been derived using random mutagenesis techniques, positive clones would have to be sequenced in order to detect the mutation. The term "variant" also includes naturally occurring allelic variants.

By "derivative" is meant a polypeptide that has been derived from the basic sequence by modification, for example by conjugation or complexing with other chemical moieties or by post-translational modification techniques as would be understood in the art. Such derivatives include amino acid deletions and/or additions to polypeptides according to SEQ ID NOS 2, 51 7, 9, 11, 13, 15, 17, 19 and 21 or variants thereof wherein said derivatives retain activity eliciting an immune response. "Additions" of amino acids may include fusion of the polypeptides or variants thereof with other polypeptides or proteins. In this regard, it will be appreciated that the polypeptides or variants of the invention may be incorporated into larger polypeptides, and such larger polypeptides may also be expected to retain immunological activity against, for example, *N. meningitidis*. The polypeptides as described above may be fused to a further protein, for example, which is not derived from *N. meningitidis*. The other protein may, by way of example, assist in the purification of the protein. For instance a polyhistidine tag, or a maltose binding protein may be used in this respect as described in more detail below. Alternatively, it may produce an immune response, which is effective against *N. meningitidis*, or it may produce an immune response against another pathogen. Other possible fusion proteins are those which produce an immunomodulatory response. Particular examples of such proteins include Protein A or glutathione S-transferase (GST). In addition, the polypeptide may be fused to an oligosaccharide based vaccine component where it acts as a carrier protein.

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention.

Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with NaBH$_4$; reductive alkylation by reaction with an aldehyde followed by reduction with NaBH$_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in TABLE 2.

TABLE 2

| Non-conventional amino acid | Non-conventional amino acid |
| --- | --- |
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcyclopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

The invention also contemplates covalently modifying a polypeptide, fragment or variant of the invention with dinitrophenol, in order to render it immunogenic in humans Preferably the invention comprises a polypeptide selected from any one of the polypeptides according to SEQ ID NOS 2, 5, 7, 9, 11, 13, 15, 17, 19 and 21.

Polypeptides of the inventions may be prepared by any suitable procedure known to those of skill in the art. For example, the polypeptides may be prepared by a procedure including the steps of:

(a) preparing a recombinant nucleic acid containing a nucleotide sequence encoding a polypeptide according to any one of SEQ ID NOS 2, 5, 7, 9, 11, 13, 15, 17, 19 and 21, or fragment thereof, or variant or derivative of these, which nucleotide sequence is operably linked to transcriptional and translational regulatory nucleic acid;

(b) transfecting or transforming a suitable host cell with the recombinant nucleic acid;

(c) culturing the host cell to express recombinant polypeptide from said recombinant nucleic acid; and (d) isolating the recombinant polypeptide.

Suitably said nucleotide sequence is selected from the group consisting of SEQ ID NOS 1, 3, 4, 6, 8, 10, 12, 14, 16, 18 and 20.

By "recombinant polypeptide" is meant a polypeptide made using recombinant techniques, i.e., through the expression of a recombinant nucleic acid.

The term "recombinant nucleic acid" as used herein refers to nucleic acid formed in vitro by the manipulation of nucleic acid into a form not normally found in nature. In this regard, the recombinant nucleic acid preferably comprises an expression vector that may be either a self-replicating extra-chromosomal vector such as a plasmid, or a vector that integrates into a host genome. Generally, such expression vectors include transcriptional and translational regulatory nucleic acid operably linked to the said nucleotide sequence.

By "operably linked" is meant that the transcriptional and translational regulatory nucleic acid is positioned relative to the nucleotide sequence encoding the said polypeptide, fragment, variant or derivative in such a manner that such transcription is initiatable. The transcriptional and translational regulatory nucleic acid will generally be appropriate for the host cell used for expression. Numerous types of appropriate expression vectors and suitable regulatory sequences are known in the art for a variety of host cells.

Typically, the transcriptional and translational regulatory nucleic acid may include, but is not limited to, promoter sequences, leader or signal sequences, ribosomal binding sites, transcriptional start and stop sequences, translational start and stop sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist, identification and/or purification of said fusion polypeptide.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-S-transferase (GST), Fc potion of human IgG, maltose binding protein (MBP) and hexahistidine ($HIS_6$) (SEQ ID NO: 34), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) (SEQ ID NO: 34) fusion.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

Recombinant polypeptides of the invention may be produced by culturing a host cell transformed with an expression vector containing nucleic acid encoding a polypeptide, fragment, variant or derivative according to the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilized with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), incorporated herein by reference, in particular Sections 16 and 17; Ausubel et al., CURRENT PROTOCOLS IN MOLECULAR BIOLOGY (John Wiley & Sons, Inc. 1994-1998), incorporated herein by reference, in particular Chapters 10 and 16; and Coligan et al., CURRENT PROTOCOLS IN PROTEIN SCIENCE (John Wiley & Sons, Inc. 1995-1997) which is incorporated by reference herein, in particular Chapters 1, 5 and 6.

Nucleotide Sequences

The invention further provides a nucleotide sequence that encodes a polypeptide, fragment, variant or derivative as defined above. Suitably, said sequence is selected from the group consisting of:—SEQ ID NOS 1, 3, 4, 6, 8, 10, 12, 14, 16, 18 and 20; a nucleotide sequence fragment of any one of SEQ ID NOS 1, 3, 4, 6, 8, 10, 12, 14, 16, 18 and 20; and a nucleotide sequence homologue of the foregoing sequences. Suitably, these sequences encode a product that elicits an immune response as defined above.

As will be more fully described hereinafter, SEQ ID NO 1 corresponds to the hiaNm gene obtained from *N. meningitidis* strain MC58. This gene encodes the novel 62 kDa (approximately) surface polypeptide of SEQ ID NO 2. SEQ ID NO 3 corresponds to the hiaNim open reading frame sequence of strain MC58, HiaNm. SEQ ID NOS 4, 6, 8, 10, 12, 14, 16, 18, and 20 correspond to the homologous hiaNm open reading frame sequences obtained from *N. meningitidis* strains BZ10, BZ198, EG327, EG329, H15, H38, H41, P20, and PMC21, respectively.

The term "nucleotide sequence" as used herein designates mRNA, RNA, cRNA, cDNA or DNA.

The term "nucleotide sequence homologues" generally refers to nucleotide sequences that hybridize with a wild-type nucleotide sequence according to the invention under substantially stringent conditions. Suitable hybridization conditions will be discussed hereinafter.

The nucleotide sequence homologues of the invention may be prepared according to the following procedure:
(i) obtaining a nucleic acid extract from a suitable host;
(ii) creating primers which are optionally degenerate wherein each comprises a portion of a wild-type nucleotide sequence of the invention; and
(iii) using said primers to amplify, via nucleic acid amplification techniques, one or more amplification products from said nucleic acid extract.

Suitably, the host may be a bacterium. Preferably, the host is from the genus *Neisseria*, more preferably from *N. meningitidis*.

Preferably, the primers are selected from the group consisting of:—

```
                                              (SEQ ID NO 22)
(1)  5'-TTAGATTCCACGTCCCAGATT-3';

(SEQ ID NO 23)
(2)  5'-CTTCCCTTCAAACCTTCC3';

(SEQ ID NO 24)
(3)  5'-GGTCGCGGATCCATGAACAAAATATACCGCAT-3';

(SEQ ID NO 25)
(4)  5'-TCACCCAAGCTTAAGCCCTTACCACTGATAAC-3';

(SEQ ID NO 26)
(5)  5'-CCAAACCCCGATTTAACC-3';

(SEQ ID NO 27)
(6)  5'-AATCGCCACCCTTCCCTTC-3';

(SEQ ID NO 28)
(7)  5'-TTTGCAACGGTTCAGGCA-3';

(SEQ ID NO 29)
(8)  5'-TATTCAGCAGCGTATCGG-3';

(SEQ ID NO 30)
(9)  5'-TGCCTGAACCGTTGCAAA-3';
and (SEQ ID NO 31)
(10) 5'-CCGATACGCTGCTGAATA-3'.
```

Suitable nucleic acid amplification techniques are well known to the skilled addressee, and include polymerase chain reaction (PCR) as for example described in Ausubel et al. (1994-1998, supra, Chapter 15) which is incorporated herein by reference; strand displacement amplification (SDA) as for example described in U.S. Pat. No. 5,422,252 which is incorporated herein by reference; rolling circle replication (RCR) as for example described in Liu et al., (1996, *J. Am. Chem. Soc.* 118:1587-1594 and International application WO 92/01813) and Lizardi et al., (International Application WO 97/19193) which are incorporated herein by reference; nucleic acid sequence-based amplification (NASBA) as for example described by Sooknanan et al., (1994, *Biotechniques* 17:1077-1080) which is incorporated herein by reference; and Q-β replicase amplification as for example described by Tyagi: et al., (1996, *Proc. Natl. Acad. Sci. USA* 93:5395-5400) which is incorporated herein by reference.

As used herein, an "amplification product" refers to a nucleic acid product generated by nucleic acid amplification techniques.

"Hybridize" or "hybridization" is used here to denote the pairing of complementary bases of distinct nucleotide sequences to produce a DNA-DNA hybrid, a DNA-RNA hybrid, or an RNA-RNA hybrid according to base-pairing rules.

In DNA, complementary bases are:
(i) A and T; and
(ii) C and G.
In RNA, complementary bases are:
(i) A and U; and
(ii) C and G.
In RNA-DNA hybrids, complementary bases are:
(i) A and U;
(ii) A and T; and
(iii) G and C.

Typically, substantially complementary nucleotide sequences are identified by blotting techniques that include a step whereby nucleotides are immobilized on a matrix (preferably a synthetic membrane such as nitrocellulose), a hybridization step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994-1998, supra) at pages 2.9.1 through 2.9.20.

According to such methods, Southern blotting involves separating DNA molecules according to size by gel electrophoresis, transferring the size-separated DNA to a synthetic membrane, and hybridizing the membrane bound DNA to a complementary nucleotide sequence labeled radioactively, enzymatically or fluorochromatically. In dot blotting and slot blotting, DNA samples are directly applied to a synthetic membrane prior to hybridization as above.

An alternative blotting step is used when identifying complementary nucleotide sequences in a cDNA or genomic DNA library, such as through the process of plaque or colony hybridization. A typical example of this procedure is described in Sambrook et al., (1989, supra) Chapters 8-12.

Typically, the following general procedure can be used to determine hybridization conditions. Nucleotide sequences are blotted/transferred to a synthetic membrane, as described above. A wild type nucleotide sequence of the invention is labeled as described above, and the ability of this labeled nucleotide sequence to hybridize with an immobilized nucleotide sequence analyzed.

A skilled addressee will recognize that a number of factors influence hybridization. The specific activity of radioactively labeled polynucleotide sequence should typically be greater than or equal to about $10^8$ dpm/mg to provide a detectable signal. A radiolabeled nucleotide sequence of specific activity $10^8$ to $10^9$ dpm/mg can detect approximately 0.5 pg of DNA. It is well known in the art that sufficient DNA must be immobilized on the membrane to permit detection. It is desirable to have excess immobilized DNA, usually 10 μg. Adding an inert polymer such as 10% (w/v) dextran sulfate (MW 500, 000) or polyethylene glycol 6000 during hybridization can also increase the sensitivity of hybridization (see Ausubel supra at 2.10.10).

To achieve meaningful results from hybridization between a nucleotide sequence immobilized on a membrane and a labeled nucleotide sequence, a sufficient amount of the labeled nucleotide sequence must be hybridized to the immobilized nucleotide sequence following washing. Washing ensures that the labeled nucleotide sequence is hybridized only to the immobilized nucleotide sequences with a desired degree of complementarity to the labeled nucleotide sequence.

"Stringency" as used herein, refers to the temperature and ionic strength conditions, and presence or absence of certain organic solvents, during hybridization. The higher the stringency, the higher will be the degree of complementarity between the immobilized nucleotide sequences and the labeled polynucleotide sequence.

"Stringent conditions" designates those conditions under which only nucleotide sequences having a high frequency of complementary bases will hybridize.

Typical stringent conditions include, for example, (1) 0.75 M dibasic sodium phosphate/0.5 M monobasic sodium phosphate/1 mM disodium EDTA/1% sarkosyl at about 42° C. for at least 30 minutes; or (2) 6.0 M urea/0.4% sodium lauryl sulfate/0.1×SSC at about 42° C. for at least 30 minutes; or (3) 0.1×SSC/0.1% SDS at about 68° C. for at least 20 minutes; or (4) 1×SSC/0.1% SDS at about 55° C. for about 60 minutes; or (5) 1×SSC/0.1% SDS at about 62° C. for about 60 minutes; or (6) 1×SSC/0.1% SDS at about 68° C. for about 60 minutes; or (7) 0.2×SSC/0.1% SDS at about 55° C. for about 60 minutes; or (8) 0.2×SSC/0.1% SDS at about 62° C. for about one hour; or (9) 0.2×SSC/0.1% SDS at about 68° C. for about 60 minutes. For a detailed example, see CURRENT PROTOCOLS IN MOLECULAR BIOLOGY supra at pages 2.10.1 to 2.10.16 and Sambrook et al. in MOLECULAR CLONING. A LABORATORY MANUAL (Cold Spring Harbour Press, 1989) at sections 1.101 to 1.104, which are hereby incorporated by reference.

While stringent washes are typically carried out at temperatures from about 42° C. to 68° C., one skilled in the art will appreciate that other temperatures may be suitable for stringent conditions. Maximum hybridization typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see CURRENT PROTOCOLS IN MOLECULAR BIOLOGY supra at page 2.10.8). Maximum hybridization typically occurs at about 10° C. to 15° C. below the $T_m$ for a DNA-RNA hybrid.

Other stringent conditions are well known in the art. A skilled addressee will recognize that various factors can be manipulated to optimize the specificity of the hybridization. Optimization of the stringency of the final washes can serve to ensure a high degree of hybridization.

Methods for detecting labeled nucleotide sequences hybridized to an immobilized nucleotide sequence are well known to practitioners in the art. Such methods include autoradiography, chemiluminescent, fluorescent and colorimetric detection.

Antibodies

The invention also contemplates antibodies against the aforementioned polypeptides, fragments, variants and derivatives. Such antibodies may include any suitable antibodies that bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991) which is incorporated herein by reference, and Ausubel et al., (1994-1998, supra), in particular Section III of Chapter 1.1.

In lieu of the polyclonal antisera obtained in the production species, monoclonal antibodies may be produced using the standard method as for example, described in an article by Köhler and Milstein (1975, Nature 256, 495-497) which is herein incorporated by reference, or by more recent modifications thereof as for example, described in Coligan et al., (1991, supra) by immortalizing spleen or other antibody producing cells derived from a production species which has been inoculated with one or more of the polypeptides, fragments, variants or derivatives of the invention.

The invention also includes within its scope antibodies which comprise Fc or Fab fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No. 5,091,513, European Patent No 239,400 or the article by Winter and Milstein (1991, Nature, 349 293) which are incorporated herein by reference.

The antibodies of the invention may be used for affinity chromatography in isolating natural or recombinant N. meningitidis polypeptides. For example reference may be made to immunoaffinity chromatographic procedures described in Chapter 9.5 of Coligan et al., (1995-1997, supra).

The antibodies can be used to screen expression libraries for variant polypeptides of the invention. The antibodies of the invention can also be used to detect N. meningitidis infection described hereinafter.

Detection of N. meningitidis

The presence or absence of N. meningitidis in a patient may determined by isolating a biological sample from a patient, mixing an antibody or antibody fragment described above with the biological sample to form a mixture, and detecting specifically bound antibody or bound fragment in the mixture which indicates the presence of N. meningitidis in the sample.

The term "biological sample" as used herein refers to a sample that may be extracted, untreated, treated, diluted or concentrated from a patient. Suitably, the biological sample is selected from the group consisting of whole blood, serum, plasma, saliva, urine, sweat, ascitic fluid, peritoneal fluid, synovial fluid, amniotic fluid, cerebrospinal fluid, skin biopsy, and the like.

Any suitable technique for determining formation of the complex may be used. For example, an antibody or antibody fragment according to the invention having a label associated therewith may be utilized in immunoassays. Such immunoassays may include, but are not limited to, radioimmunoassays (RIAs), enzyme-linked immunosorbent assays (ELISAs) and immunochromatographic techniques (ICTs) which are well known those of skill in the art. For example, reference may be made to "CURRENT PROTOCOLS IN IMMUNOLOGY" (1994, supra) which discloses a variety of immunoassays that may be used in accordance with the present invention. Immunoassays may include competitive assays as understood in the art.

The label associated with the antibody or antibody fragment may include the following:
i. direct attachment of the label to the antibody or antibody fragment;
ii. indirect attachment of the label to the antibody or antibody fragment; i.e., attachment of the label to another assay reagent which subsequently binds to the antibody or antibody fragment; and
iii. attachment to a subsequent reaction product of the antibody, or antibody fragment.

The label may be selected from a group including a chromogen, a catalyst, an enzyme, a fluorophore, a chemiluminescent molecule, a lanthanide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as labels is disclosed in United States Patent Specifications U.S. Pat. No. 4,366,241, U.S. Pat. No. 4,843,000, and U.S. Pat. No. 4,849,338, all of which are herein incorporated by reference. Suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme that is in solution.

Suitably, the fluorophore is selected from a group including fluorescein isothiocyanate (FITC), tetramethylrhodamine isothiocyanate (TRITL) or R-Phycoerythrin (RPE).

The invention also extends to a method for detecting infection of patients by *N. meningitidis*, said method comprising the steps of contacting a biological sample from a patient with a polypeptide, fragment, variant or derivative of the invention, and determining the presence or absence of a complex between said polypeptide, fragment, variant or derivative and *N. meningitidis*-specific antibodies in said serum, wherein the presence of said complex is indicative of said infection.

In a preferred embodiment, detection of the above complex is effected by detectably modifying said polypeptide, fragment, variant or derivative with a suitable label as is well known in the art and using such modified compound in a suitable immunoassay as for example described above.

In another aspect, the invention provides a method of detecting *N. meningitides* bacteria in a biological sample suspected of containing said bacteria, said method comprising the steps of isolating the biological sample from a patient, detecting a nucleic acid sequence according to the invention in said sample which indicates the presence of said bacteria.

Detection of the said nucleic acid sequence may be determined using any suitable technique. For example, a labeled nucleic acid sequence according to the invention may be used as a probe in a Southern blot of a nucleic acid extract obtained from a patient as is well known in the art. Alternatively, a labeled nucleic acid sequence according to the invention may be utilized as a probe in a Northern blot of a RNA extract from the patient. Preferably, a nucleic acid extract from the patient is utilized in concert with oligonucleotide primers corresponding to sense and antisense sequences of a nucleic acid sequence according to the invention, or flanking sequences thereof, in a nucleic acid amplification reaction such as PCR, or the ligase chain reaction (LCR) as for example described in International Application WO89/09385 which is incorporated by reference herein. A variety of automated solid-phase detection techniques are also appropriate. For example, very large scale immobilized primer arrays (VLSIPS™) are used for the detection of nucleic acids as for example described by Fodor et al., (1991, *Science* 251:767-777) and Kazal et al., (1996, *Nature Medicine* 2:753-759). The above generic techniques are well known to persons skilled in the art.

Pharmaceutical Compositions

A further feature of the invention is the use of the polypeptide, fragment, variant or derivative of the invention ("immunogenic agents") as actives in a pharmaceutical composition for protecting patients against infection by *N. meningitides*. Suitably, the pharmaceutical composition comprises a pharmaceutically acceptable carrier.

By "pharmaceutically-acceptable carrier" is meant a solid or liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is immunogenically-effective to protect patients from *N. meningitidis* infection. The dose administered to a patient, in the context of the present invention, should be sufficient to effect a beneficial response in a patient over time such as a reduction in the level of *N. meningitidis*, or to inhibit infection by *N. meningitidis*. The quantity of the immunogenic agent(s)

to be administered may depend on the subject to be treated inclusive of the age, sex, weight and general health condition thereof. In this regard, precise amounts of the immunogenic agent(s) required to be administered will depend on the judgement of the practitioner. In determining the effective amount of the immunogenic agent to be administered in the treatment or prophylaxis against N. meningitidis, the physician may evaluate circulating plasma levels, progression of disease, and the production of anti-N. meningitidis antibodies. In any event, suitable dosages of the immunogenic agents of the invention may be readily determined by those of skill in the art. Such dosages may be in the order of nanograms to milligrams of the immunogenic agents of the invention.

The above compositions may be used as therapeutic or prophylactic vaccines. Accordingly, the invention extends to the production of vaccines containing as actives one or more of the immunogenic agents of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong), which is incorporated herein by reference.

An immunogenic agent according to the invention can be mixed, conjugated or fused with other antigens, including B or T cell epitopes of other antigens. In addition, it can be conjugated to a carrier as described below.

When an haptenic peptide of the invention is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas, E. coli, Staphylococcus*, and *Streprococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immnogenic protein may be used. For example, a haptenic peptide of the invention can be coupled to a T cell epitope of a bacterial toxin, toxoid or CRM. In this regard, reference may be made to U.S. Pat. No. 5,785,973 which is incorporated herein by reference.

In addition, a polypeptide, fragment, variant or derivative of the invention may act as a carrier protein in vaccine compositions directed against *Neisseria*, or against other bacteria or viruses.

The immunogenic agents of the invention may be administered as multivalent subunit vaccines in combination with antigens of *N. meningitidis*, or antigens of other organisms inclusive of the pathogenic bacteria *H. influenzae, M. catarrhalis, N. gonorrhoeae, E. Coli, S. pneumoniae* etc. Alternatively or additionally, they may be administered in concert with oligosaccharide or polysaccharide components of *N. meningitidis*.

The vaccines can also contain a physiologically acceptable diluent or excipient such as water, phosphate buffered saline and saline.

The vaccines and immunogenic compositions may include an adjuvant as is well known in the art. Suitable adjuvants include, but are not limited to: surface active substances such as hexadecylamine, octadecylamine, octadecyl amino acid esters, lysolecithin, dimethyldioctadecylammonium bromide, N,N-dicoctadecyl-N',N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

The immunogenic agents of the invention may be expressed by attenuated viral hosts. By "attenuated viral hosts" is meant viral vectors that are either naturally, or have been rendered, substantially avirulent. A virus may be rendered substantially avirulent by any suitable physical (e.g., heat treatment) or chemical means (e.g., formaldehyde treatment). By "substantially avirulent" is meant a virus whose infectivity has been destroyed. Ideally, the infectivity of the virus is destroyed without affecting the proteins that carry the immunogenicity of the virus. From the foregoing, it will be appreciated that attenuated viral hosts may comprise live viruses or inactivated viruses.

Attenuated viral hosts which may be useful in a vaccine according to the invention may comprise viral vectors inclusive of adenovirus, cytomegalovirus and preferably pox viruses such as vaccinia (see for example Paoletti and Panicali, U.S. Pat. No. 4,603,112 which is incorporated herein by reference) and attenuated *Salmonella* strains (see for example Stocker, U.S. Pat. No. 4,550,081 which is herein incorporated by reference). Live vaccines are particularly advantageous because they lead to a prolonged stimulus that can confer substantially long-lasting immunity.

Multivalent vaccines can be prepared from one or more microorganisms that express different epitopes of *N. meningitidis* (e.g., other surface proteins or epitopes of *N. meningitidis*). In addition, epitopes of other pathogenic microorganisms can be incorporated into the vaccine.

In a preferred embodiment, this will involve the construction of a recombinant vaccinia virus to express a nucleic acid sequence according to the invention. Upon introduction into a host, the recombinant vaccinia virus expresses the immunogenic agent, and thereby elicits a host CTL response. For example, reference may be made to U.S. Pat. No. 4,722,848, incorporated herein by reference, which describes vaccinia vectors and methods useful in immunization protocols.

A wide variety of other vectors useful for therapeutic administration or immunization with the immunogenic agents of the invention will be apparent to those skilled in the art from the present disclosure.

In a further embodiment, the nucleotide sequence may be used as a vaccine in the form of a "naked DNA" vaccine as is known in the art. For example, an expression vector of the invention may be introduced into a mammal, where it causes production of a polypeptide in vivo, against which the host mounts an immune response as for example described in Barry, M. et al., (1995, *Nature*, 377:632-635) which is hereby incorporated herein by reference.

Detection Kits

The present invention also provides kits for the detection of *N. meningitidis* in a biological sample. These will contain one or more particular agents described above depending upon the nature of the test method employed. In this regard, the kits may include one or more of a polypeptide, fragment, variant, derivative, antibody, antibody fragment or nucleic acid according to the invention. The kits may also optionally include appropriate reagents for detection of labels, positive and negative controls, washing solutions, dilution buffers and the like. For example, a nucleic acid-based detection kit may include (i) a nucleic acid according to the invention (which may be used as a positive control), (ii) an oligonucleotide primer according to the invention, and optionally a DNA polymerase, DNA ligase etc depending on the nucleic acid amplification technique employed.

Preparation of Immunoreactive Fragments

The invention also extends to a method of identifying an immunoreactive fragment of a polypeptide, variant or derivatives according to the invention. This method essentially comprises generating a fragment of the polypeptide, variant or derivative, administering the fragment to a mammal; and detecting an immune response in the mammal. Such response will include production of elements which specifically bind N. meningitidis and/or said polypeptide, variant or derivative, and/or a protective effect against N. meningitidis infection.

Prior to testing a particular fragment for immunoreactivity in the above method, a variety of predictive methods may be used to deduce whether a particular fragment can be used to obtain an antibody that cross-reacts with the native antigen. These predictive methods may be based on amino-terminal or carboxy-terminal sequence as for example described in Chapter 11.14 of Ausubel et al., (1994-1998, supra.). Alternatively, these predictive methods may be based on predictions of hydrophilicity as for example described by Kyte and Doolittle (1982, *J. Mol. Biol.* 157:105-132) and Hopp and Woods (1983, *Mol. Immunol.* 20:483-489) which are incorporated by reference herein, or predictions of secondary structure as for example described by Choo and Fasman (1978, *Ann. Rev. Biochem.* 47:251-276), which is incorporated herein by reference.

Generally, peptide fragments consisting of 10 to 15 residues provide optimal results. Peptides as small as 6 or as large as 20 residues have worked successfully. Such peptide fragments may then be chemically coupled to a carrier molecule such as keyhole limpet hemocyanin (KLH) or bovine serum albumin (BSA) as for example described in Sections 11.14 and 11.15 of Ausubel et al., (1994-1998, supra).

The peptides may be used to immunize an animal as for example discussed above. Antibody titers against the native or parent polypeptide from which the peptide was selected may then be determined by, for example, radioimmunoassay or ELISA as for instance described in Sections 11.16 and 114 of Ausubel et al., (1994-1998, supra).

Antibodies may then be purified from a suitable biological fluid of the animal by ammonium sulfate fractionation or by chromatography as is well known in the art. Exemplary protocols for antibody purification is given in Sections 10.11 and 11.13 of Ausubel et al., (1994-1998, supra).

Immunoreactivity of the antibody against the native or parent polypeptide may be determined by any suitable procedure such as, for example, western blot.

Functional Blockers

The polypeptides according to SEQ ID NOS 2, 5, 7, 9, 11, 13, 15, 17, 19 and 21 are believed to have adhesin properties. They in fact have some similarity to adhesins of *Haemophilus influenzae*, which are surface antigens. Specifically they are approximately 67% homologous to the Hia protein of *H. influenzae* (Barenkamp, S. and St. Geme III, *J.* 1996 *Molecular Microbiology* 19: 1215-1233), and 74% homologous to the Hsf protein of *H. influenzae* (St. Geme III, J. et al, 1996, *Journal of Bacteriology* 178: 6281-6287; and U.S. Pat. No. 5,646,259). For these comparisons, a gap weight of 3, and length weight of 0.01 was used using the GAP program (Deveraux, 1984, supra). Aligned sequences of these proteins are illustrated in FIG. 6. Thus, interruption of the function of these polypeptides would be of significant therapeutic benefit since they would prevent N. meningitidis bacteria from adhering to and invading cells. Interruption of the function may be effected in several ways.

For example, moieties such as chemical reagents or polypeptides which block receptors on the cell surface which interact with a polypeptides according to SEQ ID NOS 2, 5, 7, 9, 11, 13, 15, 17, 19 and 21 may be administered. These compete with the infective organism for receptor sites. Such moieties may comprise for example polypeptides of the invention, in particular fragments, or functional equivalents of these as well as mimetics.

The term "mimetics" is used herein to refer to chemicals that are designed to resemble particular functional regions of the proteins or peptides. Anti-idiotypic antibodies raised against the above-described antibodies which block the binding of the bacteria to a cell surface may also be used. Alternatively, moieties which interact with the receptor binding sites in the polypeptides according to SEQ ID NO 2, 5, 7, 9, 11, 13, 15, 17, 19 and 21 may effectively prevent infection of a cell by N. meningitidis. Such moieties may comprise blocking antibodies, peptides or other chemical reagents.

All such moieties, pharmaceutical compositions in which they are combined with pharmaceutically acceptable carriers and methods of treating patients suffering from N. meningitidis infection by administration of such moieties or compositions form a further aspect of the invention.

The polypeptides of the invention may be used in the screening of compounds for their use in the above methods. For example, polypeptides of the invention may be combined with a label and exposed to a cell culture in the presence of a reagent under test. The ability of reagent to inhibit the binding of the labeled polypeptide to the cell surface can then be observed. In such a screen, the labeled polypeptides may be used directly on an organism such as *E. coli*. Alternatively, N. meningitidis itself may be engineered to express a modified and detectable form of the polypeptide. The use of engineered N. meningitidis strains in this method is preferred as it is more likely that the tertiary structure of the protein will resemble more closely that expressed in wild-type bacteria.

In order that the invention may be readily understood and put into practical effect, particular preferred embodiments will now be described by way of the following non-limiting examples.

Example 1

Molecular Cloning and Subcloning and HiaNm Mutant Construction

The hiaNm gene was initially isolated by PCR amplification using standard methods. Briefly, due to our previous work on homologues of the AIDA-I protein of *E. coli* (Jennings, M. et al, 1995, *Microbial Pathogenesis*, 19: 391-407, Peak, I. et al, *Microbial Pathogenesis*, in press) we performed a homology search, identifying a sequence of interest in preliminary data from the project to sequence the genome of MC58¢3 (subsequently released by The Institute for Genomic Research, Maryland, ftp://ftp.tigr.org/pub/data/n meningitidis/) and amplified the region of homology by PCR using oligonucleotides A3A (5'-TTTGCAACGGTTCAG-GCA-3', SEQ ID NO 28) and A3B (5'-TATTCAGCAGCG-TATCGG-3', SEQ ID NO 29. The resulting 449 base pairs (bp) product was cloned into pT7Blue, to create plasmid pNMAIDA3. To clone the full-length gene, further oligonucleotides were designed and used in an inverse PCR reaction. These oligonucleotides were A3C (SEQ ID NO 30) and A3D (SEQ ID NO 31) and correspond to the complementary sequence of A3A (SEQ ID NO 28) and A3B (SEQ ID NO 31) respectively. The template for this reaction was chromosomal DNA of MC58, which had been restriction digested with EagI, and then self ligated. The resulting 3 kbp PCR product was cloned into the vector pCRII (Invitrogen), producing plasmid piEagA3. This was digested with EagI and EcoRI and the resulting fragments of 1.4 kbp and 1.6 kbp containing cloned DNA were cloned into pBluescriptSKII, M13minus (Stratagene), resulting in piEagA3.8 and piEagA3.9. Plasmid pHiaNm was generated by PCR amplifying hiaNm and sequence 5' and 3' to it using oligonucleotide primers HiaNm:P (5'-TTAGATTCCACGTCCCAGATT-3', SEQ ID NO 22) and HiaNm:M (5'-CTTCCCTTCAAACCTTCC-31, SEQ ID NO 23), corresponding to nucleotide position (ntp) 113-133 and 2102-2085 respectively of SEQ ID NO 1, and cloning the product into pT7Blue. Plasmid pHiaNmΔKan was created by insertion of a kanamycin resistance cassette into the unique BglII site of pHiaNm corresponding to ntp 680 of SEQ ID No 1. The kanamycin resistance cassette was excised from pUC4Kan (Pharmacia) with BamHI. pHiaNm-ΔKan was transformed into *N. meningitidis* strain MC58 by incubating bacteria with plasmid DNA for 3 hours on Brain Heart Infusion agar (Acumedia Manufacturer's Inc) supplemented with 10% heated horse blood ("BHI plates") at 37° C. in 5% $CO_2$. A single colony was picked onto fresh selective media, grown, and used for further studies. This mutant strain is designated MC58ΔHiaNm. Disruption of the hiaNm gene in this strain was confirmed by Southern blot using a probe corresponding to ntp 276-2054 of SEQ ID NO 1.

Example 2

Nucleotide Sequence Analysis

Nucleotide sequence analysis was performed using the PRISM Dye terminator sequencing Kit with AmpliTaq DNA polymerase FS or BigDye terminator sequencing kit as suggested by the manufacturer's instructions (Perkin Elmer), in conjunction with a model 373a automated sequencer (Applied Biosystems). For each strain, hiaNm was amplified in three independent PCR reactions using primers HiaNm5'A2: 5'-CCAAACCCCGATTTAACC-3' (SEQ ID NO 26) and HiaNm3'A: 5'-AATCGCCACCCTTCCCTTC-3' (SEQ ID NO 27), as indicated on FIG. 1, and corresponding to ntp 230-247 and 2114-2097 of SEQ ID No 1, and the resulting products purified and pooled. This was used as template for direct sequencing on both strands. Data were analysed using the GCG programs (Deveraux et al. (1984) *Nucleic Acids Research* 12, 387-395) and AssemblyLIGN (Oxford Molecular). Several oligonucleotides were generated as necessary to complete sequences. Sequences of hiaNm of 10 strains are shown in SEQ ID NOS 1, 3, 4, 6, 8, 10, 12, 14, 16, 18, and 20, and the deduced amino acid sequences of those genes are shown in SEQ ID NO 2, 5, 7, 9, 11, 13, 15, 17, 19 and 21.

Comparison of hiaNm from these strains indicated that they share 90-99% identity with hiaNm of MC58. In addition, hiaNm of MC58 is 62% and 68% homologous to hia and hsf of *Haemophilus influenzae*. However, in the strains examined, hiaNm is 1770-1800 bp long. This is markedly different from the hia and hsf, which are 3294 and 7059 bp long respectively. The predicted polypeptide of hiaNm, HiaNm, also exhibits homology to several other bacterial proteins, including AIDA-I, the adhesin involved in diffuse adherence of the diarrhoeagenic *Escherichia coli* strain 2787 (O126:H27), HMW1, another *Haemophilus* adhesin, UspA1, a high molecular weight protein of *Moraxella catarrthalis*, and SepA involved in tissue invasion of *Shigella flexneri* (Benz, I. and Schmidt, M. A., 1992, *Molecular Microbiology* 6:1539-1546, Barenkamp, S. J. and Leininger, E. 1992, *Infection and Immunity* 60: 1302-1313, Aebi, C. et. al 1997, *Infection and Immunity* 65: 4367-4377, Benjelloun-Touimi, Z et al 1995, *Molecular Microbiology* 17:123-135). Homology to these (and several other proteins) occurs over the first fifty amino acids of HiaNm. Analysis of this sequence reveals the presence of a predicted signal sequence, with cleavage sites at amino acid 50 in all HiaNm sequences examined. Such long signal sequences are common to proteins located in the outer membrane of Gram-negative bacteria (Henderson, I et al, 1998, *Trends in Microbiology* 6: 370-8). The proteins mentioned above to which the first fifty amino acids of HiaNm is homologous are all members of the "autotransporter" outer-membrane protein family (Henderson, I, supra). This strongly suggests that HiaNm is located in the outer membrane of *N. meningitidis*.

Example 3

Southern Blot Analysis

Southern blot analysis was performed using standard techniques (Sambrook et al., supra, Ausubel et al., supra). Briefly, genomic DNA was prepared from 70 strains of *N. meningitidis* of several serogroups, restriction digested and separated electrophoretically on an agarose gel prior to capillary transfer to a nylon membrane. These membranes were hybridized with a labeled probe. The probe used corresponded to ntp 276-2054 of SEQ ID NO 1, encompassing the entire open reading frame of hiaNm of strain MC58. This was labeled with DIG (dioxygenin) according to manufacturer's instructions (Boehringer Mannheim). Stringent washes were performed (two washes of 5 minutes at 22° C. in 2×SSC/0.1% SDS followed by two washes of 30 minutes, 68° C., 0.2×SSC/0.1% SDS). Hybridization was detected colorimetrically using nitro-blue-tetrazolium/bromo-chloryl-indolyl-phosphate (NBT/BCIP) as recommended by the manufacturer. Signals were detected in all strains examined. (FIG. 2 for example). In addition to the prototypic strain MC58, the following strains were investigated:—

TABLE 3

| Strain Name | Source | Sero-group |
|---|---|---|
| PMC 3 (J1079) | 2[A] | A |
| PMC17 (K874) | 2 | A |
| PMC 20 ((H79) | 2 | A |
| PMC23 (K750) | 2 | A |
| PMC 12 (K852) | 2 | B |
| PMC 13 (K859) | 2 | B |
| PMC 16 (K873) | 2 | B |
| PMC 24 (K782) | 2 | B |
| PMC 25 (K791) | 2 | B |
| PMC 27 (K816) | 2 | B |
| PMC 28 (K837) | 2 | B |
| BZ10 | 1[B] | B |
| BZ47 | 1 | B |
| BZ83 | 1 | B |
| BZ133 | 1 | B |
| BZ147 | 1 | B |
| BZ163 | 1 | B |
| BZ169 | 1 | B |
| BZ198 | 1 | B |
| BZ232 | 1 | B |
| NG3/88 | 1 | B |
| NG4/88 | 1 | B |
| NG6/88 | 1 | B |
| EG327 | 1 | B |
| EG329 | 1 | B |
| DK353 | 1 | B |
| 179/82 | 1 | B |
| 66/84 | 1 | B |
| DK24 | 1 | B |
| NGH36 | 1 | B |
| H38 | 1 | B |
| H41 | 1 | B |

TABLE 3-continued

| Strain Name | Source | Serogroup |
|---|---|---|
| NGE28 | 1 | B |
| NGE30 | 1 | B |
| NGP20 | 1 | B |
| NGF26 | 1 | B |
| NGG40 | 1 | B |
| H15 | 1 | B |
| SWZ107 | 1 | B |
| 528 | 1 | B |
| 2970 | 1 | B |
| 1000 | 1 | B |
| MPJB28 | 3[C] | B |
| MPJB56 | 3 | B |
| MPJB88 | 3 | B |
| MPJB157 | 3 | B |
| MPJB328 | 3 | B |
| MPJB627 | 3 | B |
| MPJB820 | 3 | B |
| MPJB945 | 3 | B |
| PMC 8 (K157) | 2 | C |
| PMC 9 (K497) | 2 | C |
| PMC 11 (K848) | 2 | C |
| PMC 14 (K860) | 2 | C |
| PMC 18 (K879) | 2 | C |
| PMC 21 (K656) | 2 | C |
| PMC 29 (K841) | 2 | C |
| MPJC05 | 3 | C |
| MPJC14 | 3 | C |
| MPJC154 | 3 | C |
| MPJC302 | 3 | C |
| MPJC379 | 3 | C |
| PMC19 | 2 | W |
| MPJW025 | 3 | W |
| PMC 1 (J603) | 2 | X |
| PMC 6 (K131) | 2 | X |
| PMC 10 (K526) | 2 | Y |
| PMC 22 (K685) | 2 | Y |
| PMC 26 (K810) | 2 | Y |
| PMC 2 ((J1049) | 2 | Z |

[A]World Health Organization Collaborating Centre for Reference and Research on Meningococci, Oslo, Norway
[B]Public Health Laboratory Service Meningococcal Reference Laboratory, Manchester, UK
[C]Brisbane Hospitals, now in strain collection of M. P. Jennings, Department of Microbiology, University of Queensland, Brisbane, Australia.

Example 4

Expression and Partial Purification of MBP-HiaNm

A plasmid vector was constructed which permitted the expression of a protein consisting of a fusion of Maltose Binding Protein and HiaNm (MBP-HiaNm). The plasmid pHiaMBP was generated by amplifying hiaNm from MC58 using primers HiaNm-MBPA 5'-GGTCGCGGATCCAT-GAACAAAATATACCGCAT-3' (SEQ ID NO 24) and HiaNm-MBPB 5'-TCACCCAAGCTTAAGCCCTTAC-CACTGATAAC-3' (SEQ ID NO 25). These primers encompass the start and stop codons of hiaNm of N. meningitidis strain MC58 and engineered restriction sites for ease of cloning. Plasmid restriction maps and positions of oligonucleotides are shown in FIG. 1. The resultant PCR product was ligated into BamHI/HindIII restriction digested plasmid pMALC2 (New England Biolabs), and the resultant plasmid, pHiaMBP (See FIG. 1) reintroduced to E. coli strain DH5α. This E. coli strain containing pHiaMBP was induced to express the HiaNm-MBP fusion protein under conditions recommended by the manufacturer (New England Biolabs). Cell extracts from cultures containing pHiAMBP were separated by 10% SDS-PAGE, and the fusion protein was partially purified by elution using the Mini-Gel Electro-eluter (Bio-Rad) according to manufacturer's instructions. Fractions containing the HiaNm-MBP fusion protein were detected by Western blot using rabbit anti-MBP sera (New England Biolabs). The purity of the HiaNm-MBP fusion protein was determined by SDS-PAGE followed by Coomassie staining, and the amount of recovered protein estimated by BCA assay (Sigma) or absorbance at a wavelength of 280 nm.

Example 5

Generation of Polyclonal Sera

The partially purified HiaNm-MBP fusion protein obtained in Example 4 was used to generate polyclonal sera in rabbits. Samples of eluted HiaNmMBP fusion protein were dialyzed against sterile phosphate buffered saline pH 7.4, (PBS) (Sigma). This was then mixed with adjuvant (MPL+TDM+CWS, Sigma), at a concentration of 50-150 µg/mL and inoculated at two weekly intervals into two New Zealand White rabbits. Blood was taken from these rabbits. Serum was extracted by clotting at room temperature for one hour followed by overnight incubation at 4° C. before centrifugation at 4000×rpm at 4° C. The supernatant was removed and re-centrifuged. Serum was stored in aliquots at −80° C. Sera obtained were used in bactericidal assays and Western blots (see below).

Figure 4:
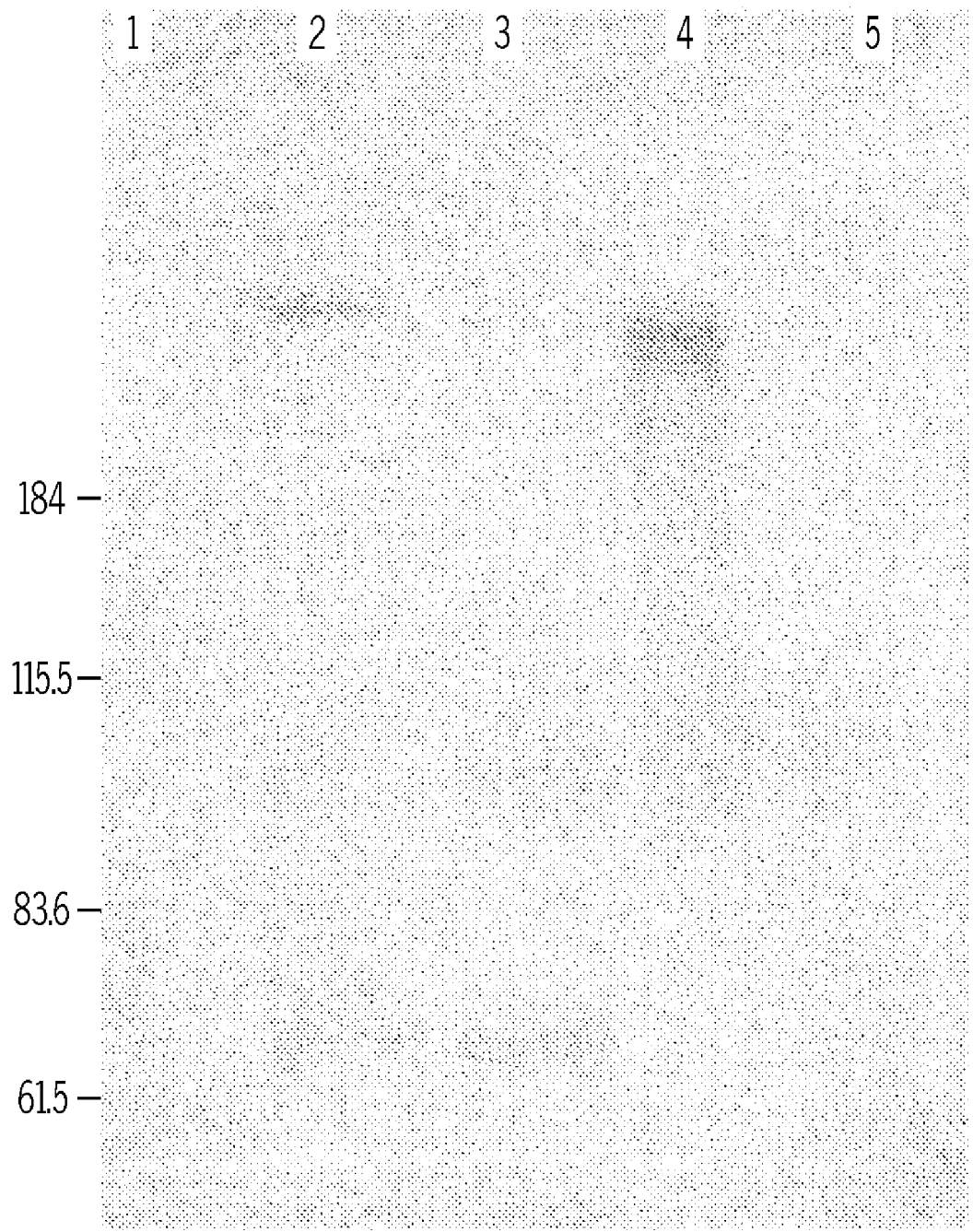
FIG. 4 is a western blot of MC58 and MC58ΔHiaNm proteins incubated with rabbit immune sera. Lane 1; molecular weight standards indicated in kDa, Lane 2 total cellular protein of MC58, Lane 3 total cellular protein of MC58ΔHiaNm Lane 4, OMC preparation of MC58, Lane 5 OMC preparation of MC58ΔHiaNm, each lane contained 50 μL of protein suspension of $A_{280}$=3.75.
Figure 5:
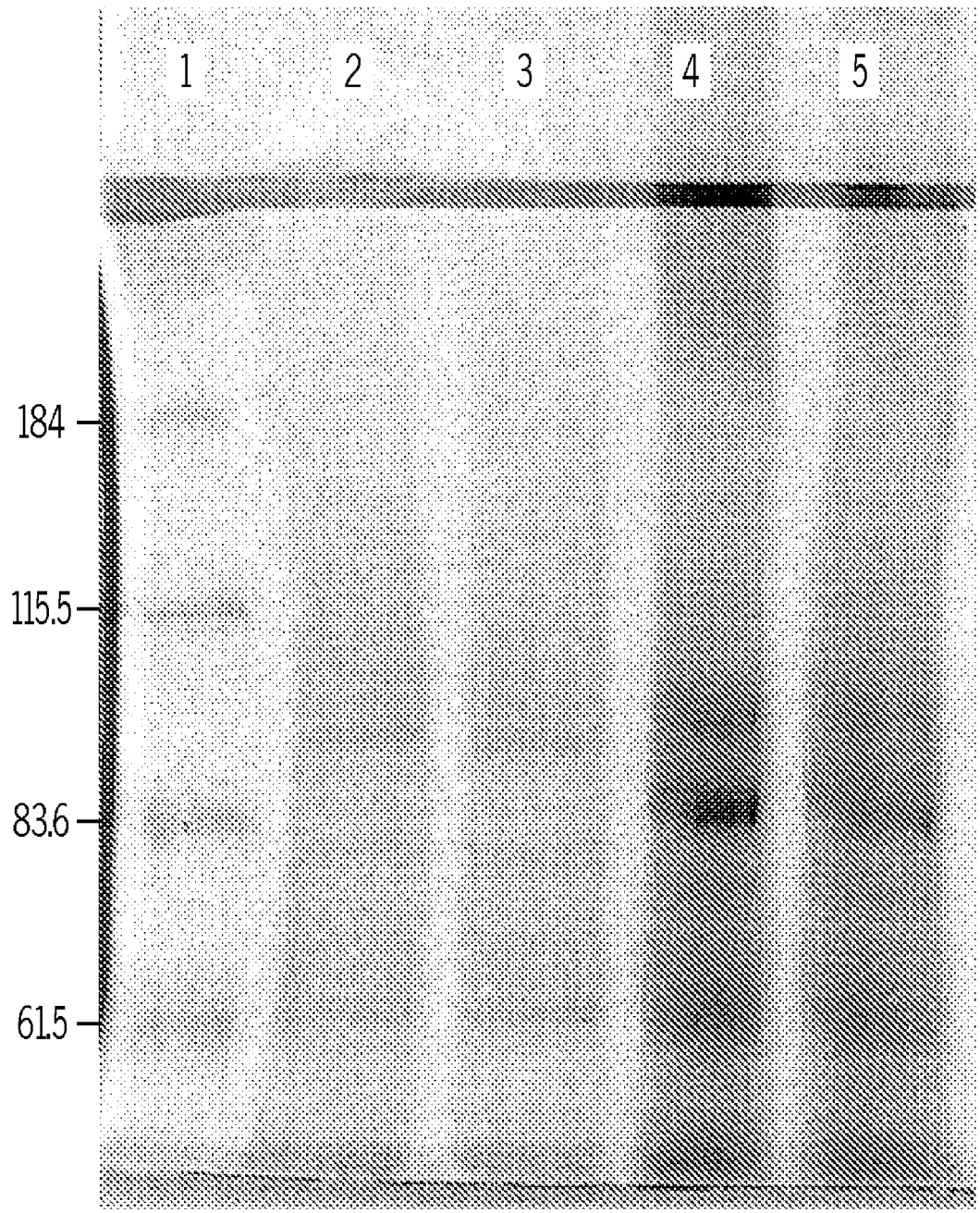
FIG. 5 shows a Coomassie stained gel run in parallel to the gel that was Western blotted in FIG. 4. Lanes are the same as for FIG. 4.

To test the specificity of the sera obtained, Western blot analysis was undertaken. Briefly, proteins of N. meningitidis strains MC58 and MC58ΔHianm were separated electrophoretically on SDS-PAGE before electrophoretic transfer to nitrocellulose membrane using a Semi-Dry Blotter (BioRad). These were then incubated sequentially with sera and alkaline-phosphatase-conjugated anti-Rabbit IgG (Sigma) before colorimetric detection with NBT/BCIP (Sigma). These experiments demonstrated that antibodies were elicited by the HiaNm-MBP fusion protein, which were specific for, and detected a band in, MC58 but not in MC58ΔHiaNm (see FIG. 4). The predicted molecular weight of the deduced polypeptide of HiaNm is 62.3 kDa. The band detected by the sera migrates at an apparent MW in excess of 150 kDa. At least three of the homologous "autotransporter" proteins reported in the literature also display such anomalous migration: the high molecular weight outer membrane proteins UspA1 and UspA2 of Moraxella catarrhalis have predicted molecular weights of 62.5 kDa and 88.3 kDa respectively but migrate at 85 kDa and 120 kDa, respectively and as the UspA complex at between 350 kDa and 720 kDa (Aebi, C. et al., 1997, Infection and Immunity, 65: 4367-4377, Klingman, K. L. and Murphy, T. F., 1994, Infection and Immunity, 62: 1150-1155). Similarly, Hia of Haemophilus influenzae has a predicted molecular weight of 116 kDa but when expressed in a phage, Hia migrates at greater than 200 kDa (Barenkamp, S. and St. Geme III, J. 1996 Molecular Microbiology 19: 1215-1233).

In order to confirm that HiaNm is associated with the outer membrane of N. meningitidis, outer membrane complexes (omc) were prepared, essentially as previously described (van der Ley, P. et al, 1991, Infection and Immunity, 59:2963-71). Briefly, bacteria were grown overnight on Brain Heart Infusion agar (Acumedia Manufacturer's Inc) supplemented with 10% heated horse blood BHI plates, resuspended in 10 mM Tris pH 8.0 and heat killed, before sonication to disrupt the membrane. Cellular debris were removed by centrifugation at 10,000×g (rcf, relative centrifugal force), and the supernatant recentrifuged at 50,000×g. This pellet was resuspended in 1% sarkosyl/10 mM Tris pH8.4 and centrifuged at 10,000×g. The supernatant was centrifuged at 75,000×g and the pellet resuspended in Tris pH 8.4, before quantification spectrophotometrically at a wavelength of 280 nm. An aliquot of the sarkosyl-insoluble fraction, which contains outer membrane proteins, (50 μl of $A_{280}$=3.75) was subjected to SDS-PAGE and Western blotted as described above. The results, shown in FIG. 4 demonstrate that reactivity with the anti-HiaNmMBP antisera is observed with wild type MC58, but not with MC58ΔHiaNm, in which hiaNm has been inactivated. The increase in reactivity with the anti-HiaMBP sera observed between whole cell samples, and the omc samples containing the same amount of total protein, in MC58 cultures is consistent with the membrane association of HiaNm.

Example 6

Bactericidal Assay

To determine whether the anti-HiaMBP antisera contained bactericidal antibodies specific for HiaNm, bactericidal assays were performed with wild type MC58 and MC58ΔHiaNm. This assay was performed by a modification of the method described by Hoogerhout et. al. (1995, *Infection and Immunity*, 63: 3473-3478). Briefly, MC58 and MC58ΔHiaNm were grown overnight on BHI plates at 37° C. in 5% $CO_2$. Bacteria from this overnight culture were subcultured under the same conditions for 4-6 hours before suspension in 1 mL PBS. Numbers of bacteria were estimated by lysis of a sample in 0.2N NaOH/1% SDS and absorbance at a wavelength of 260 nm, where $A_{260}$=1=$10^9$ cfu/mL. The bacterial suspension was adjusted to approximately $10^5$ cfu/mL in PBS. Rabbit sera to be tested was heat inactivated at 56° C. for 45 minutes. Serum from four-week-old, New Zealand White rabbits was pooled and used as a source of complement (Central Animal Breeding House, University of Queensland). The assay was carried out in sterile polystyrene flat-bottomed 96 well microtitre plate. The total volume in each well was 24 μL: 12 μL of twofold serially diluted serum in PBS and 6 μL of bacterial suspension (containing between 300-900 bacteria). Sera and bacteria were incubated at room temperature for 10 minutes before addition of 6 μL of 80% complement in PBS (final concentration 20% vol/vol). Controls were a) PBS, bacteria and complement, b) PBS, bacteria and serum. After addition of all components and mixing, a 7 μL aliquot from each control well was spread on a BHI plate. The microtitre plate was then incubated at 37° C. in 5% $CO_2$ for 60 minutes. After this incubation, a 7 μL aliquot from each well was spread on BHI plates. All BHI plates were then incubated for 14-18 hours at 37° C. in 5% $CO_2$, and bacterial colonies counted. Serum bactericidal killing is reported as the highest reciprocal dilution at which at least 90% of bacteria were killed. Serum used was from the same rabbit and the same test bleed as used for Western blot experiments as reported in Example 5 above. These experiments consistently demonstrated reduced titers (approximately 3 fold, Table 4) of killing against MC58ΔHiaNm in comparison to the wild type strain, MC58, indicating that the anti-HiaMBP antisera contained bactericidal antibodies specific for HiaNm.

TABLE 4

| STRAIN | TITRE[a] |
|---|---|
| MC58 | 12 (+/−4.6) |
| MC58ΔHiaNm | 3.5 (+/−1) |

[a]Mean of four independent experiments

DISCUSSION

Repetitive DNA has been associated with virulence determinants in some pathogenic bacteria. Southern blots using such a repetitive DNA motif revealed the presence of at least three loci which contained this motif in *N. meningitidis* strain MC58 (Peak, I. et al., 1996, *FEMS Microbiology Letters*, 137:109-114). These genes were cloned and sequence analysis of two of these repeat associated loci (nmrep2 and nmrep3) revealed open reading frames of approximately 670 amino acids (Jennings, M. et al, 1995, *Microbial Pathogenesis*, 19: 391-407, Peak, I. et al, *Microbial Pathogenesis*, in press). These exhibited homology to each other and homology to the carboxyl-terminal of the adhesin AIDA-I of *E. coli*. AIDA-I is 1286 amino acids long. The carboxyl-terminal region constitutes a putative outer membrane transport domain and the amino-terminal domain of the mature protein constitutes the adhesin domain. The amino-terminal domain crosses the membrane through the putative transport domain and is designated the passenger domain.

As Nmep2 and Nmep3 share sequence homology with the transporter domain of AIDA-I, they are thought to form membrane pores. Nmrep2 and Nmrep3 are approximately half the size of AIDA-I, and are homologous to the membrane-spanning domain of AIDA-I. We hypothesized that there existed in *N. meningitidis* a locus with homology to the amino-terminal domain of AIDA-I. We searched for such a homologue in the data from the project to sequence *N. meningitidis* strain MC58¢3 (TIGR, supra) and found one region with homology to a gene designated AIDA-I in *Haemophilus influenzae* strain Rd (HI1732) because of its homology to AIDA-I of *E. coli*, (Fleischmann et. al., 1995 *Science* 269:496-512,). In view of the homologies noted above, the applicants decided to investigate further.

The gene was initially isolated by PCR amplification of the DNA corresponding to the 471 base pair fragment; named gnmaa84r, from *N. meningitidis* MC58 3 and the sequence was confirmed. Further PCR experiments enabled larger fragments to be amplified. These were cloned and sequence analysis undertaken as shown in FIG. 1. The gene exhibited homology to the amino-terminal region of AIDA-I of *E. coli* and we designated it aida3, as it represented the third AIDA-I homologue in *N. meningitidis* (with nmrep2 and nmrep3). Since then, the discovery of two further genes, hia and hsf from *H. influenzae* has been published (Barenkamp, S. and St. Geme III, J. 1996 *Molecular Microbiology* 19: 1215-1233, St. Geme III, J. et al, 1996, *Journal of Bacteriology* 178: 6281-6287), to which aida3 is more similar. We have therefore re-designated this gene hiaNm. (HI1732, the *H. influenzae* gene first identified as an homologue of AIDA-I has also been re-designated hia in light of the reports of Barenkamp and St. Geme III).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing, from the scope of the present invention. All such modifications and changes are intended to be included within the scope of the appendant claims.

This application claims priority to GB No. 9726398.2, filed Dec. 12, 1997, which is hereby incorporated by reference.

The invention claimed is:

1. An isolated polypeptide comprising a member selected from the group consisting of (a) the amino acid sequence SEQ ID NO:2 or SEQ ID NO:21; and (b) an immunogenic fragment of at least 15 contiguous amino acids of SEQ ID NO:2 or SEQ ID NO:21; wherein the immunogenic fragment, when administered to a subject in a suitable composition which can include an adjuvant, or a suitable carrier coupled to the polypeptide, induces an antibody or T-cell mediated immune response that recognizes the isolated polypeptide SEQ ID NO:2 or SEQ ID NO:21.

2. An isolated polypeptide comprising a member selected from the group consisting of (a) the amino acid sequence SEQ ID NO:2 or SEQ ID NO:21; and (b) an immunogenic fragment of at least 10 contiguous amino acids of SEQ ID NO:2 or SEQ ID NO:21; wherein the immunogenic fragment, when administered to a subject in a suitable composition which can include an adjuvant, or a suitable carrier coupled to the polypeptide, induces an antibody or T-cell mediated immune response to the isolated polypeptide SEQ ID NO:2 or SEQ ID NO:21.

3. An isolated polypeptide comprising a member selected from the group consisting of (a) the amino acid sequence SEQ ID NO:2 or SEQ ID NO:21; and (b) an immunogenic fragment of at least 20 contiguous amino acids of SEQ ID NO:2 or SEQ ID NO:21; wherein the immunogenic fragment, when administered to a subject in a suitable composition which can include an adjuvant, or a suitable carrier coupled to the polypeptide, induces an antibody or T-cell mediated immune response to the isolated polypeptide SEQ ID NO:2 or SEQ ID NO:21.

4. The isolated polypeptide of claim 1, wherein the polypeptide is a fragment and induces an antibody response when administered to the subject.

5. The isolated polypeptide of claim 2, wherein the polypeptide is a fragment and induces an antibody response when administered to the subject.

6. The isolated polypeptide of claim 3, wherein the polypeptide is a fragment and induces an antibody response when administered to the subject.

7. An isolated polypeptide comprising a member selected from the group consisting of (a) the amino acid sequence SEQ ID NO:2 or SEQ ID NO:21; and (b) an immunogenic fragment of at least 15 contiguous amino acids of SEQ ID NO:2 or SEQ ID NO:21; wherein the immunogenic fragment, when administered to a subject elicits an immune response against the isolated polypeptide SEQ ID NO:2 or SEQ ID NO:21.

8. An isolated polypeptide comprising a member selected from the group consisting of (a) the amino acid sequence SEQ ID NO:2 or SEQ ID NO:21; and (b) an immunogenic fragment of at least 10 contiguous amino acids of SEQ ID NO:2 or SEQ ID NO:21; wherein the immunogenic fragment, when administered to a subject elicits an immune response against the isolated polypeptide SEQ ID NO:2 or SEQ ID NO:21.

9. An isolated polypeptide comprising a member selected from the group consisting of (a) the amino acid sequence SEQ ID NO:2 or SEQ ID NO:21; and (b) an immunogenic fragment of at least 20 contiguous amino acids of SEQ ID NO:2 or SEQ ID NO:21; wherein the immunogenic fragment, when administered to a subject elicits an immune response against the isolated polypeptide SEQ ID NO:2 or SEQ ID NO:21.

* * * * *

UNITED STATES PATENT AND TRADEMARK OFFICE
CERTIFICATE OF CORRECTION

PATENT NO. : 8,034,358 B2
APPLICATION NO. : 11/776709
DATED : October 11, 2011
INVENTOR(S) : Ian Richard Anselm Peak et al.

It is certified that error appears in the above-identified patent and that said Letters Patent is hereby corrected as shown below:

In the drawings, Fig. 7 should be replaced with the corrected Fig. 7 as shown on the attached pages 1, and 2.

```
FIG. 7 cont'd 201                                                    250
eg329    TLLNTGATTN  VTNDNVTDDE  KKRAASVKDV  LNAGWNIKGV  KPGTTA..SD
pmc21    TLLNTGATTN  VTNDNVTDDE  KKRAASVKDV  LNAGWNIKGV  KPGTTA..SD
HiaNm    TLLNTGATTN  VTNDNVTDDE  KKRAASVKDV  LNAGWNIKGV  KPGTTA..SD
   h15   TLLNTGATTN  VTNDNVTDDE  KKRAASVKDV  LNAGWNIKGV  KPGTTA..SD
  BZ10   TLLNTGATTN  VTNDNVTDDE  KKRAASVKDV  LNAGWNIKGV  KPGTTA..SD
 bz198   TLLNTGATTN  VTNDNVTDDE  KKRAASVKDV  LNAGWNIKGV  KPGTTA..SD
 eg327   TLLNTGATTN  VTNDNVTDDE  KKRAASVKDV  LNAGWNIKGV  KPGTTA..SD
   h38   TLLNTGATTN  VTNDNVTDDK  KKRAASVKDV  LNAGWNIKGV  KPGTTA..SD
   h41   MLLNTGATTN  VTNDNVTDDE  KKRAASVKDV  LNAGWNIKGV  KPGTTA..SD
   p20   TLAGSSASHV  DAGNQSTHY.  .TRAASIKDV  LNAGWNIKGV  KTGSTTGQSE 251                                                    300
eg329    NVDFVRTYDT  VEFLSADTKT  TTVNVESKDN  GKKTEVKIGA  KTSVIKEKDG
pmc21    NVDFVRTYDT  VEFLSADTKT  TTVNVESKDN  GKKTEVKIGA  KTSVIKEKDG
HiaNm    NVDFVRTYDT  VEFLSADTKT  TTVNVESKDN  GKKTEVKIGV  KTSVIKEKDG
   h15   NVDFVRTYDT  VEFLSADTKT  TTVNVESKDN  GKKTEVKIGA  KTSVIKEKDG
  BZ10   NVDFVRTYDT  VEFLSADTKT  TTVNVESKDN  GKRTEVKIGA  KTSVIKEKDG
 bz198   NVDFVRTYDT  VEFLSADTKT  TTVNVESKDN  GKKTEVKIGA  KTSVIKEKDG
 eg327   NVDFVRTYDT  VEFLSADTKT  TTVNVESKDN  GKRTEVKIGA  KTSVIKEKDG
   h38   NVDFVHTYDT  VEFLSADTKT  TTVNVESKDN  GKRTEVKIGA  KTSVIKEKDG
   h41   NVDFVRTYDT  VEFLSADTKT  TTVNVESKDN  GKKTEVKIGA  KTSVIKEKDG
   p20   NVDFVRTYDT  VEFLSADTKT  TTVNVESKDN  GKRTEVKIGA  KTSVIKEKDG
```

Signed and Sealed this
Tenth Day of April, 2012

David J. Kappos
*Director of the United States Patent and Trademark Office*

```
         301                                                            350
eg329    KLVTGKDKGE NGSSTDEGEG LVTAKEVIDA VNKAGWRMKT TTANGQTGQA
pmc21    KLVTGKDKGE NGSSTDEGEG LVTAKEVIDA VNKAGWRMKT TTANGQTGQA
HiaNm    KLVTGKDKGE NGSSTDEGEG LVTAKEVIDA VNKAGWRMKT TTANGQTGQA
  h15    KLVTGKGKDE NGSSTDEGEG LVTAKEVIDA VNKAGWRMKT TTANGQTGQA
 BZ10    KLVTGKGKGE NGSSTDEGEG LVTAKEVIDA VNKAGWRMKT TTANGQTGQA
bz198    KLVTGKGKDE NGSSTDEGEG LVTAKEVIDA VNKAGWRMKT TTANGQTGQA
eg327    KLVTGKDKGE NDSSTDKGEG LVTAKEVIDA VNKAGWRMKT TTANGQTGQA
  h38    KLVTGKGKGE NGSSTDEGEG LVTAKEVIDA VNKAGWRMKT TTANGQTGQA
  h41    KLVTGKGKGE NGSSTDEGEG LVTAKEVIDA VNKAGWRMKT TTANGQTGQA
  p20    KLVTGKGKGE NGSSTDEGEG LVTAKEVIDA VNKAGWRMKT TTANGQTGQA 351                                                            400
eg329    DKFETVTSGT NVTFASGKGT TATVSKDDQG NITVMYDVNV GDALNVNQLQ
pmc21    DKFETVTSGT NVTFASGKGT TATVSKDDQG NITVMYDVNV GDALNVNQLQ
HiaNm    DKFETVTSGT NVTFASGKGT TATVSKDDQG NITVMYDVNV GDALNVNQLQ
  h15    DKFETVTSGT KVTFASGNGT TATVSKDDQG NITVKYDVNV GDALNVNQLQ
 BZ10    DKFETVTSGT KVTFASGNGT TATVSKDDQG NITVKYDVNV GDALNVNQLQ
bz198    DKFETVTSGT NVTFASGKGT TATVSKDDQG NITVKYDVNV GDALNVNQLQ
eg327    DKFETVTSGT NVTFASGKGT TATVSKDDQG NITVMYDVNV GDALNVNQLQ
  h38    DKFETVTSGT NVTFASGKGT TATVSKDDQG NITVKYDVNV GDALNVNQLQ
  h41    DKFETVTSGT KVTFASGNGT TATVSKDDQG NITVKYDVNV GDALNVNQLQ
  p20    DKFETVTSGT KVTFASGNGT TATVSKDDQG NITVKYDVNV GDALNVNQLQ
```

SEQUENCE LISTING

<160> NUMBER OF SEQ ID NOS: 34

<210> SEQ ID NO 1
<211> LENGTH: 2308
<212> TYPE: DNA
<213> ORGANISM: Neisseria meningitidis
<220> FEATURE:
<221> NAME/KEY: CDS
<222> LOCATION: (276)..(2054)

<400> SEQUENCE: 1

```
gaaaaaccac aggaatttat cagcaaaaac agaaacccca ccgccgtcat tcccgcaaaa      60
gcgggaatcc agaccgtcg gcacggaaaa cttaccgaat aaaacagttt ccttagattc      120
cacgtcccag attcccgcct tcgcggggaa tgacgagatt ttaagttggg ggaatttatc      180
agaaaacccc caaccccaa aaacggggcg gatgccgcac catccgcccc caaaccccga      240
tttaaccatt caaacaaacc aaagaaaaa acaaa atg aac aaa ata tac cgc          293
                                      Met Asn Lys Ile Tyr Arg
                                        1               5 atc att tgg aat agt gcc ctc aat gcc tgg gtc gtc gta tcc gag ctc        341
Ile Ile Trp Asn Ser Ala Leu Asn Ala Trp Val Val Val Ser Glu Leu
         10                  15                  20 aca cgc aac cac acc aaa cgc gcc tcc gca acc gtg aag acc gcc gta        389
Thr Arg Asn His Thr Lys Arg Ala Ser Ala Thr Val Lys Thr Ala Val
     25                  30                  35 ttg gcg aca ctg ttg ttt gca acg gtt cag gca agt gct aac aat gaa        437
Leu Ala Thr Leu Leu Phe Ala Thr Val Gln Ala Ser Ala Asn Asn Glu
 40                  45                  50 aga cca aga aag aaa gat tta tat tta gac ccc gta caa cgc act gtt        485
Arg Pro Arg Lys Lys Asp Leu Tyr Leu Asp Pro Val Gln Arg Thr Val
 55                  60                  65                  70 gcc gtg ttg ata gtc aat tcc gat aaa gaa ggc acg gga gaa aaa gaa        533
Ala Val Leu Ile Val Asn Ser Asp Lys Glu Gly Thr Gly Glu Lys Glu
                 75                  80                  85 aaa gta gaa gaa aat tca gat tgg gca gta tat ttc aac gag aaa gga        581
Lys Val Glu Glu Asn Ser Asp Trp Ala Val Tyr Phe Asn Glu Lys Gly
             90                  95                 100 gta cta aca gcc aga gaa atc acc ctc aaa gcc ggc gac aac ctg aaa        629
Val Leu Thr Ala Arg Glu Ile Thr Leu Lys Ala Gly Asp Asn Leu Lys
         105                 110                 115 atc aaa caa aac ggc aca aac ttc acc tac tcg ctg aaa aaa gac ctc        677
Ile Lys Gln Asn Gly Thr Asn Phe Thr Tyr Ser Leu Lys Lys Asp Leu
     120                 125                 130 aca gat ctg acc agt gtt gga act gaa aaa tta tcg ttt agc gca aac        725
Thr Asp Leu Thr Ser Val Gly Thr Glu Lys Leu Ser Phe Ser Ala Asn
135                 140                 145                 150 ggc aat aaa gtc aac atc aca agc gac acc aaa ggc ttg aat ttt gcg        773
Gly Asn Lys Val Asn Ile Thr Ser Asp Thr Lys Gly Leu Asn Phe Ala
                 155                 160                 165 aaa gaa acg gct ggg acg aac ggc gac acc acg gtt cat ctg aac ggt        821
Lys Glu Thr Ala Gly Thr Asn Gly Asp Thr Thr Val His Leu Asn Gly
             170                 175                 180 att ggt tcg act ttg acc gat acg ctg ctg aat acc gga gcg acc aca        869
Ile Gly Ser Thr Leu Thr Asp Thr Leu Leu Asn Thr Gly Ala Thr Thr
         185                 190                 195 aac gta acc aac gac aac gtt acc gat gac gag aaa aaa cgt gcg gca        917
Asn Val Thr Asn Asp Asn Val Thr Asp Asp Glu Lys Lys Arg Ala Ala
     200                 205                 210 agc gtt aaa gac gta tta aac gct ggc tgg aac att aaa ggc gtt aaa        965
Ser Val Lys Asp Val Leu Asn Ala Gly Trp Asn Ile Lys Gly Val Lys
```

```
Ser Val Lys Asp Val Leu Asn Ala Gly Trp Asn Ile Lys Gly Val Lys
215             220                 225                 230 ccc ggt aca aca gct tcc gat aac gtt gat ttc gtc cgc act tac gac    1013
Pro Gly Thr Thr Ala Ser Asp Asn Val Asp Phe Val Arg Thr Tyr Asp
                    235                 240                 245 aca gtc gag ttc ttg agc gca gat acg aaa aca acg act gtt aat gtg    1061
Thr Val Glu Phe Leu Ser Ala Asp Thr Lys Thr Thr Thr Val Asn Val
            250                 255                 260 gaa agc aaa gac aac ggc aag aaa acc gaa gtt aaa atc ggt gtg aag    1109
Glu Ser Lys Asp Asn Gly Lys Lys Thr Glu Val Lys Ile Gly Val Lys
        265                 270                 275 act tct gtt att aaa gaa aaa gac ggt aag ttg gtt act ggt aaa gac    1157
Thr Ser Val Ile Lys Glu Lys Asp Gly Lys Leu Val Thr Gly Lys Asp
    280                 285                 290 aaa ggc gag aat ggt tct tct aca gac gaa ggc gaa ggc tta gtg act    1205
Lys Gly Glu Asn Gly Ser Ser Thr Asp Glu Gly Glu Gly Leu Val Thr
295                 300                 305                 310 gca aaa gaa gtg att gat gca gta aac aag gct ggt tgg aga atg aaa    1253
Ala Lys Glu Val Ile Asp Ala Val Asn Lys Ala Gly Trp Arg Met Lys
                315                 320                 325 aca aca acc gct aat ggt caa aca ggt caa gct gac aag ttt gaa acc    1301
Thr Thr Thr Ala Asn Gly Gln Thr Gly Gln Ala Asp Lys Phe Glu Thr
            330                 335                 340 gtt aca tca ggc aca aat gta acc ttt gct agt ggt aaa ggt aca act    1349
Val Thr Ser Gly Thr Asn Val Thr Phe Ala Ser Gly Lys Gly Thr Thr
        345                 350                 355 gcg act gta agt aaa gat gat caa ggc aac atc act gtt atg tat gat    1397
Ala Thr Val Ser Lys Asp Asp Gln Gly Asn Ile Thr Val Met Tyr Asp
    360                 365                 370 gta aat gtc ggc gat gcc cta aac gtc aat cag ctg caa aac agc ggt    1445
Val Asn Val Gly Asp Ala Leu Asn Val Asn Gln Leu Gln Asn Ser Gly
375                 380                 385                 390 tgg aat ttg gat tcc aaa gcg gtt gca ggt tct tcg ggc aaa gtc atc    1493
Trp Asn Leu Asp Ser Lys Ala Val Ala Gly Ser Ser Gly Lys Val Ile
                395                 400                 405 agc ggc aat gtt tcg ccg agc aag gga aag atg gat gaa acc gtc aac    1541
Ser Gly Asn Val Ser Pro Ser Lys Gly Lys Met Asp Glu Thr Val Asn
            410                 415                 420 att aat gcc ggc aac aac atc gag att acc cgc aac ggt aaa aat atc    1589
Ile Asn Ala Gly Asn Asn Ile Glu Ile Thr Arg Asn Gly Lys Asn Ile
        425                 430                 435 gac atc gcc act tcg atg acc ccg cag ttt tcc agc gtt tcg ctc ggc    1637
Asp Ile Ala Thr Ser Met Thr Pro Gln Phe Ser Ser Val Ser Leu Gly
    440                 445                 450 gcg ggg gcg gat gcg ccc act ttg agc gtg gat ggg gac gca ttg aat    1685
Ala Gly Ala Asp Ala Pro Thr Leu Ser Val Asp Gly Asp Ala Leu Asn
455                 460                 465                 470 gtc ggc agc aag aag gac aac aaa ccc gtc cgc att acc aat gtc gcc    1733
Val Gly Ser Lys Lys Asp Asn Lys Pro Val Arg Ile Thr Asn Val Ala
                475                 480                 485 ccg ggc gtt aaa gag ggg gat gtt aca aac gtc gca caa ctt aaa ggc    1781
Pro Gly Val Lys Glu Gly Asp Val Thr Asn Val Ala Gln Leu Lys Gly
            490                 495                 500 gtg gcg caa aac ttg aac aac cgc atc gac aat gtg gac ggc aac gcg    1829
Val Ala Gln Asn Leu Asn Asn Arg Ile Asp Asn Val Asp Gly Asn Ala
        505                 510                 515 cgt gcg ggc atc gcc caa gcg att gca acc gca ggt ctg gtt cag gcg    1877
Arg Ala Gly Ile Ala Gln Ala Ile Ala Thr Ala Gly Leu Val Gln Ala
    520                 525                 530 tat ttg ccc ggc aag agt atg atg gcg atc ggc ggc act tat cgc        1925
```

```
Tyr Leu Pro Gly Lys Ser Met Met Ala Ile Gly Gly Thr Tyr Arg
535                 540                 545                 550 ggc gaa gcc ggt tac gcc atc ggc tac tcc agt att tcc gac ggc gga    1973
Gly Glu Ala Gly Tyr Ala Ile Gly Tyr Ser Ser Ile Ser Asp Gly Gly
                555                 560                 565 aat tgg att atc aaa ggc acg gct tcc ggc aat tcg cgc ggc cat ttc    2021
Asn Trp Ile Ile Lys Gly Thr Ala Ser Gly Asn Ser Arg Gly His Phe
            570                 575                 580 ggt gct tcc gca tct gtc ggt tat cag tgg taa gggctttatc gcctgtctgc  2074
Gly Ala Ser Ala Ser Val Gly Tyr Gln Trp
        585                 590 tgttgggaca ggcggaaggt ttgaagggaa gggtggcgat ttgccgcctg agacctttgc  2134
aaaatccccc caaatccccc taaattccca ccaagacatt tagggatttt ctcatgagca  2194
ccttcttccg gcaaccgcg caagccatga ttgccaaaca catcaaccgt ttcccgctat   2254
tgaagttgga ccaagtgatt gattggcagc cgatcgagca gtacctgaac cgtc        2308

<210> SEQ ID NO 2
<211> LENGTH: 592
<212> TYPE: PRT
<213> ORGANISM: Neisseria meningitidis

<400> SEQUENCE: 2

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Arg Pro Arg Lys Lys Asp Leu Tyr Leu Asp
        50                  55                  60

Pro Val Gln Arg Thr Val Ala Val Leu Ile Val Asn Ser Asp Lys Glu
65                  70                  75                  80

Gly Thr Gly Glu Lys Glu Lys Val Gly Glu Asn Ser Asp Trp Ala Val
                85                  90                  95

Tyr Phe Asn Glu Lys Gly Val Leu Thr Ala Arg Glu Ile Thr Leu Lys
                100                 105                 110

Ala Gly Asp Asn Leu Lys Ile Lys Gln Asn Gly Thr Asn Phe Thr Tyr
            115                 120                 125

Ser Leu Lys Lys Asp Leu Thr Asp Leu Thr Ser Val Gly Thr Glu Lys
130                 135                 140

Leu Ser Phe Ser Ala Asn Gly Asn Lys Val Asn Ile Thr Ser Asp Thr
145                 150                 155                 160

Lys Gly Leu Asn Phe Ala Lys Glu Thr Ala Gly Thr Asn Gly Asp Thr
                165                 170                 175

Thr Val His Leu Asn Gly Ile Gly Ser Thr Leu Thr Asp Thr Leu Leu
            180                 185                 190

Asn Thr Gly Ala Thr Thr Asn Val Thr Asn Asp Asn Val Thr Asp Asp
        195                 200                 205

Glu Lys Lys Arg Ala Ala Ser Val Lys Asp Val Leu Asn Ala Gly Trp
    210                 215                 220

Asn Ile Lys Gly Val Lys Pro Gly Thr Thr Ala Ser Asp Asn Val Asp
225                 230                 235                 240

Phe Val Arg Thr Tyr Asp Thr Val Glu Phe Leu Ser Ala Asp Thr Lys
                245                 250                 255

Thr Thr Thr Val Asn Val Glu Ser Lys Asp Asn Gly Lys Lys Thr Glu
```

```
            260              265              270
Val Lys Ile Gly Val Lys Thr Ser Val Ile Lys Glu Lys Asp Gly Lys
            275              280              285
Leu Val Thr Gly Lys Asp Lys Gly Glu Asn Gly Ser Ser Thr Asp Glu
            290              295              300
Gly Glu Gly Leu Val Thr Ala Lys Glu Val Ile Asp Ala Val Asn Lys
305             310              315              320
Ala Gly Trp Arg Met Lys Thr Thr Ala Asn Gly Gln Thr Gly Gln
            325              330              335
Ala Asp Lys Phe Glu Thr Val Thr Ser Gly Thr Asn Val Thr Phe Ala
            340              345              350
Ser Gly Lys Gly Thr Thr Ala Thr Val Ser Lys Asp Asp Gln Gly Asn
            355              360              365
Ile Thr Val Met Tyr Asp Val Asn Gly Asp Ala Leu Asn Val Asn
            370              375              380
Gln Leu Gln Asn Ser Gly Trp Asn Leu Asp Ser Lys Ala Val Ala Gly
385             390              395              400
Ser Ser Gly Lys Val Ile Ser Gly Asn Val Ser Pro Ser Lys Gly Lys
            405              410              415
Met Asp Glu Thr Val Asn Ile Asn Ala Gly Asn Asn Ile Glu Ile Thr
            420              425              430
Arg Asn Gly Lys Asn Ile Asp Ile Ala Thr Ser Met Thr Pro Gln Phe
            435              440              445
Ser Ser Val Ser Leu Gly Ala Gly Ala Asp Ala Pro Thr Leu Ser Val
            450              455              460
Asp Gly Asp Ala Leu Asn Val Gly Ser Lys Lys Asp Asn Lys Pro Val
465             470              475              480
Arg Ile Thr Asn Val Ala Pro Gly Val Lys Glu Gly Asp Val Thr Asn
            485              490              495
Val Ala Gln Leu Lys Gly Val Ala Gln Asn Leu Asn Asn Arg Ile Asp
            500              505              510
Asn Val Asp Gly Asn Ala Arg Ala Gly Ile Ala Gln Ala Ile Ala Thr
            515              520              525
Ala Gly Leu Val Gln Ala Tyr Leu Pro Gly Lys Ser Met Met Ala Ile
            530              535              540
Gly Gly Gly Thr Tyr Arg Gly Glu Ala Gly Tyr Ala Ile Gly Tyr Ser
545             550              555              560
Ser Ile Ser Asp Gly Gly Asn Trp Ile Ile Lys Gly Thr Ala Ser Gly
            565              570              575
Asn Ser Arg Gly His Phe Gly Ala Ser Ala Ser Val Gly Tyr Gln Trp
            580              585              590

<210> SEQ ID NO 3
<211> LENGTH: 1779
<212> TYPE: DNA
<213> ORGANISM: Neisseria meningitidis

<400> SEQUENCE: 3
atgaacaaaa tataccgcat catttggaat agtgccctca atgcctgggt cgtcgtatcc      60
gagctcacac gcaaccacac caaacgcgcc tccgcaaccg tgaagaccgc cgtattggcg     120
acactgttgt ttgcaacggt tcaggcaagt gctaacaatg aaagaccaag aagaaagat     180 ttatatttag accccgtaca acgcactgtt gccgtgttga tagtcaattc cgataaagaa     240
ggcacgggag aaaagaaaa agtagaagaa aattcagatt gggcagtata tttcaacgag     300
```

-continued

| | |
|---|---|
| aaaggagtac taacagccag agaaatcacc ctcaaagccg gcgacaacct gaaaatcaaa | 360 |
| caaaacggca caaacttcac ctactcgctg aaaaaagacc tcacagatct gaccagtgtt | 420 |
| ggaactgaaa aattatcgtt tagcgcaaac ggcaataaag tcaacatcac aagcgacacc | 480 |
| aaaggcttga attttgcgaa agaaacggct gggacgaacg gcgacaccac ggttcatctg | 540 |
| aacggtattg gttcgacttt gaccgatacg ctgctgaata ccggagcgac cacaaacgta | 600 |
| accaacgaca acgttaccga tgacgagaaa aaacgtgcgg caagcgttaa agacgtatta | 660 |
| aacgctggct ggaacattaa aggcgttaaa cccggtacaa cagcttccga taacgttgat | 720 |
| ttcgtccgca cttacgacac agtcgagttc ttgagcgcag atacgaaaac aacgactgtt | 780 |
| aatgtggaaa gcaaagacaa cggcaagaaa accgaagtta aaatcggtgt gaagacttct | 840 |
| gttattaaag aaaaagacgg taagttggtt actggtaaag acaaaggcga gaatggttct | 900 |
| tctacagacg aaggcgaagg cttagtgact gcaaagaag tgattgatgc agtaaacaag | 960 |
| gctggttgga gaatgaaaac aacaaccgct aatggtcaaa caggtcaagc tgacaagttt | 1020 |
| gaaaccgtta catcaggcac aaatgtaacc tttgctagtg gtaaaggtac aactgcgact | 1080 |
| gtaagtaaag atgatcaagg caacatcact gttatgtatg atgtaaatgt cggcgatgcc | 1140 |
| ctaaacgtca atcagctgca aaacagcggt tggaatttgg attccaaagc ggttgcaggt | 1200 |
| tcttcgggca aagtcatcag cggcaatgtt tcgccgagca agggaaagat ggatgaaacc | 1260 |
| gtcaacatta atgccggcaa caacatcgag attacccgca acggtaaaaa tatcgacatc | 1320 |
| gccacttcga tgaccccgca gttttccagc gtttcgctcg gcgcggggc ggatgcgccc | 1380 |
| actttgagcg tggatgggga cgcattgaat gtcggcagca agaaggacaa caaacccgtc | 1440 |
| cgcattacca atgtcgcccc gggcgttaaa gaggggatg ttacaaacgt cgcacaactt | 1500 |
| aaaggcgtgg cgcaaaactt gaacaaccgc atcgacaatg tggacggcaa cgcgcgtgcg | 1560 |
| ggcatcgccc aagcgattgc aaccgcaggt ctggttcagg cgtatttgcc cggcaagagt | 1620 |
| atgatggcga tcggcggcgg cacttatcgc ggcgaagccg ttacgccat cggctactcc | 1680 |
| agtatttccg acggcggaaa ttggattatc aaaggcacgg cttccggcaa ttcgcgcggc | 1740 |
| catttcggtg cttccgcatc tgtcggttat cagtggtaa | 1779 |

<210> SEQ ID NO 4
<211> LENGTH: 1797
<212> TYPE: DNA
<213> ORGANISM: Neisseria meningitidis
<220> FEATURE:
<221> NAME/KEY: CDS
<222> LOCATION: (1)..(1797)

<400> SEQUENCE: 4

| | |
|---|---|
| atg aac aaa ata tcc cgc atc att tgg aat agt gcc ctc aat gcc tgg<br>Met Asn Lys Ile Ser Arg Ile Ile Trp Asn Ser Ala Leu Asn Ala Trp<br>1               5                   10                  15 | 48 |
| gtc gtc gta tcc gag ctc aca cgc aac cac acc aaa cgc gcc tcc gca<br>Val Val Val Ser Glu Leu Thr Arg Asn His Thr Lys Arg Ala Ser Ala<br>            20                  25                  30 | 96 |
| acc gtg gcg acc gcc gta ttg gcg aca ctg ttg ttt gca acg gtt cag<br>Thr Val Ala Thr Ala Val Leu Ala Thr Leu Leu Phe Ala Thr Val Gln<br>        35                  40                  45 | 144 |
| gcg aat gct acc gat gac gac gat tta tat tta gaa ccc gta caa cgc<br>Ala Asn Ala Thr Asp Asp Asp Asp Leu Tyr Leu Glu Pro Val Gln Arg<br>    50                  55                  60 | 192 |
| act gct gtc gtg ttg agc ttc cgt tcc gat aaa gaa ggc acg gga gaa<br>Thr Ala Val Val Leu Ser Phe Arg Ser Asp Lys Glu Gly Thr Gly Glu<br>65                  70                  75                  80 | 240 |

```
aaa gaa ggt aca gaa gat tca aat tgg gca gta tat ttc gac gag aaa    288
Lys Glu Gly Thr Glu Asp Ser Asn Trp Ala Val Tyr Phe Asp Glu Lys
             85                  90                  95 aga gta cta aaa gcc gga gca atc acc ctc aaa gcc ggc gac aac ctg    336
Arg Val Leu Lys Ala Gly Ala Ile Thr Leu Lys Ala Gly Asp Asn Leu
            100                 105                 110 aaa atc aaa caa aac acc aat gaa aac acc aat gaa aac acc aat gac    384
Lys Ile Lys Gln Asn Thr Asn Glu Asn Thr Asn Glu Asn Thr Asn Asp
        115                 120                 125 agt agc ttc acc tac tcc ctg aaa aaa gac ctc aca gat ctg acc agt    432
Ser Ser Phe Thr Tyr Ser Leu Lys Lys Asp Leu Thr Asp Leu Thr Ser
    130                 135                 140 gtt gaa act gaa aaa tta tcg ttt ggc gca aac ggt aat aaa gtc aac    480
Val Glu Thr Glu Lys Leu Ser Phe Gly Ala Asn Gly Asn Lys Val Asn
145                 150                 155                 160 atc aca agc gac acc aaa ggc ttg aat ttt gcg aaa gaa acg gct ggg    528
Ile Thr Ser Asp Thr Lys Gly Leu Asn Phe Ala Lys Glu Thr Ala Gly
                165                 170                 175 acg aac ggc gac ccc acg gtt cat ctg aac ggt atc ggt tcg act ttg    576
Thr Asn Gly Asp Pro Thr Val His Leu Asn Gly Ile Gly Ser Thr Leu
            180                 185                 190 acc gat acg ctg ctg aat acc gga gcg acc aca aac gta acc aac gac    624
Thr Asp Thr Leu Leu Asn Thr Gly Ala Thr Thr Asn Val Thr Asn Asp
        195                 200                 205 aac gtt acc gat gac gag aaa aaa cgt gcg gca agc gtt aaa gac gta    672
Asn Val Thr Asp Asp Glu Lys Lys Arg Ala Ala Ser Val Lys Asp Val
    210                 215                 220 tta aac gca ggc tgg aac att aaa ggc gtt aaa ccc ggt aca aca gct    720
Leu Asn Ala Gly Trp Asn Ile Lys Gly Val Lys Pro Gly Thr Thr Ala
225                 230                 235                 240 tcc gat aac gtc gat ttc gtc cgc act tac gac aca gtc gag ttc ttg    768
Ser Asp Asn Val Asp Phe Val Arg Thr Tyr Asp Thr Val Glu Phe Leu
                245                 250                 255 agc gca gat acg aaa aca acg act gtt aat gtg gaa agc aaa gac aac    816
Ser Ala Asp Thr Lys Thr Thr Thr Val Asn Val Glu Ser Lys Asp Asn
            260                 265                 270 ggc aag aga acc gaa gtt aaa atc ggt gcg aag act tct gtt att aaa    864
Gly Lys Arg Thr Glu Val Lys Ile Gly Ala Lys Thr Ser Val Ile Lys
        275                 280                 285 gaa aaa gac ggt aag ttg gtt act ggt aaa ggc aaa ggc gag aat ggt    912
Glu Lys Asp Gly Lys Leu Val Thr Gly Lys Gly Lys Gly Glu Asn Gly
    290                 295                 300 tct tct aca gac gaa ggc gaa ggc tta gtg act gca aaa gaa gtg att    960
Ser Ser Thr Asp Glu Gly Glu Gly Leu Val Thr Ala Lys Glu Val Ile
305                 310                 315                 320 gat gca gta aac aag gct ggt tgg aga atg aaa aca aca acc gct aat    1008
Asp Ala Val Asn Lys Ala Gly Trp Arg Met Lys Thr Thr Thr Ala Asn
                325                 330                 335 ggt caa aca ggt caa gct gac aag ttt gaa acc gtt aca tca ggc aca    1056
Gly Gln Thr Gly Gln Ala Asp Lys Phe Glu Thr Val Thr Ser Gly Thr
            340                 345                 350 aaa gta acc ttt gct agt ggt aat ggt aca act gcg act gta agt aaa    1104
Lys Val Thr Phe Ala Ser Gly Asn Gly Thr Thr Ala Thr Val Ser Lys
        355                 360                 365 gat gat caa ggc aac atc act gtt aag tat gat gta aat gtc ggc gat    1152
Asp Asp Gln Gly Asn Ile Thr Val Lys Tyr Asp Val Asn Val Gly Asp
    370                 375                 380 gcc cta aac gtc aat cag ctg caa aac agc ggt tgg aat ttg gat tcc    1200
Ala Leu Asn Val Asn Gln Leu Gln Asn Ser Gly Trp Asn Leu Asp Ser
385                 390                 395                 400
```

```
aaa gcg gtt gca ggt tct tcg ggc aaa gtc atc agc ggc aat gtt tcg    1248
Lys Ala Val Ala Gly Ser Ser Gly Lys Val Ile Ser Gly Asn Val Ser
                405                 410                 415 ccg agc aag gga aag atg gat gaa acc gtc aac att aat gcc ggc aac    1296
Pro Ser Lys Gly Lys Met Asp Glu Thr Val Asn Ile Asn Ala Gly Asn
            420                 425                 430 aac atc gag att acc cgc aac ggc aaa aat atc gac atc gcc act tcg    1344
Asn Ile Glu Ile Thr Arg Asn Gly Lys Asn Ile Asp Ile Ala Thr Ser
        435                 440                 445 atg acc ccg caa ttt tcc agc gtt tcg ctc ggc gcg ggg gcg gat gcg    1392
Met Thr Pro Gln Phe Ser Ser Val Ser Leu Gly Ala Gly Ala Asp Ala
    450                 455                 460 ccc act tta agc gtg gat gac gag ggc gcg ttg aat gtc ggc agc aag    1440
Pro Thr Leu Ser Val Asp Asp Glu Gly Ala Leu Asn Val Gly Ser Lys
465                 470                 475                 480 gat gcc aac aaa ccc gtc cgc att acc aat gtc gcc ccg ggc gtt aaa    1488
Asp Ala Asn Lys Pro Val Arg Ile Thr Asn Val Ala Pro Gly Val Lys
                485                 490                 495 gag ggg gat gtt aca aac gtc gca caa ctt aaa ggt gtg gcg caa aac    1536
Glu Gly Asp Val Thr Asn Val Ala Gln Leu Lys Gly Val Ala Gln Asn
            500                 505                 510 ttg aac aac cgc atc gac aat gtg gac ggc aac gcg cgc gcg ggt atc    1584
Leu Asn Asn Arg Ile Asp Asn Val Asp Gly Asn Ala Arg Ala Gly Ile
        515                 520                 525 gcc caa gcg att gca acc gca ggt ttg gct cag gcc tat ttg ccc ggc    1632
Ala Gln Ala Ile Ala Thr Ala Gly Leu Ala Gln Ala Tyr Leu Pro Gly
    530                 535                 540 aag agt atg atg gcg atc ggc ggc ggt act tat cgc ggc gaa gcc ggt    1680
Lys Ser Met Met Ala Ile Gly Gly Gly Thr Tyr Arg Gly Glu Ala Gly
545                 550                 555                 560 tac gcc atc ggc tac tcg agc att tct gac act ggg aat tgg gtt atc    1728
Tyr Ala Ile Gly Tyr Ser Ser Ile Ser Asp Thr Gly Asn Trp Val Ile
                565                 570                 575 aag ggc acg gct tcc ggc aat tcg cgc ggt cat ttc ggt act tcc gca    1776
Lys Gly Thr Ala Ser Gly Asn Ser Arg Gly His Phe Gly Thr Ser Ala
            580                 585                 590 tct gtc ggt tat cag tgg taa                                        1797
Ser Val Gly Tyr Gln Trp
        595

<210> SEQ ID NO 5
<211> LENGTH: 598
<212> TYPE: PRT
<213> ORGANISM: Neisseria meningitidis

<400> SEQUENCE: 5

Met Asn Lys Ile Ser Arg Ile Ile Trp Asn Ser Ala Leu Asn Ala Trp
1               5                   10                  15

Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Asn Ala Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
```

-continued

```
                100                 105                 110
Lys Ile Lys Gln Asn Thr Asn Glu Asn Thr Asn Glu Asn Thr Asn Asp
            115                 120                 125

Ser Ser Phe Thr Tyr Ser Leu Lys Lys Asp Leu Thr Asp Leu Thr Ser
            130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
            165                 170                 175

Thr Asn Gly Asp Pro Thr Val His Leu Asn Gly Ile Gly Ser Thr Leu
            180                 185                 190

Thr Asp Thr Leu Leu Asn Thr Gly Ala Thr Thr Asn Val Thr Asn Asp
            195                 200                 205

Asn Val Thr Asp Asp Glu Lys Lys Arg Ala Ala Ser Val Lys Asp Val
            210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
            245                 250                 255

Ser Ala Asp Thr Lys Thr Thr Thr Val Asn Val Glu Ser Lys Asp Asn
            260                 265                 270

Gly Lys Arg Thr Glu Val Lys Ile Gly Ala Lys Thr Ser Val Ile Lys
            275                 280                 285

Glu Lys Asp Gly Lys Leu Val Thr Gly Lys Lys Gly Glu Asn Gly
            290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Ala Asn
            325                 330                 335

Gly Gln Thr Gly Gln Ala Asp Lys Phe Glu Thr Val Thr Ser Gly Thr
            340                 345                 350

Lys Val Thr Phe Ala Ser Gly Asn Gly Thr Thr Ala Thr Val Ser Lys
            355                 360                 365

Asp Asp Gln Gly Asn Ile Thr Val Lys Tyr Asp Val Asn Val Gly Asp
            370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
            405                 410                 415

Pro Ser Lys Gly Lys Met Asp Glu Thr Val Asn Ile Asn Ala Gly Asn
            420                 425                 430

Asn Ile Glu Ile Thr Arg Asn Gly Lys Asn Ile Asp Ile Ala Thr Ser
            435                 440                 445

Met Thr Pro Gln Phe Ser Ser Val Ser Leu Gly Ala Gly Ala Asp Ala
            450                 455                 460

Pro Thr Leu Ser Val Asp Asp Glu Gly Ala Leu Asn Val Gly Ser Lys
465                 470                 475                 480

Asp Ala Asn Lys Pro Val Arg Ile Thr Asn Val Ala Pro Gly Val Lys
            485                 490                 495

Glu Gly Asp Val Thr Asn Val Ala Gln Leu Lys Gly Val Ala Gln Asn
            500                 505                 510

Leu Asn Asn Arg Ile Asp Asn Val Asp Gly Asn Ala Arg Ala Gly Ile
            515                 520                 525
```

```
Ala Gln Ala Ile Ala Thr Ala Gly Leu Ala Gln Ala Tyr Leu Pro Gly
        530             535             540

Lys Ser Met Met Ala Ile Gly Gly Gly Thr Tyr Arg Gly Glu Ala Gly
545             550             555             560

Tyr Ala Ile Gly Tyr Ser Ser Ile Ser Asp Thr Gly Asn Trp Val Ile
            565             570             575

Lys Gly Thr Ala Ser Gly Asn Ser Arg Gly His Phe Gly Thr Ser Ala
        580             585             590

Ser Val Gly Tyr Gln Trp
        595

<210> SEQ ID NO 6
<211> LENGTH: 1785
<212> TYPE: DNA
<213> ORGANISM: Neisseria meningitidis
<220> FEATURE:
<221> NAME/KEY: CDS
<222> LOCATION: (1)..(1785)

<400> SEQUENCE: 6 atg aac aaa ata tac cgc atc att tgg aat agt gcc ctc aat gcc tgg      48
Met Asn Lys Ile Tyr Arg Ile Ile Trp Asn Ser Ala Leu Asn Ala Trp
1               5                   10                  15 gtc gtc gta tcc gag ctc aca cgc aac cac acc aaa cgc gcc tcc gca      96
Val Val Val Ser Glu Leu Thr Arg Asn His Thr Lys Arg Ala Ser Ala
            20                  25                  30 acc gtg gcg acc gcc gta ttg gcg aca ctg ttg ttt gca acg gtt cag     144
Thr Val Ala Thr Ala Val Leu Ala Thr Leu Leu Phe Ala Thr Val Gln
        35                  40                  45 gcg aat gct acc gat gac gac gat tta tat tta gaa ccc gta caa cgc     192
Ala Asn Ala Thr Asp Asp Asp Asp Leu Tyr Leu Glu Pro Val Gln Arg
    50                  55                  60 act gct gtc gtg ttg agc ttc cgt tcc gat aaa gaa ggc acg gga gaa     240
Thr Ala Val Val Leu Ser Phe Arg Ser Asp Lys Glu Gly Thr Gly Glu
65                  70                  75                  80 aaa gaa ggt aca gaa gat tca aat tgg gca gta tat ttc gac gag aaa     288
Lys Glu Gly Thr Glu Asp Ser Asn Trp Ala Val Tyr Phe Asp Glu Lys
                85                  90                  95 aga gta cta aaa gcc gga gca atc acc ctc aaa gcc ggc gac aac ctg     336
Arg Val Leu Lys Ala Gly Ala Ile Thr Leu Lys Ala Gly Asp Asn Leu
            100                 105                 110 aaa atc aaa caa aac acc aat gaa aac acc aat gac agt agc ttc acc     384
Lys Ile Lys Gln Asn Thr Asn Glu Asn Thr Asn Asp Ser Ser Phe Thr
        115                 120                 125 tac tcc ctg aaa aaa gac ctc aca gat ctg acc agt gtt gaa act gaa     432
Tyr Ser Leu Lys Lys Asp Leu Thr Asp Leu Thr Ser Val Glu Thr Glu
    130                 135                 140 aaa tta tcg ttt ggc gca aac ggt aat aaa gtc aac atc aca agc gac     480
Lys Leu Ser Phe Gly Ala Asn Gly Asn Lys Val Asn Ile Thr Ser Asp
145                 150                 155                 160 acc aaa ggc ttg aat ttt gcg aaa gaa acg gct ggg acg aac ggc gac     528
Thr Lys Gly Leu Asn Phe Ala Lys Glu Thr Ala Gly Thr Asn Gly Asp
                165                 170                 175 ccc acg gtt cat ctg aac ggt atc ggt tcg act ttg acc gat acg ctg     576
Pro Thr Val His Leu Asn Gly Ile Gly Ser Thr Leu Thr Asp Thr Leu
            180                 185                 190 ctg aat acc gga gcg acc aca aac gta acc aac gac aac gtt acc gat     624
Leu Asn Thr Gly Ala Thr Thr Asn Val Thr Asn Asp Asn Val Thr Asp
        195                 200                 205 gac gag aaa aaa cgt gcg gca agc gtt aaa gac gta tta aac gca ggc     672
Asp Glu Lys Lys Arg Ala Ala Ser Val Lys Asp Val Leu Asn Ala Gly
```

```
              210                 215                 220
tgg aac att aaa ggc gtt aaa ccc ggt aca aca gct tcc gat aac gtt     720
Trp Asn Ile Lys Gly Val Lys Pro Gly Thr Thr Ala Ser Asp Asn Val
225                 230                 235                 240 gat ttc gtc cgc act tac gac aca gtc gag ttc ttg agc gca gat acg     768
Asp Phe Val Arg Thr Tyr Asp Thr Val Glu Phe Leu Ser Ala Asp Thr
                245                 250                 255 aaa aca acg act gtt aat gtg gaa agc aaa gac aac ggc aag aaa acc     816
Lys Thr Thr Thr Val Asn Val Glu Ser Lys Asp Asn Gly Lys Lys Thr
            260                 265                 270 gaa gtt aaa atc ggt gcg aag act tct gtt att aaa gaa aaa gac ggt     864
Glu Val Lys Ile Gly Ala Lys Thr Ser Val Ile Lys Glu Lys Asp Gly
        275                 280                 285 aag ttg gtt act ggt aaa ggc aaa gac gag aat ggt tct tct aca gac     912
Lys Leu Val Thr Gly Lys Gly Lys Asp Glu Asn Gly Ser Ser Thr Asp
    290                 295                 300 gaa ggc gaa ggc tta gtg act gca aaa gaa gtg att gat gca gta aac     960
Glu Gly Glu Gly Leu Val Thr Ala Lys Glu Val Ile Asp Ala Val Asn
305                 310                 315                 320 aag gct ggt tgg aga atg aaa aca aca acc gct aat ggt caa aca ggt    1008
Lys Ala Gly Trp Arg Met Lys Thr Thr Thr Ala Asn Gly Gln Thr Gly
                325                 330                 335 caa gct gac aag ttt gaa acc gtt aca tca ggc aca aat gta acc ttt    1056
Gln Ala Asp Lys Phe Glu Thr Val Thr Ser Gly Thr Asn Val Thr Phe
            340                 345                 350 gct agt ggt aaa ggt aca act gcg act gta agt aaa gat gat caa ggc    1104
Ala Ser Gly Lys Gly Thr Thr Ala Thr Val Ser Lys Asp Asp Gln Gly
        355                 360                 365 aac atc act gtt aag tat gat gta aat gtc ggc gat gcc cta aac gtc    1152
Asn Ile Thr Val Lys Tyr Asp Val Asn Val Gly Asp Ala Leu Asn Val
    370                 375                 380 aat cag ctg caa aac agc ggt tgg aat ttg gat tcc aaa gcg gtt gca    1200
Asn Gln Leu Gln Asn Ser Gly Trp Asn Leu Asp Ser Lys Ala Val Ala
385                 390                 395                 400 ggt tct tcg ggc aaa gtc atc agc ggc aat gtt tcg ccg agc aag gga    1248
Gly Ser Ser Gly Lys Val Ile Ser Gly Asn Val Ser Pro Ser Lys Gly
                405                 410                 415 aag atg gat gaa acc gtc aac att aat gcc ggc aac aac atc gag att    1296
Lys Met Asp Glu Thr Val Asn Ile Asn Ala Gly Asn Asn Ile Glu Ile
            420                 425                 430 acc cgc aac ggt aaa aat atc gac atc gcc act tcg atg gcg ccg cag    1344
Thr Arg Asn Gly Lys Asn Ile Asp Ile Ala Thr Ser Met Ala Pro Gln
        435                 440                 445 ttt tcc agc gtt tcg ctc ggt gcg ggg gcg gat gcg ccc act ttg agc    1392
Phe Ser Ser Val Ser Leu Gly Ala Gly Ala Asp Ala Pro Thr Leu Ser
    450                 455                 460 gtg gat gac gag ggc gcg ttg aat gtc ggc agc aag gat acc aac aaa    1440
Val Asp Asp Glu Gly Ala Leu Asn Val Gly Ser Lys Asp Thr Asn Lys
465                 470                 475                 480 ccc gtc cgc att acc aat gtc gcc ccg ggc gtt aaa gag ggg gat gtt    1488
Pro Val Arg Ile Thr Asn Val Ala Pro Gly Val Lys Glu Gly Asp Val
                485                 490                 495 aca aac gtc gca caa ctt aaa ggc gtg gcg caa aac ttg aac aac cgc    1536
Thr Asn Val Ala Gln Leu Lys Gly Val Ala Gln Asn Leu Asn Asn Arg
            500                 505                 510 atc gac aat gtg gac ggc aac gcg cgt gcg ggc atc gcc caa gcg att    1584
Ile Asp Asn Val Asp Gly Asn Ala Arg Ala Gly Ile Ala Gln Ala Ile
        515                 520                 525 gca acc gca ggt cta gtt cag gcg tat ctg ccc ggc aag agt atg atg    1632
Ala Thr Ala Gly Leu Val Gln Ala Tyr Leu Pro Gly Lys Ser Met Met
```

```
                 530                 535                 540
gcg atc ggc ggc gac act tat cgc ggc gaa gcc ggt tac gcc atc ggc    1680
Ala Ile Gly Gly Asp Thr Tyr Arg Gly Glu Ala Gly Tyr Ala Ile Gly
545                 550                 555                 560 tac tca agt att tcc gac ggc gga aat tgg att atc aaa ggc acg gct    1728
Tyr Ser Ser Ile Ser Asp Gly Gly Asn Trp Ile Ile Lys Gly Thr Ala
                565                 570                 575 tcc ggc aat tcg cgc ggc cat ttc ggt gct tcc gca tct gtc ggt tat    1776
Ser Gly Asn Ser Arg Gly His Phe Gly Ala Ser Ala Ser Val Gly Tyr
                580                 585                 590 caa tgg taa                                                        1785
Gln Trp

<210> SEQ ID NO 7
<211> LENGTH: 594
<212> TYPE: PRT
<213> ORGANISM: Neisseria meningitidis

<400> SEQUENCE: 7

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Asn Ala Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
            100                 105                 110

Lys Ile Lys Gln Asn Thr Asn Glu Asn Thr Asn Asp Ser Ser Phe Thr
        115                 120                 125

Tyr Ser Leu Lys Lys Asp Leu Thr Asp Leu Thr Ser Val Glu Thr Glu
130                 135                 140

Lys Leu Ser Phe Gly Ala Asn Gly Asn Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Pro Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285

Lys Leu Val Thr Gly Lys Gly Lys Asp Glu Asn Gly Ser Ser Thr Asp
```

```
                290                 295                 300
Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
            325                 330                 335

Gln Ala Asp Lys Phe Glu Thr Val Thr Ser Gly Thr Asn Val Thr Phe
        340                 345                 350

Ala Ser Gly Lys Gly Thr Thr Ala Thr Val Ser Lys Asp Asp Gln Gly
            355                 360                 365

Asn Ile Thr Val Lys Tyr Asp Val Asn Val Gly Asp Ala Leu Asn Val
        370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
            405                 410                 415

Lys Met Asp Glu Thr Val Asn Ile Asn Ala Gly Asn Asn Ile Glu Ile
        420                 425                 430

Thr Arg Asn Gly Lys Asn Ile Asp Ile Ala Thr Ser Met Ala Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Thr Asn Lys
465                 470                 475                 480

Pro Val Arg Ile Thr Asn Val Ala Pro Gly Val Lys Glu Gly Asp Val
            485                 490                 495

Thr Asn Val Ala Gln Leu Lys Gly Val Ala Gln Asn Leu Asn Asn Arg
        500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
            565                 570                 575

Ser Gly Asn Ser Arg Gly His Phe Gly Ala Ser Ala Ser Val Gly Tyr
        580                 585                 590

Gln Trp

<210> SEQ ID NO 8
<211> LENGTH: 1785
<212> TYPE: DNA
<213> ORGANISM: Neisseria meningitidis
<220> FEATURE:
<221> NAME/KEY: CDS
<222> LOCATION: (1)..(1785)

<400> SEQUENCE: 8 atg aac aaa ata tac cgc atc att tgg aat agt gcc ctc aat gcc tgg     48
Met Asn Lys Ile Tyr Arg Ile Ile Trp Asn Ser Ala Leu Asn Ala Trp
1               5                   10                  15 gtc gcc gta tcc gag ctc aca cgc aac cac acc aaa cgc gcc tcc gca     96
Val Ala Val Ser Glu Leu Thr Arg Asn His Thr Lys Arg Ala Ser Ala
            20                  25                  30 acc gtg gcg acc gcc gta ttg gcg aca ctg ttg ttt gca acg gtt cag    144
Thr Val Ala Thr Ala Val Leu Ala Thr Leu Leu Phe Ala Thr Val Gln
        35                  40                  45
```

```
gcg agt act acc gat gac gac gat tta tat tta gaa ccc gta caa cgc      192
Ala Ser Thr Thr Asp Asp Asp Asp Leu Tyr Leu Glu Pro Val Gln Arg
     50                  55                  60 act gct gtc gtg ttg agc ttc cgt tcc gat aaa gaa ggc acg gga gaa      240
Thr Ala Val Val Leu Ser Phe Arg Ser Asp Lys Glu Gly Thr Gly Glu
 65                  70                  75                  80 aaa gaa gtt aca gaa gat tca aat tgg gga gta tat ttc gac aag aaa      288
Lys Glu Val Thr Glu Asp Ser Asn Trp Gly Val Tyr Phe Asp Lys Lys
                     85                  90                  95 gga gta cta aca gcc gga aca atc acc ctc aaa gcc ggc gac aac ctg      336
Gly Val Leu Thr Ala Gly Thr Ile Thr Leu Lys Ala Gly Asp Asn Leu
                 100                 105                 110 aaa atc aaa caa aac acc aat gaa aac acc aat gcc agt agc ttc acc      384
Lys Ile Lys Gln Asn Thr Asn Glu Asn Thr Asn Ala Ser Ser Phe Thr
             115                 120                 125 tac tcg ctg aaa aaa gac ctc aca gat ctg acc agt gtt gga act gaa      432
Tyr Ser Leu Lys Lys Asp Leu Thr Asp Leu Thr Ser Val Gly Thr Glu
 130                 135                 140 aaa tta tcg ttt agc gca aac agc aat aaa gtc aac atc aca agc gac      480
Lys Leu Ser Phe Ser Ala Asn Ser Asn Lys Val Asn Ile Thr Ser Asp
145                 150                 155                 160 acc aaa ggc ttg aat ttc gcg aaa aaa acg gct gag acc aac ggc gac      528
Thr Lys Gly Leu Asn Phe Ala Lys Lys Thr Ala Glu Thr Asn Gly Asp
                 165                 170                 175 acc acg gtt cat ctg aac ggt atc ggt tcg act ttg acc gat acg ctg      576
Thr Thr Val His Leu Asn Gly Ile Gly Ser Thr Leu Thr Asp Thr Leu
             180                 185                 190 ctg aat acc gga gcg acc aca aac gta acc aac gac aac gtt acc gat      624
Leu Asn Thr Gly Ala Thr Thr Asn Val Thr Asn Asp Asn Val Thr Asp
         195                 200                 205 gac gag aaa aaa cgt gcg gca agc gtt aaa gac gta tta aac gca ggc      672
Asp Glu Lys Lys Arg Ala Ala Ser Val Lys Asp Val Leu Asn Ala Gly
     210                 215                 220 tgg aac att aaa ggc gtt aaa ccc ggt aca aca gct tcc gat aac gtt      720
Trp Asn Ile Lys Gly Val Lys Pro Gly Thr Thr Ala Ser Asp Asn Val
225                 230                 235                 240 gat ttc gtc cgc act tac gac aca gtc gag ttc ttg agc gca gat acg      768
Asp Phe Val Arg Thr Tyr Asp Thr Val Glu Phe Leu Ser Ala Asp Thr
                 245                 250                 255 aaa aca acg act gtt aat gtg gaa agc aaa gac aac ggc aag aga acc      816
Lys Thr Thr Thr Val Asn Val Glu Ser Lys Asp Asn Gly Lys Arg Thr
             260                 265                 270 gaa gtt aaa atc ggt gcg aag act tct gtt atc aaa gaa aaa gac ggt      864
Glu Val Lys Ile Gly Ala Lys Thr Ser Val Ile Lys Glu Lys Asp Gly
         275                 280                 285 aag ttg gtt act ggt aaa gac aaa ggc gag aat gat tct tct aca gac      912
Lys Leu Val Thr Gly Lys Asp Lys Gly Glu Asn Asp Ser Ser Thr Asp
     290                 295                 300 aaa ggc gaa ggc tta gtg act gca aaa gaa gtg att gat gca gta aac      960
Lys Gly Glu Gly Leu Val Thr Ala Lys Glu Val Ile Asp Ala Val Asn
305                 310                 315                 320 aag gct ggt tgg aga atg aaa aca aca acc gct aat ggt caa aca ggt     1008
Lys Ala Gly Trp Arg Met Lys Thr Thr Thr Ala Asn Gly Gln Thr Gly
                 325                 330                 335 caa gct gac aag ttt gaa acc gtt aca tca ggc aca aat gta acc ttt     1056
Gln Ala Asp Lys Phe Glu Thr Val Thr Ser Gly Thr Asn Val Thr Phe
             340                 345                 350 gct agt ggt aaa ggt aca act gcg act gta agt aaa gat gat caa ggc     1104
Ala Ser Gly Lys Gly Thr Thr Ala Thr Val Ser Lys Asp Asp Gln Gly
         355                 360                 365
```

-continued

```
aac atc act gtt atg tat gat gta aat gtc ggc gat gcc cta aac gtc    1152
Asn Ile Thr Val Met Tyr Asp Val Asn Val Gly Asp Ala Leu Asn Val
    370             375                 380 aat cag ctg caa aac agc ggt tgg aat ttg gat tcc aaa gcg gtt gca    1200
Asn Gln Leu Gln Asn Ser Gly Trp Asn Leu Asp Ser Lys Ala Val Ala
385                 390                 395                 400 ggt tct tcg ggc aaa gtc atc agc ggc aat gtt tcg ccg agc aag gga    1248
Gly Ser Ser Gly Lys Val Ile Ser Gly Asn Val Ser Pro Ser Lys Gly
                405                 410                 415 aag atg gat gaa acc gtc aac att aat gcc ggc aac aac atc gag att    1296
Lys Met Asp Glu Thr Val Asn Ile Asn Ala Gly Asn Asn Ile Glu Ile
            420                 425                 430 acc cgc aac ggc aaa aat atc gac atc gcc act tcg atg acc ccg caa    1344
Thr Arg Asn Gly Lys Asn Ile Asp Ile Ala Thr Ser Met Thr Pro Gln
        435                 440                 445 ttt tcc agc gtt tcg ctc ggc gcg ggg gcg gat gcg ccc act tta agc    1392
Phe Ser Ser Val Ser Leu Gly Ala Gly Ala Asp Ala Pro Thr Leu Ser
    450                 455                 460 gtg gat gac gag ggc gcg ttg aat gtc ggc agc aag gat gcc aac aaa    1440
Val Asp Asp Glu Gly Ala Leu Asn Val Gly Ser Lys Asp Ala Asn Lys
465                 470                 475                 480 ccc gtc cgc att acc aat gtc gcc ccg ggc gtt aaa gag ggg gat gtt    1488
Pro Val Arg Ile Thr Asn Val Ala Pro Gly Val Lys Glu Gly Asp Val
                485                 490                 495 aca aac gtc gca caa ctt aaa ggc gtg gcg caa aac ttg aac aac cac    1536
Thr Asn Val Ala Gln Leu Lys Gly Val Ala Gln Asn Leu Asn Asn His
            500                 505                 510 atc gac aat gtg gac ggc aac gcg cgt gcg ggc atc gcc caa gcg att    1584
Ile Asp Asn Val Asp Gly Asn Ala Arg Ala Gly Ile Ala Gln Ala Ile
        515                 520                 525 gca acc gca ggt ctg gtt cag gcg tat ctg ccc ggc aag agt atg atg    1632
Ala Thr Ala Gly Leu Val Gln Ala Tyr Leu Pro Gly Lys Ser Met Met
    530                 535                 540 gcg atc ggc ggc ggc act tat cgc ggc gaa gcc ggt tat gcc atc ggc    1680
Ala Ile Gly Gly Gly Thr Tyr Arg Gly Glu Ala Gly Tyr Ala Ile Gly
545                 550                 555                 560 tac tca agc att tcc gac ggc gga aat tgg att atc aaa ggc acg gct    1728
Tyr Ser Ser Ile Ser Asp Gly Gly Asn Trp Ile Ile Lys Gly Thr Ala
                565                 570                 575 tcc ggc aat tcg cgc ggc cat ttc ggt gct tcc gca tct gtc ggt tat    1776
Ser Gly Asn Ser Arg Gly His Phe Gly Ala Ser Ala Ser Val Gly Tyr
            580                 585                 590 cag tgg taa                                                        1785
Gln Trp

<210> SEQ ID NO 9
<211> LENGTH: 594
<212> TYPE: PRT
<213> ORGANISM: Neisseria meningitidis

<400> SEQUENCE: 9

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Phe Ala Thr Val Gln
        35                  40                  45

Ala Ser Thr Thr Asp Asp Asp Leu Tyr Leu Glu Pro Val Gln Arg
    50                  55                  60
```

```
Thr Ala Val Val Leu Ser Phe Arg Ser Asp Lys Glu Gly Thr Gly Glu
 65                  70                  75                  80

Lys Glu Val Thr Glu Asp Ser Asn Trp Gly Val Tyr Phe Asp Lys Lys
                 85                  90                  95

Gly Val Leu Thr Ala Gly Thr Ile Thr Leu Lys Ala Gly Asp Asn Leu
            100                 105                 110

Lys Ile Lys Gln Asn Thr Asn Glu Asn Thr Asn Ala Ser Ser Phe Thr
        115                 120                 125

Tyr Ser Leu Lys Lys Asp Leu Thr Asp Leu Thr Ser Val Gly Thr Glu
130                 135                 140

Lys Leu Ser Phe Ser Ala Asn Ser Asn Lys Val Asn Ile Thr Ser Asp
145                 150                 155                 160

Thr Lys Gly Leu Asn Phe Ala Lys Lys Thr Ala Glu Thr Asn Gly Asp
            165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
            195                 200                 205

Asp Glu Lys Lys Arg Ala Ala Ser Val Lys Asp Val Leu Asn Ala Gly
210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Arg Thr
                260                 265                 270

Glu Val Lys Ile Gly Ala Lys Thr Ser Val Ile Lys Glu Lys Asp Gly
            275                 280                 285

Lys Leu Val Thr Gly Lys Asp Lys Gly Glu Asn Asp Ser Ser Thr Asp
290                 295                 300

Lys Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Asn Val Thr Phe
                340                 345                 350

Ala Ser Gly Lys Gly Thr Thr Ala Thr Val Ser Lys Asp Asp Gln Gly
            355                 360                 365

Asn Ile Thr Val Met Tyr Asp Val Asn Val Gly Asp Ala Leu Asn Val
            370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
                420                 425                 430

Thr Arg Asn Gly Lys Asn Ile Asp Ile Ala Thr Ser Met Thr Pro Gln
            435                 440                 445

Phe Ser Ser Val Ser Leu Gly Ala Gly Ala Asp Ala Pro Thr Leu Ser
450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495
```

```
Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
            515                 520                 525

Ala Thr Ala Gly Leu Val Gln Ala Tyr Leu Pro Gly Lys Ser Met Met
            530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 10
<211> LENGTH: 1776
<212> TYPE: DNA
<213> ORGANISM: Neisseria meningitidis
<220> FEATURE:
<221> NAME/KEY: CDS
<222> LOCATION: (1)..(1776)

<400> SEQUENCE: 10 atg aac gaa ata ttg cgc atc att tgg aat agc gcc ctc aat gcc tgg      48
Met Asn Glu Ile Leu Arg Ile Ile Trp Asn Ser Ala Leu Asn Ala Trp
1               5                   10                  15 gtc gtt gta tcc gag ctc aca cgc aac cac acc aaa cgc gcc tcc gca      96
Val Val Val Ser Glu Leu Thr Arg Asn His Thr Lys Arg Ala Ser Ala
            20                  25                  30 acc gtg aag acc gcc gta ttg gcg act ctg ttg ttt gca acg gtt cag     144
Thr Val Lys Thr Ala Val Leu Ala Thr Leu Leu Phe Ala Thr Val Gln
        35                  40                  45 gca agt gct aac aat gaa gag caa gaa gaa gat tta tat tta gac ccc     192
Ala Ser Ala Asn Asn Glu Glu Gln Glu Glu Asp Leu Tyr Leu Asp Pro
    50                  55                  60 gtg cta cgc act gtt gcc gtg ttg ata gtc aat tcc gat aaa gaa ggc     240
Val Leu Arg Thr Val Ala Val Leu Ile Val Asn Ser Asp Lys Glu Gly
65                  70                  75                  80 acg gga gaa aaa gaa aaa gta gaa gaa aat tca gat tgg gca gta tat     288
Thr Gly Glu Lys Glu Lys Val Glu Glu Asn Ser Asp Trp Ala Val Tyr
                85                  90                  95 ttc aac gag aaa gga gta cta aca gcc aga gaa atc acc ctc aaa gcc     336
Phe Asn Glu Lys Gly Val Leu Thr Ala Arg Glu Ile Thr Leu Lys Ala
            100                 105                 110 ggc gac aac ctg aaa atc aaa caa aac ggc aca aac ttc acc tac tcg     384
Gly Asp Asn Leu Lys Ile Lys Gln Asn Gly Thr Asn Phe Thr Tyr Ser
        115                 120                 125 ctg aaa aaa gac ctc aca gat ctg acc agt gtt gga act gaa aaa tta     432
Leu Lys Lys Asp Leu Thr Asp Leu Thr Ser Val Gly Thr Glu Lys Leu
    130                 135                 140 tcg ttt agc gca aac ggc aat aaa gtc aac atc aca agc gac acc aaa     480
Ser Phe Ser Ala Asn Gly Asn Lys Val Asn Ile Thr Ser Asp Thr Lys
145                 150                 155                 160 ggc ttg aat ttt gcg aaa gaa acg gct ggg acg aac ggc gac acc acg     528
Gly Leu Asn Phe Ala Lys Glu Thr Ala Gly Thr Asn Gly Asp Thr Thr
                165                 170                 175 gtt cat ctg aac ggt att ggt tcg act ttg acc gat acg ctg ctg aat     576
Val His Leu Asn Gly Ile Gly Ser Thr Leu Thr Asp Thr Leu Leu Asn
            180                 185                 190
```

```
acc gga gcg acc aca aac gta acc aac gac aac gtt acc gat gac gag     624
Thr Gly Ala Thr Thr Asn Val Thr Asn Asp Asn Val Thr Asp Asp Glu
        195                 200                 205 aaa aaa cgt gcg gca agc gtt aaa gac gta tta aac gct ggc tgg aac     672
Lys Lys Arg Ala Ala Ser Val Lys Asp Val Leu Asn Ala Gly Trp Asn
    210                 215                 220 att aaa ggc gtt aaa ccc ggt aca aca gct tcc gat aac gtt gat ttc     720
Ile Lys Gly Val Lys Pro Gly Thr Thr Ala Ser Asp Asn Val Asp Phe
225                 230                 235                 240 gtc cgc act tac gac aca gtc gag ttc ttg agc gca gat acg aaa aca     768
Val Arg Thr Tyr Asp Thr Val Glu Phe Leu Ser Ala Asp Thr Lys Thr
            245                 250                 255 acg act gtt aat gtg gaa agc aaa gac aac ggc aag aaa acc gaa gtt     816
Thr Thr Val Asn Val Glu Ser Lys Asp Asn Gly Lys Lys Thr Glu Val
        260                 265                 270 aaa atc ggt gcg aag act tct gtt att aaa gaa aaa gac ggt aag ttg     864
Lys Ile Gly Ala Lys Thr Ser Val Ile Lys Glu Lys Asp Gly Lys Leu
    275                 280                 285 gtt act ggt aaa gac aaa ggc gag aat ggt tct tct aca gac gaa ggc     912
Val Thr Gly Lys Asp Lys Gly Glu Asn Gly Ser Ser Thr Asp Glu Gly
290                 295                 300 gaa ggc tta gtg act gca aaa gaa gtg att gat gca gta aac aag gct     960
Glu Gly Leu Val Thr Ala Lys Glu Val Ile Asp Ala Val Asn Lys Ala
305                 310                 315                 320 ggt tgg aga atg aaa aca aca acc gct aat ggt caa aca ggt caa gct    1008
Gly Trp Arg Met Lys Thr Thr Thr Ala Asn Gly Gln Thr Gly Gln Ala
            325                 330                 335 gac aag ttt gaa acc gtt aca tca ggc aca aat gta acc ttt gct agt    1056
Asp Lys Phe Glu Thr Val Thr Ser Gly Thr Asn Val Thr Phe Ala Ser
        340                 345                 350 ggt aaa ggt aca act gcg act gta agt aaa gat gat caa ggc aac atc    1104
Gly Lys Gly Thr Thr Ala Thr Val Ser Lys Asp Asp Gln Gly Asn Ile
    355                 360                 365 act gtt atg tat gat gta aat gtc ggc gat gcc cta aac gtc aat cag    1152
Thr Val Met Tyr Asp Val Asn Val Gly Asp Ala Leu Asn Val Asn Gln
370                 375                 380 ctg caa aac agc ggt tgg aat ttg gat tcc aaa gcg gtt gca ggt tct    1200
Leu Gln Asn Ser Gly Trp Asn Leu Asp Ser Lys Ala Val Ala Gly Ser
385                 390                 395                 400 tcg ggc aaa gtc atc agc ggc aat gtt tcg ccg agc aag gga aag atg    1248
Ser Gly Lys Val Ile Ser Gly Asn Val Ser Pro Ser Lys Gly Lys Met
            405                 410                 415 gat gaa acc gtc aac att aat gcc ggc aac aac atc gag att acc cgc    1296
Asp Glu Thr Val Asn Ile Asn Ala Gly Asn Asn Ile Glu Ile Thr Arg
        420                 425                 430 aac ggt aaa aat atc gac atc gcc act tcg atg acc ccg cag ttt tcc    1344
Asn Gly Lys Asn Ile Asp Ile Ala Thr Ser Met Thr Pro Gln Phe Ser
    435                 440                 445 agc gtt tcg ctc ggc gcg ggg gcg gat gcg ccc act ttg agc gtg gat    1392
Ser Val Ser Leu Gly Ala Gly Ala Asp Ala Pro Thr Leu Ser Val Asp
450                 455                 460 ggg gac gca ttg aat gtc ggc agc aag aag gac aac aaa ccc gtc cgc    1440
Gly Asp Ala Leu Asn Val Gly Ser Lys Lys Asp Asn Lys Pro Val Arg
465                 470                 475                 480 att acc aat gtc gcc ccg ggc gtt aaa gag ggg gat gtt aca aac gtc    1488
Ile Thr Asn Val Ala Pro Gly Val Lys Glu Gly Asp Val Thr Asn Val
            485                 490                 495 gca caa ctt aaa ggc gtg gcg caa aac ttg aac aac cgc atc gac aat    1536
Ala Gln Leu Lys Gly Val Ala Gln Asn Leu Asn Asn Arg Ile Asp Asn
        500                 505                 510
```

```
gtg gac ggc aac gcg cgt gcg ggc atc gcc caa gcg att gca acc gca    1584
Val Asp Gly Asn Ala Arg Ala Gly Ile Ala Gln Ala Ile Ala Thr Ala
        515                 520                 525 ggt ctg gtt cag gcg tat ttg ccc ggc aag agt atg atg gcg atc ggc    1632
Gly Leu Val Gln Ala Tyr Leu Pro Gly Lys Ser Met Met Ala Ile Gly
530                 535                 540 ggc ggc act tat cgc ggc gaa gcc ggt tac gcc atc ggc tac tcc agt    1680
Gly Gly Thr Tyr Arg Gly Glu Ala Gly Tyr Ala Ile Gly Tyr Ser Ser
545                 550                 555                 560 att tcc gac ggc gga aat tgg att atc aaa ggc acg gct tcc ggc aat    1728
Ile Ser Asp Gly Gly Asn Trp Ile Ile Lys Gly Thr Ala Ser Gly Asn
                565                 570                 575 tcg cgc ggc cat ttc ggt gct tcc gca tct gtc ggt tat cag tgg taa    1776
Ser Arg Gly His Phe Gly Ala Ser Ala Ser Val Gly Tyr Gln Trp
                580                 585                 590

<210> SEQ ID NO 11
<211> LENGTH: 591
<212> TYPE: PRT
<213> ORGANISM: Neisseria meningitidis

<400> SEQUENCE: 11

Met Asn Glu Ile Leu Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Leu Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
```

-continued

```
                275                 280                 285
Val Thr Gly Lys Asp Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
            325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
            485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
            580                 585                 590
```

<210> SEQ ID NO 12
<211> LENGTH: 1797
<212> TYPE: DNA
<213> ORGANISM: Neisseria meningitidis
<220> FEATURE:
<221> NAME/KEY: CDS
<222> LOCATION: (1)..(1797)

<400> SEQUENCE: 12

```
atg aac aaa ata tac cgc atc att tgg aat agt gcc ctc aat gcc tgg      48
Met Asn Lys Ile Tyr Arg Ile Ile Trp Asn Ser Ala Leu Asn Ala Trp
1               5                   10                  15 gtc gtc gta tcc gag ctc aca cgc aac cac acc aaa cgc gcc tcc gca      96
Val Val Val Ser Glu Leu Thr Arg Asn His Thr Lys Arg Ala Ser Ala
            20                  25                  30 acc gtg gcg acc gcc gta ttg gcg aca ctg ttg ttt gca acg gtt cag     144
Thr Val Ala Thr Ala Val Leu Ala Thr Leu Leu Phe Ala Thr Val Gln
```

```
                  35                  40                  45
gcg aat gct acc gat gac gac gat tta tat tta gaa ccc gta caa cgc    192
Ala Asn Ala Thr Asp Asp Asp Asp Leu Tyr Leu Glu Pro Val Gln Arg
 50                  55                  60 act gct gtc gtg ttg agc ttc cgt tcc gat aaa gaa ggc acg gga gaa    240
Thr Ala Val Val Leu Ser Phe Arg Ser Asp Lys Glu Gly Thr Gly Glu
 65                  70                  75                  80 aaa gaa ggt aca gaa gat tca aat tgg gca gta tat ttc gac gag aaa    288
Lys Glu Gly Thr Glu Asp Ser Asn Trp Ala Val Tyr Phe Asp Glu Lys
                     85                  90                  95 aga gta cta aaa gcc gga gca atc acc ctc aaa gcc ggc gac aac ctg    336
Arg Val Leu Lys Ala Gly Ala Ile Thr Leu Lys Ala Gly Asp Asn Leu
100                 105                 110 aaa atc aaa caa aac acc aat gaa aac acc aat gaa aac acc aat gac    384
Lys Ile Lys Gln Asn Thr Asn Glu Asn Thr Asn Glu Asn Thr Asn Asp
            115                 120                 125 agt agc ttc acc tac tcc ctg aaa aaa gac ctc aca gat ctg acc agt    432
Ser Ser Phe Thr Tyr Ser Leu Lys Lys Asp Leu Thr Asp Leu Thr Ser
130                 135                 140 gtt gaa act gaa aaa tta tcg ttt ggc gca aac ggt aat aaa gtc aac    480
Val Glu Thr Glu Lys Leu Ser Phe Gly Ala Asn Gly Asn Lys Val Asn
145                 150                 155                 160 atc aca agc gac acc aaa ggc ttg aat ttt gcg aaa gaa acg gct ggg    528
Ile Thr Ser Asp Thr Lys Gly Leu Asn Phe Ala Lys Glu Thr Ala Gly
                    165                 170                 175 acg aac ggc gac ccc acg gtt cat ctg aac ggt atc ggt tcg act ttg    576
Thr Asn Gly Asp Pro Thr Val His Leu Asn Gly Ile Gly Ser Thr Leu
                180                 185                 190 acc gat acg ctg ctg aat acc gga gcg acc aca aac gta acc aac gac    624
Thr Asp Thr Leu Leu Asn Thr Gly Ala Thr Thr Asn Val Thr Asn Asp
            195                 200                 205 aac gtt acc gat gac gag aaa aaa cgt gcg gca agc gtt aaa gac gta    672
Asn Val Thr Asp Asp Glu Lys Lys Arg Ala Ala Ser Val Lys Asp Val
210                 215                 220 tta aac gca ggc tgg aac att aaa ggc gtt aaa ccc ggt aca aca gct    720
Leu Asn Ala Gly Trp Asn Ile Lys Gly Val Lys Pro Gly Thr Thr Ala
225                 230                 235                 240 tcc gat aac gtt gat ttc gtc cgc act tac gac aca gtc gag ttc ttg    768
Ser Asp Asn Val Asp Phe Val Arg Thr Tyr Asp Thr Val Glu Phe Leu
                245                 250                 255 agc gca gat acg aaa aca acg act gtt aat gtg gaa agc aaa gac aac    816
Ser Ala Asp Thr Lys Thr Thr Thr Val Asn Val Glu Ser Lys Asp Asn
                260                 265                 270 ggc aag aaa acc gaa gtt aaa atc ggt gcg aag act tct gtt att aaa    864
Gly Lys Lys Thr Glu Val Lys Ile Gly Ala Lys Thr Ser Val Ile Lys
            275                 280                 285 gaa aaa gac ggt aag ttg gtt act ggt aaa ggc aaa gac gag aat ggt    912
Glu Lys Asp Gly Lys Leu Val Thr Gly Lys Gly Lys Asp Glu Asn Gly
290                 295                 300 tct tct aca gac gaa ggc gaa ggc tta gtg act gca aaa gaa gtg att    960
Ser Ser Thr Asp Glu Gly Glu Gly Leu Val Thr Ala Lys Glu Val Ile
305                 310                 315                 320 gat gca gta aac aag gct ggt tgg aga atg aaa aca aca acc gct aat    1008
Asp Ala Val Asn Lys Ala Gly Trp Arg Met Lys Thr Thr Thr Ala Asn
                325                 330                 335 ggt caa aca ggt caa gct gac aag ttt gaa acc gtt aca tca ggc aca    1056
Gly Gln Thr Gly Gln Ala Asp Lys Phe Glu Thr Val Thr Ser Gly Thr
                340                 345                 350 aaa gta acc ttt gct agt ggt aat ggt aca act gcg act gta agt aaa    1104
Lys Val Thr Phe Ala Ser Gly Asn Gly Thr Thr Ala Thr Val Ser Lys
```

```
                355                 360                 365
gat gat caa ggc aac atc act gtt aag tat gat gta aat gtc ggc gat      1152
Asp Asp Gln Gly Asn Ile Thr Val Lys Tyr Asp Val Asn Val Gly Asp
    370                 375                 380 gcc cta aac gtc aat cag ctg caa aac agc ggt tgg aat ttg gat tcc      1200
Ala Leu Asn Val Asn Gln Leu Gln Asn Ser Gly Trp Asn Leu Asp Ser
385                 390                 395                 400 aaa gcg gtt gca ggt tct tcg ggc aaa gtc atc agc ggc aat gtt tcg      1248
Lys Ala Val Ala Gly Ser Ser Gly Lys Val Ile Ser Gly Asn Val Ser
                405                 410                 415 ccg agc aag gga aag atg gat gaa acc gtc aac att aat gcc ggc aac      1296
Pro Ser Lys Gly Lys Met Asp Glu Thr Val Asn Ile Asn Ala Gly Asn
            420                 425                 430 aac atc gag att acc cgc aac ggc aaa aat atc gac atc gcc act tcg      1344
Asn Ile Glu Ile Thr Arg Asn Gly Lys Asn Ile Asp Ile Ala Thr Ser
        435                 440                 445 atg acc ccg caa ttt tcc agc gtt tcg ctc ggc gcg ggg gcg gat gcg      1392
Met Thr Pro Gln Phe Ser Ser Val Ser Leu Gly Ala Gly Ala Asp Ala
    450                 455                 460 ccc act tta agc gtg gat gac gag ggc gcg ttg aat gtc ggc agc aag      1440
Pro Thr Leu Ser Val Asp Asp Glu Gly Ala Leu Asn Val Gly Ser Lys
465                 470                 475                 480 gat gcc aac aaa ccc gtc cgc att acc aat gtc gcc ccg ggc gtt aaa      1488
Asp Ala Asn Lys Pro Val Arg Ile Thr Asn Val Ala Pro Gly Val Lys
                485                 490                 495 gag ggg gat gtt aca aac gtc gca caa ctt aaa ggt gtg gcg caa aac      1536
Glu Gly Asp Val Thr Asn Val Ala Gln Leu Lys Gly Val Ala Gln Asn
            500                 505                 510 ttg aac aac cgc atc gac aat gtg gac ggc aac gcg cgc gcg ggt atc      1584
Leu Asn Asn Arg Ile Asp Asn Val Asp Gly Asn Ala Arg Ala Gly Ile
        515                 520                 525 gcc caa gcg att gca acc gca ggt ttg gct cag gcg tat ttg ccc ggc      1632
Ala Gln Ala Ile Ala Thr Ala Gly Leu Ala Gln Ala Tyr Leu Pro Gly
    530                 535                 540 aag agt atg atg gcg atc ggc ggc ggt act tat cgc ggc gaa gcc ggt      1680
Lys Ser Met Met Ala Ile Gly Gly Gly Thr Tyr Arg Gly Glu Ala Gly
545                 550                 555                 560 tac gcc atc ggc tac tcg agc att tct gac act ggg aat tgg gtt atc      1728
Tyr Ala Ile Gly Tyr Ser Ser Ile Ser Asp Thr Gly Asn Trp Val Ile
                565                 570                 575 aag ggc acg gct tcc ggc aat tcg cgc ggc cat ttc ggt gct tcc gca      1776
Lys Gly Thr Ala Ser Gly Asn Ser Arg Gly His Phe Gly Ala Ser Ala
            580                 585                 590 tct gtc ggt tat cag tgg taa                                          1797
Ser Val Gly Tyr Gln Trp
        595

<210> SEQ ID NO 13
<211> LENGTH: 598
<212> TYPE: PRT
<213> ORGANISM: Neisseria meningitidis

<400> SEQUENCE: 13

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Leu Phe Ala Thr Val Gln
            35                  40                  45

Ala Asn Ala Thr Asp Asp Asp Asp Leu Tyr Leu Glu Pro Val Gln Arg
```

```
                    50                  55                  60
Thr Ala Val Val Leu Ser Phe Arg Ser Asp Lys Glu Gly Thr Gly Glu
 65                  70                  75                  80

Lys Glu Gly Thr Glu Asp Ser Asn Trp Ala Val Tyr Phe Asp Glu Lys
                     85                  90                  95

Arg Val Leu Lys Ala Gly Ala Ile Thr Leu Lys Ala Gly Asp Asn Leu
                    100                 105                 110

Lys Ile Lys Gln Asn Thr Asn Glu Asn Thr Asn Glu Thr Asn Asp
                115                 120                 125

Ser Ser Phe Thr Tyr Ser Leu Lys Lys Asp Leu Thr Asp Leu Thr Ser
130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
                    165                 170                 175

Thr Asn Gly Asp Pro Thr Val His Leu Asn Gly Ile Gly Ser Thr Leu
                180                 185                 190

Thr Asp Thr Leu Leu Asn Thr Gly Ala Thr Thr Asn Val Thr Asn Asp
                195                 200                 205

Asn Val Thr Asp Asp Glu Lys Lys Arg Ala Ala Ser Val Lys Asp Val
210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
                    245                 250                 255

Ser Ala Asp Thr Lys Thr Thr Thr Val Asn Val Glu Ser Lys Asp Asn
                    260                 265                 270

Gly Lys Lys Thr Glu Val Lys Ile Gly Ala Lys Thr Ser Val Ile Lys
                275                 280                 285

Glu Lys Asp Gly Lys Leu Val Thr Gly Lys Gly Lys Asp Glu Asn Gly
290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Ala Asn
                    325                 330                 335

Gly Gln Thr Gly Gln Ala Asp Lys Phe Glu Thr Val Thr Ser Gly Thr
                340                 345                 350

Lys Val Thr Phe Ala Ser Gly Asn Gly Thr Thr Ala Thr Val Ser Lys
                355                 360                 365

Asp Asp Gln Gly Asn Ile Thr Val Lys Tyr Asp Val Asn Val Gly Asp
                370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
                    405                 410                 415

Pro Ser Lys Gly Lys Met Asp Glu Thr Val Asn Ile Asn Ala Gly Asn
                420                 425                 430

Asn Ile Glu Ile Thr Arg Asn Gly Lys Asn Ile Asp Ile Ala Thr Ser
                435                 440                 445

Met Thr Pro Gln Phe Ser Ser Val Ser Leu Gly Ala Gly Ala Asp Ala
                450                 455                 460

Pro Thr Leu Ser Val Asp Asp Glu Gly Ala Leu Asn Val Gly Ser Lys
465                 470                 475                 480
```

-continued

```
Asp Ala Asn Lys Pro Val Arg Ile Thr Asn Val Ala Pro Gly Val Lys
            485                 490                 495
Glu Gly Asp Val Thr Asn Val Ala Gln Leu Lys Gly Val Ala Gln Asn
        500                 505                 510
Leu Asn Asn Arg Ile Asp Asn Val Asp Gly Asn Ala Arg Ala Gly Ile
            515                 520                 525
Ala Gln Ala Ile Ala Thr Ala Gly Leu Ala Gln Ala Tyr Leu Pro Gly
        530                 535                 540
Lys Ser Met Met Ala Ile Gly Gly Thr Tyr Arg Gly Glu Ala Gly
545                 550                 555                 560
Tyr Ala Ile Gly Tyr Ser Ser Ile Ser Asp Thr Gly Asn Trp Val Ile
                565                 570                 575
Lys Gly Thr Ala Ser Gly Asn Ser Arg Gly His Phe Gly Ala Ser Ala
            580                 585                 590
Ser Val Gly Tyr Gln Trp
        595

<210> SEQ ID NO 14
<211> LENGTH: 1800
<212> TYPE: DNA
<213> ORGANISM: Neisseria meningitidis
<220> FEATURE:
<221> NAME/KEY: CDS
<222> LOCATION: (1)..(1800)

<400> SEQUENCE: 14 atg aac aaa ata tac cgc atc att tgg aat agt gcc ctc aat gcc tgg      48
Met Asn Lys Ile Tyr Arg Ile Ile Trp Asn Ser Ala Leu Asn Ala Trp
1               5                   10                  15 gtc gcc gta tcc gag ctc aca cgc aac cac acc aaa cgc gcc tcc gca      96
Val Ala Val Ser Glu Leu Thr Arg Asn His Thr Lys Arg Ala Ser Ala
                20                  25                  30 acc gtg aag acc gcc gta ttg gcg acg ctg ttg ttt gca acg gtt cag     144
Thr Val Lys Thr Ala Val Leu Ala Thr Leu Leu Phe Ala Thr Val Gln
            35                  40                  45 gcg aat gct acc gat gaa gat gaa gaa gaa gag tta gaa ccc gta gta     192
Ala Asn Ala Thr Asp Glu Asp Glu Glu Glu Leu Glu Pro Val Val
        50                  55                  60 cgc tct gct ctg gtg ttg caa ttc atg atc gat aaa gaa ggc aat gga     240
Arg Ser Ala Leu Val Leu Gln Phe Met Ile Asp Lys Glu Gly Asn Gly
65              70                  75                  80 gaa aac gaa tct aca gga aat ata ggt tgg agt ata tat tac gac aat     288
Glu Asn Glu Ser Thr Gly Asn Ile Gly Trp Ser Ile Tyr Tyr Asp Asn
                85                  90                  95 cac aac act cta cac ggc gca acc gtt acc ctc aaa gcc ggc gac aac     336
His Asn Thr Leu His Gly Ala Thr Val Thr Leu Lys Ala Gly Asp Asn
                100                 105                 110 ctg aaa atc aaa caa aac acc aat aaa aac acc aat gaa aac acc aat     384
Leu Lys Ile Lys Gln Asn Thr Asn Lys Asn Thr Asn Glu Asn Thr Asn
            115                 120                 125 gac agc agc ttc acc tac tcg ctg aaa aaa gac ctc aca gat ctg acc     432
Asp Ser Ser Phe Thr Tyr Ser Leu Lys Lys Asp Leu Thr Asp Leu Thr
        130                 135                 140 agt gtt gaa act gaa aaa tta tcg ttt ggc gca aac ggc aat aaa gtc     480
Ser Val Glu Thr Glu Lys Leu Ser Phe Gly Ala Asn Gly Asn Lys Val
145                 150                 155                 160 aac atc aca agc gac acc aaa ggc ttg aat ttc gcg aaa gaa acg gct     528
Asn Ile Thr Ser Asp Thr Lys Gly Leu Asn Phe Ala Lys Glu Thr Ala
                165                 170                 175 ggg acg aac ggc gac acc acg gtt cat ctg aac ggt att ggt tcg act     576
```

-continued

```
            Gly Thr Asn Gly Asp Thr Thr Val His Leu Asn Gly Ile Gly Ser Thr
                        180                 185                 190 ttg acc gat acg ctg ctg aat acc gga gcg acc aca aac gta acc aac        624
Leu Thr Asp Thr Leu Leu Asn Thr Gly Ala Thr Thr Asn Val Thr Asn
            195                 200                 205 gac aac gtt acc gat gac aag aaa aaa cgt gcg gca agc gtt aaa gac        672
Asp Asn Val Thr Asp Asp Lys Lys Lys Arg Ala Ala Ser Val Lys Asp
    210                 215                 220 gta tta aac gca ggc tgg aac att aaa ggc gtt aaa ccc ggt aca aca        720
Val Leu Asn Ala Gly Trp Asn Ile Lys Gly Val Lys Pro Gly Thr Thr
225                 230                 235                 240 gct tcc gat aac gtt gat ttc gtc cac act tac gac aca gtc gag ttc        768
Ala Ser Asp Asn Val Asp Phe Val His Thr Tyr Asp Thr Val Glu Phe
                245                 250                 255 ttg agc gca gat acg aaa aca acg act gtt aat gtg gaa agc aaa gac        816
Leu Ser Ala Asp Thr Lys Thr Thr Thr Val Asn Val Glu Ser Lys Asp
            260                 265                 270 aac ggc aag aga acc gaa gtt aaa atc ggt gcg aag act tct gtt att        864
Asn Gly Lys Arg Thr Glu Val Lys Ile Gly Ala Lys Thr Ser Val Ile
    275                 280                 285 aaa gaa aaa gac ggt aag ttg gtt act ggt aaa ggc aaa ggc gag aat        912
Lys Glu Lys Asp Gly Lys Leu Val Thr Gly Lys Gly Lys Gly Glu Asn
290                 295                 300 ggt tct tct aca gac gaa ggc gaa ggc tta gtg act gca aaa gaa gtg        960
Gly Ser Ser Thr Asp Glu Gly Glu Gly Leu Val Thr Ala Lys Glu Val
305                 310                 315                 320 att gat gca gta aac aag gct ggt tgg aga atg aaa aca aca acc gct       1008
Ile Asp Ala Val Asn Lys Ala Gly Trp Arg Met Lys Thr Thr Thr Ala
                325                 330                 335 aat ggt caa aca ggt caa gct gac aag ttt gaa acc gtt aca tca ggc       1056
Asn Gly Gln Thr Gly Gln Ala Asp Lys Phe Glu Thr Val Thr Ser Gly
            340                 345                 350 aca aat gta acc ttt gct agt ggt aaa ggt aca act gcg act gta agt       1104
Thr Asn Val Thr Phe Ala Ser Gly Lys Gly Thr Thr Ala Thr Val Ser
    355                 360                 365 aaa gat gat caa ggc aac atc act gtt aag tat gat gta aat gtc ggc       1152
Lys Asp Asp Gln Gly Asn Ile Thr Val Lys Tyr Asp Val Asn Val Gly
370                 375                 380 gat gcc cta aac gtc aat cag ctg caa aac agc ggt tgg aat ttg gat       1200
Asp Ala Leu Asn Val Asn Gln Leu Gln Asn Ser Gly Trp Asn Leu Asp
385                 390                 395                 400 tcc aaa gcg gtt gca ggt tct tcg ggc aaa gtc atc agc ggc aat gtt       1248
Ser Lys Ala Val Ala Gly Ser Ser Gly Lys Val Ile Ser Gly Asn Val
                405                 410                 415 tcg ccg agc aag gga aag atg gat gaa acc gtc aac att aat gcc ggc       1296
Ser Pro Ser Lys Gly Lys Met Asp Glu Thr Val Asn Ile Asn Ala Gly
            420                 425                 430 aac aac atc gag att acc cgc aac ggt aaa aat atc gac atc gcc act       1344
Asn Asn Ile Glu Ile Thr Arg Asn Gly Lys Asn Ile Asp Ile Ala Thr
    435                 440                 445 tcg atg acc ccg cag ttt tcc agc gtt tcg ctc ggc gcg ggg gcg gat       1392
Ser Met Thr Pro Gln Phe Ser Ser Val Ser Leu Gly Ala Gly Ala Asp
450                 455                 460 gcg ccc act ttg agc gtg gat gac aag ggc gcg ttg aat gtc ggc agc       1440
Ala Pro Thr Leu Ser Val Asp Asp Lys Gly Ala Leu Asn Val Gly Ser
465                 470                 475                 480 aag gat gcc aac aaa ccc gtc cgc att acc aat gtc gcc ccg ggc gtt       1488
Lys Asp Ala Asn Lys Pro Val Arg Ile Thr Asn Val Ala Pro Gly Val
                485                 490                 495 aaa gag ggg gat gtt aca aac gtc gca caa ctt aaa ggc gtg gcg caa       1536
```

```
                                                        Lys Glu Gly Asp Val Thr Asn Val Ala Gln Leu Lys Gly Val Ala Gln
                                                                        500                 505                 510 aac ttg aac aac cgc atc gac aat gtg gac ggc aac gcg cgt gcg ggc                                                            1584
Asn Leu Asn Asn Arg Ile Asp Asn Val Asp Gly Asn Ala Arg Ala Gly
            515                 520                 525 atc gcc caa gcg att gca acc gca ggt ctg gtt cag gcg tat ctg ccc                                                            1632
Ile Ala Gln Ala Ile Ala Thr Ala Gly Leu Val Gln Ala Tyr Leu Pro
530                 535                 540 ggc aag agt atg atg gcg atc ggc ggc ggc act tat cgc ggc gaa gcc                                                            1680
Gly Lys Ser Met Met Ala Ile Gly Gly Gly Thr Tyr Arg Gly Glu Ala
545                 550                 555                 560 ggt tac gcc atc ggc tac tcc agt att tcc gac ggc gga aat tgg att                                                            1728
Gly Tyr Ala Ile Gly Tyr Ser Ser Ile Ser Asp Gly Gly Asn Trp Ile
                565                 570                 575 atc aaa ggc acg gct tcc ggc aat tcg cgc ggt cat ttc ggt gct tcc                                                            1776
Ile Lys Gly Thr Ala Ser Gly Asn Ser Arg Gly His Phe Gly Ala Ser
            580                 585                 590 gca tct gtc ggt tat cag tgg taa                                                                                             1800
Ala Ser Val Gly Tyr Gln Trp
            595

<210> SEQ ID NO 15
<211> LENGTH: 599
<212> TYPE: PRT
<213> ORGANISM: Neisseria meningitidis

<400> SEQUENCE: 15

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Pro Val Val
    50                  55                  60

Arg Ser Ala Leu Val Leu Gln Phe Met Ile Asp Lys Glu Gly Asn Gly
65                  70                  75                  80

Glu Asn Glu Ser Thr Gly Asn Ile Gly Trp Ser Ile Tyr Tyr Asp Asn
                85                  90                  95

His Asn Thr Leu His Gly Ala Thr Val Thr Leu Lys Ala Gly Asp Asn
            100                 105                 110

Leu Lys Ile Lys Gln Asn Thr Asn Lys Asn Thr Asn Glu Asn Thr Asn
        115                 120                 125

Asp Ser Ser Phe Thr Tyr Ser Leu Lys Lys Asp Leu Thr Asp Leu Thr
    130                 135                 140

Ser Val Glu Thr Glu Lys Leu Ser Phe Gly Ala Asn Gly Asn Lys Val
145                 150                 155                 160

Asn Ile Thr Ser Asp Thr Lys Gly Leu Asn Phe Ala Lys Glu Thr Ala
                165                 170                 175

Gly Thr Asn Gly Asp Thr Thr Val His Leu Asn Gly Ile Gly Ser Thr
            180                 185                 190

Leu Thr Asp Thr Leu Leu Asn Thr Gly Ala Thr Thr Asn Val Thr Asn
        195                 200                 205

Asp Asn Val Thr Asp Lys Lys Arg Ala Ala Ser Val Lys Asp
    210                 215                 220

Val Leu Asn Ala Gly Trp Asn Ile Lys Gly Val Lys Pro Gly Thr Thr
225                 230                 235                 240
```

Ala Ser Asp Asn Val Asp Phe Val His Thr Tyr Asp Thr Val Glu Phe
                245                 250                 255

Leu Ser Ala Asp Thr Lys Thr Thr Val Asn Val Glu Ser Lys Asp
            260                 265                 270

Asn Gly Lys Arg Thr Glu Val Lys Ile Gly Ala Lys Thr Ser Val Ile
        275                 280                 285

Lys Glu Lys Asp Gly Lys Leu Val Thr Gly Lys Gly Lys Gly Glu Asn
    290                 295                 300

Gly Ser Ser Thr Asp Glu Gly Glu Gly Leu Val Thr Ala Lys Glu Val
305                 310                 315                 320

Ile Asp Ala Val Asn Lys Ala Gly Trp Arg Met Lys Thr Thr Thr Ala
                325                 330                 335

Asn Gly Gln Thr Gly Gln Ala Asp Lys Phe Glu Thr Val Thr Ser Gly
            340                 345                 350

Thr Asn Val Thr Phe Ala Ser Gly Lys Gly Thr Thr Ala Thr Val Ser
        355                 360                 365

Lys Asp Asp Gln Gly Asn Ile Thr Val Lys Tyr Asp Val Asn Val Gly
    370                 375                 380

Asp Ala Leu Asn Val Asn Gln Leu Gln Asn Ser Gly Trp Asn Leu Asp
385                 390                 395                 400

Ser Lys Ala Val Ala Gly Ser Ser Gly Lys Val Ile Ser Gly Asn Val
                405                 410                 415

Ser Pro Ser Lys Gly Lys Met Asp Glu Thr Val Asn Ile Asn Ala Gly
            420                 425                 430

Asn Asn Ile Glu Ile Thr Arg Asn Gly Lys Asn Ile Asp Ile Ala Thr
        435                 440                 445

Ser Met Thr Pro Gln Phe Ser Ser Val Ser Leu Gly Ala Gly Ala Asp
    450                 455                 460

Ala Pro Thr Leu Ser Val Asp Asp Lys Gly Ala Leu Asn Val Gly Ser
465                 470                 475                 480

Lys Asp Ala Asn Lys Pro Val Arg Ile Thr Asn Val Ala Pro Gly Val
                485                 490                 495

Lys Glu Gly Asp Val Thr Asn Val Ala Gln Leu Lys Gly Val Ala Gln
            500                 505                 510

Asn Leu Asn Asn Arg Ile Asp Asn Val Asp Gly Asn Ala Arg Ala Gly
        515                 520                 525

Ile Ala Gln Ala Ile Ala Thr Ala Gly Leu Val Gln Ala Tyr Leu Pro
    530                 535                 540

Gly Lys Ser Met Met Ala Ile Gly Gly Gly Thr Tyr Arg Gly Glu Ala
545                 550                 555                 560

Gly Tyr Ala Ile Gly Tyr Ser Ser Ile Ser Asp Gly Gly Asn Trp Ile
                565                 570                 575

Ile Lys Gly Thr Ala Ser Gly Asn Ser Arg Gly His Phe Gly Ala Ser
            580                 585                 590

Ala Ser Val Gly Tyr Gln Trp
        595

<210> SEQ ID NO 16
<211> LENGTH: 1779
<212> TYPE: DNA
<213> ORGANISM: Neisseria meningitidis
<220> FEATURE:
<221> NAME/KEY: CDS
<222> LOCATION: (1)..(1779)

<400> SEQUENCE: 16

```
atg aac aaa ata tac cgc atc att tgg aat agt gcc ctc aat gcc tgg      48
Met Asn Lys Ile Tyr Arg Ile Ile Trp Asn Ser Ala Leu Asn Ala Trp
1               5                   10                  15 gtc gcc gta tcc gag ctc aca cgc aac cac acc aaa cgc gcc tcc gca      96
Val Ala Val Ser Glu Leu Thr Arg Asn His Thr Lys Arg Ala Ser Ala
            20                  25                  30 acc gtg aag acc gcc gta ttg gcg aca ctg ttg ttt gca acg gtt cag     144
Thr Val Lys Thr Ala Val Leu Ala Thr Leu Leu Phe Ala Thr Val Gln
        35                  40                  45 gcg aat gct acc gat gaa gat gaa gaa gaa gag tta gaa tcc gta caa     192
Ala Asn Ala Thr Asp Glu Asp Glu Glu Glu Glu Leu Glu Ser Val Gln
    50                  55                  60 cgc tct gtc gta ggg agc att caa gcc agt atg gaa ggc agc gtc gaa     240
Arg Ser Val Val Gly Ser Ile Gln Ala Ser Met Glu Gly Ser Val Glu
65                  70                  75                  80 ttg gaa acg ata tca tta tca atg act aac gac agc aag gaa ttt gta     288
Leu Glu Thr Ile Ser Leu Ser Met Thr Asn Asp Ser Lys Glu Phe Val
                85                  90                  95 gac cca tac ata gta gtt acc ctc aaa gcc ggc gac aac ctg aaa atc     336
Asp Pro Tyr Ile Val Val Thr Leu Lys Ala Gly Asp Asn Leu Lys Ile
            100                 105                 110 aaa caa aac acc aat gaa aac acc aat gcc agt agc ttc acc tac tcg     384
Lys Gln Asn Thr Asn Glu Asn Thr Asn Ala Ser Ser Phe Thr Tyr Ser
        115                 120                 125 ctg aaa aaa gac ctc aca ggc ctg atc aat gtt gaa act gaa aaa tta     432
Leu Lys Lys Asp Leu Thr Gly Leu Ile Asn Val Glu Thr Glu Lys Leu
    130                 135                 140 tcg ttt ggc gca aac ggc aag aaa gtc aac atc ata agc gac acc aaa     480
Ser Phe Gly Ala Asn Gly Lys Lys Val Asn Ile Ile Ser Asp Thr Lys
145                 150                 155                 160 ggc ttg aat ttc gcg aaa gaa acg gct ggg acg aac ggc gac acc acg     528
Gly Leu Asn Phe Ala Lys Glu Thr Ala Gly Thr Asn Gly Asp Thr Thr
                165                 170                 175 gtt cat ctg aac ggt atc ggt tcg act ttg acc gat atg ctg ctg aat     576
Val His Leu Asn Gly Ile Gly Ser Thr Leu Thr Asp Met Leu Leu Asn
            180                 185                 190 acc gga gcg acc aca aac gta acc aac gac aac gtt acc gat gac gag     624
Thr Gly Ala Thr Thr Asn Val Thr Asn Asp Asn Val Thr Asp Asp Glu
        195                 200                 205 aaa aaa cgt gcg gca agc gtt aaa gac gta tta aac gca ggc tgg aac     672
Lys Lys Arg Ala Ala Ser Val Lys Asp Val Leu Asn Ala Gly Trp Asn
    210                 215                 220 att aaa ggc gtt aaa ccc ggt aca aca gct tcc gat aac gtt gat ttc     720
Ile Lys Gly Val Lys Pro Gly Thr Thr Ala Ser Asp Asn Val Asp Phe
225                 230                 235                 240 gtc cgc act tac gac aca gtc gag ttc ttg agc gca gat acg aaa aca     768
Val Arg Thr Tyr Asp Thr Val Glu Phe Leu Ser Ala Asp Thr Lys Thr
                245                 250                 255 acg act gtt aat gtg gaa agc aaa gac aac ggc aag aaa acc gaa gtt     816
Thr Thr Val Asn Val Glu Ser Lys Asp Asn Gly Lys Lys Thr Glu Val
            260                 265                 270 aaa atc ggt gcg aag act tct gtt att aaa gaa aaa gac ggt aag ttg     864
Lys Ile Gly Ala Lys Thr Ser Val Ile Lys Glu Lys Asp Gly Lys Leu
        275                 280                 285 gtt act ggt aaa ggc aaa ggc gag aat ggt tct tct aca gac gaa ggc     912
Val Thr Gly Lys Gly Lys Gly Glu Asn Gly Ser Ser Thr Asp Glu Gly
    290                 295                 300 gaa ggc tta gtg act gca aaa gaa gtg att gat gca gta aac aag gct     960
Glu Gly Leu Val Thr Ala Lys Glu Val Ile Asp Ala Val Asn Lys Ala
305                 310                 315                 320
```

```
ggt tgg aga atg aaa aca aca acc gct aat ggt caa aca ggt caa gct    1008
Gly Trp Arg Met Lys Thr Thr Thr Ala Asn Gly Gln Thr Gly Gln Ala
                325                 330                 335 gac aag ttt gaa acc gtt aca tca ggc aca aaa gta acc ttt gct agt    1056
Asp Lys Phe Glu Thr Val Thr Ser Gly Thr Lys Val Thr Phe Ala Ser
            340                 345                 350 ggt aat ggt aca act gcg act gta agt aaa gat gat caa ggc aac atc    1104
Gly Asn Gly Thr Thr Ala Thr Val Ser Lys Asp Asp Gln Gly Asn Ile
        355                 360                 365 act gtt aag tat gat gta aat gtc ggc gat gcc cta aac gtc aat cag    1152
Thr Val Lys Tyr Asp Val Asn Val Gly Asp Ala Leu Asn Val Asn Gln
    370                 375                 380 ctg caa aac agc ggt tgg aat ttg gat tcc aaa gcg gtt gca ggt tct    1200
Leu Gln Asn Ser Gly Trp Asn Leu Asp Ser Lys Ala Val Ala Gly Ser
385                 390                 395                 400 tcg ggc aaa gtc atc agc ggc aat gtt tcg ccg agc aag gga aag atg    1248
Ser Gly Lys Val Ile Ser Gly Asn Val Ser Pro Ser Lys Gly Lys Met
                405                 410                 415 gat gaa acc gtc aac att aat gcc ggc aac aac atc gag att acc cgc    1296
Asp Glu Thr Val Asn Ile Asn Ala Gly Asn Asn Ile Glu Ile Thr Arg
            420                 425                 430 aac ggc aaa aat atc gac atc gcc act tcg atg acc ccg caa ttt tcc    1344
Asn Gly Lys Asn Ile Asp Ile Ala Thr Ser Met Thr Pro Gln Phe Ser
        435                 440                 445 agc gtt tcg ctc ggc gcg ggg gcg gat gcg ccc act tta agc gtg gat    1392
Ser Val Ser Leu Gly Ala Gly Ala Asp Ala Pro Thr Leu Ser Val Asp
    450                 455                 460 gac gag ggc gcg ttg aat gtc ggc agc aag gat gcc aac aaa ccc gtc    1440
Asp Glu Gly Ala Leu Asn Val Gly Ser Lys Asp Ala Asn Lys Pro Val
465                 470                 475                 480 cgc att acc aat gtc gcc ccg ggc gtt aaa gag ggg gat gtt aca aac    1488
Arg Ile Thr Asn Val Ala Pro Gly Val Lys Glu Gly Asp Val Thr Asn
                485                 490                 495 gtc gcg caa ctt aaa ggt gtg gcg caa aac ttg aac aac cgc atc gac    1536
Val Ala Gln Leu Lys Gly Val Ala Gln Asn Leu Asn Asn Arg Ile Asp
            500                 505                 510 aat gtg aac ggc aac gcg cgt gcg ggc atc gcc caa gcg att gca acc    1584
Asn Val Asn Gly Asn Ala Arg Ala Gly Ile Ala Gln Ala Ile Ala Thr
        515                 520                 525 gca ggt ctg gtt cag gcg tat ctg ccc ggc aag agt atg atg gcg atc    1632
Ala Gly Leu Val Gln Ala Tyr Leu Pro Gly Lys Ser Met Met Ala Ile
    530                 535                 540 ggc ggc ggc act tat ctc ggc gaa gcc ggt tat gcc atc ggc tac tca    1680
Gly Gly Gly Thr Tyr Leu Gly Glu Ala Gly Tyr Ala Ile Gly Tyr Ser
545                 550                 555                 560 agc att tcc gcc ggc gga aat tgg att atc aaa ggc acg gct tcc ggc    1728
Ser Ile Ser Ala Gly Gly Asn Trp Ile Ile Lys Gly Thr Ala Ser Gly
                565                 570                 575 aat tcg cgc ggc cat ttc ggt gct tcc gca tct gtc ggt tat cag tgg    1776
Asn Ser Arg Gly His Phe Gly Ala Ser Ala Ser Val Gly Tyr Gln Trp
            580                 585                 590 taa                                                                1779

<210> SEQ ID NO 17
<211> LENGTH: 592
<212> TYPE: PRT
<213> ORGANISM: Neisseria meningitidis

<400> SEQUENCE: 17

Met Asn Lys Ile Tyr Arg Ile Ile Trp Asn Ser Ala Leu Asn Ala Trp
1               5                   10                  15
```

Val Ala Val Ser Glu Leu Thr Arg Asn His Thr Lys Arg Ala Ser Ala
            20                  25                  30

Thr Val Lys Thr Ala Val Leu Ala Thr Leu Phe Ala Thr Val Gln
        35                  40                  45

Ala Asn Ala Thr Asp Glu Asp Glu Glu Glu Leu Glu Ser Val Gln
50                  55                  60

Arg Ser Val Val Gly Ser Ile Gln Ala Ser Met Glu Gly Ser Val Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
            115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Met Leu Leu Asn
            180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
            275                 280                 285

Val Thr Gly Lys Gly Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Lys Val Thr Phe Ala Ser
            340                 345                 350

Gly Asn Gly Thr Thr Ala Thr Val Ser Lys Asp Asp Gln Gly Asn Ile
            355                 360                 365

Thr Val Lys Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser

```
                   435                 440                 445
Ser Val Ser Leu Gly Ala Gly Ala Asp Ala Pro Thr Leu Ser Val Asp
        450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
            500                 505                 510

Asn Val Asn Gly Asn Ala Arg Ala Gly Ile Ala Gln Ala Ile Ala Thr
        515                 520                 525

Ala Gly Leu Val Gln Ala Tyr Leu Pro Gly Lys Ser Met Met Ala Ile
    530                 535                 540

Gly Gly Gly Thr Tyr Leu Gly Glu Ala Gly Tyr Ala Ile Gly Tyr Ser
545                 550                 555                 560

Ser Ile Ser Ala Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
            580                 585                 590

<210> SEQ ID NO 18
<211> LENGTH: 1770
<212> TYPE: DNA
<213> ORGANISM: Neisseria meningitidis
<220> FEATURE:
<221> NAME/KEY: CDS
<222> LOCATION: (1)..(1770)

<400> SEQUENCE: 18 atg aac aaa ata tac cgc atc att tgg aat agt gcc ctc aat gcc tgg      48
Met Asn Lys Ile Tyr Arg Ile Ile Trp Asn Ser Ala Leu Asn Ala Trp
1               5                   10                  15 gta gtc gta tcc gag ctc aca cgc aac cac acc aaa cgc gcc tcc gca      96
Val Val Val Ser Glu Leu Thr Arg Asn His Thr Lys Arg Ala Ser Ala
                20                  25                  30 acc gtg gcg acc gcc gta ttg gcg aca ctg ctg tcc gca acg gtt cag     144
Thr Val Ala Thr Ala Val Leu Ala Thr Leu Leu Ser Ala Thr Val Gln
            35                  40                  45 gcg aat gct acc gat acc gat gaa gat gaa gag tta gaa tcc gta gca     192
Ala Asn Ala Thr Asp Thr Asp Glu Asp Glu Glu Leu Glu Ser Val Ala
        50                  55                  60 cgc tct gct ctg gtg ttg caa ttc atg atc gat aaa gaa ggc aat gga     240
Arg Ser Ala Leu Val Leu Gln Phe Met Ile Asp Lys Glu Gly Asn Gly
65                  70                  75                  80 gaa atc gaa tct aca gga gat ata ggt tgg agt ata tat tac gac gat     288
Glu Ile Glu Ser Thr Gly Asp Ile Gly Trp Ser Ile Tyr Tyr Asp Asp
                85                  90                  95 cac aac act cta cac ggc gca acc gtt acc ctc aaa gcc ggc gac aac     336
His Asn Thr Leu His Gly Ala Thr Val Thr Leu Lys Ala Gly Asp Asn
            100                 105                 110 ctg aaa atc aaa caa agc ggc aaa gac ttc acc tac tcg ctg aaa aaa     384
Leu Lys Ile Lys Gln Ser Gly Lys Asp Phe Thr Tyr Ser Leu Lys Lys
        115                 120                 125 gag ctg aaa gac ctg acc agt gtt gaa act gaa aaa tta tcg ttt ggc     432
Glu Leu Lys Asp Leu Thr Ser Val Glu Thr Glu Lys Leu Ser Phe Gly
    130                 135                 140 gca aac ggt aat aaa gtc aac atc aca agc gac acc aaa ggc ttg aat     480
Ala Asn Gly Asn Lys Val Asn Ile Thr Ser Asp Thr Lys Gly Leu Asn
145                 150                 155                 160
```

```
ttt gcg aaa gaa acg gct ggg acg aac ggc gac ccc acg gtt cat ctg      528
Phe Ala Lys Glu Thr Ala Gly Thr Asn Gly Asp Pro Thr Val His Leu
            165                 170                 175 aac ggt atc ggt tcg act ttg acc gat acg ctt gcg ggt tct tct gct      576
Asn Gly Ile Gly Ser Thr Leu Thr Asp Thr Leu Ala Gly Ser Ser Ala
        180                 185                 190 tct cac gtt gat gcg ggt aac caa agt aca cat tac act cgt gca gca      624
Ser His Val Asp Ala Gly Asn Gln Ser Thr His Tyr Thr Arg Ala Ala
        195                 200                 205 agt att aag gat gtg ttg aat gcg ggt tgg aat att aag ggt gtt aaa      672
Ser Ile Lys Asp Val Leu Asn Ala Gly Trp Asn Ile Lys Gly Val Lys
        210                 215                 220 act ggc tca aca act ggt caa tca gaa aat gtc gat ttc gtc cgc act      720
Thr Gly Ser Thr Thr Gly Gln Ser Glu Asn Val Asp Phe Val Arg Thr
225                 230                 235                 240 tac gac aca gtc gag ttc ttg agc gca gat acg aaa aca acg act gtt      768
Tyr Asp Thr Val Glu Phe Leu Ser Ala Asp Thr Lys Thr Thr Thr Val
                245                 250                 255 aat gtg gaa agc aaa gac aac ggc aag aga acc gaa gtt aaa atc ggt      816
Asn Val Glu Ser Lys Asp Asn Gly Lys Arg Thr Glu Val Lys Ile Gly
            260                 265                 270 gcg aag act tct gtt att aaa gaa aaa gac ggt aag ttg gtt act ggt      864
Ala Lys Thr Ser Val Ile Lys Glu Lys Asp Gly Lys Leu Val Thr Gly
        275                 280                 285 aaa ggc aaa ggc gag aat ggt tct tct aca gac gaa ggc gaa ggc tta      912
Lys Gly Lys Gly Glu Asn Gly Ser Ser Thr Asp Glu Gly Glu Gly Leu
        290                 295                 300 gtg act gca aaa gaa gtg att gat gca gta aac aag gct ggt tgg aga      960
Val Thr Ala Lys Glu Val Ile Asp Ala Val Asn Lys Ala Gly Trp Arg
305                 310                 315                 320 atg aaa aca aca acc gct aat ggt caa aca ggt caa gct gac aag ttt     1008
Met Lys Thr Thr Thr Ala Asn Gly Gln Thr Gly Gln Ala Asp Lys Phe
                325                 330                 335 gaa acc gtt aca tca ggc aca aaa gta acc ttt gct agt ggt aat ggt     1056
Glu Thr Val Thr Ser Gly Thr Lys Val Thr Phe Ala Ser Gly Asn Gly
            340                 345                 350 aca act gcg act gta agt aaa gat gat caa ggc aac atc act gtt aag     1104
Thr Thr Ala Thr Val Ser Lys Asp Asp Gln Gly Asn Ile Thr Val Lys
        355                 360                 365 tat gat gta aat gtc ggc gat gcc cta aac gtc aat cag ctg caa aac     1152
Tyr Asp Val Asn Val Gly Asp Ala Leu Asn Val Asn Gln Leu Gln Asn
        370                 375                 380 agc ggt tgg aat ttg gat tcc aaa gcg gtt gca ggt tct tcg ggc aaa     1200
Ser Gly Trp Asn Leu Asp Ser Lys Ala Val Ala Gly Ser Ser Gly Lys
385                 390                 395                 400 gtc atc agc ggc aat gtt tcg ccg agc aag gga aag atg gat gaa acc     1248
Val Ile Ser Gly Asn Val Ser Pro Ser Lys Gly Lys Met Asp Glu Thr
                405                 410                 415 gtc aac att aat gcc ggc aac aac atc gag att acc cgc aac ggc aaa     1296
Val Asn Ile Asn Ala Gly Asn Asn Ile Glu Ile Thr Arg Asn Gly Lys
            420                 425                 430 aat atc gac atc gcc act tcg atg acc ccg caa ttt tcc agc gtt tcg     1344
Asn Ile Asp Ile Ala Thr Ser Met Thr Pro Gln Phe Ser Ser Val Ser
        435                 440                 445 ctc ggc gcg ggg gcg gat gcg ccc act tta agc gtg gat gac gag ggc     1392
Leu Gly Ala Gly Ala Asp Ala Pro Thr Leu Ser Val Asp Asp Glu Gly
        450                 455                 460 gcg ttg aat gtc ggc agc aag gat gcc aac aaa ccc gtc cgc att acc     1440
Ala Leu Asn Val Gly Ser Lys Asp Ala Asn Lys Pro Val Arg Ile Thr
465                 470                 475                 480
```

```
aat gtc gcc ccg ggc gtt aaa gag ggg gat gtt aca aac gtc gca caa    1488
Asn Val Ala Pro Gly Val Lys Glu Gly Asp Val Thr Asn Val Ala Gln
            485                 490                 495 ctt aaa ggt gtg gcg caa aac ttg aac aac cgc atc gac aat gtg aac    1536
Leu Lys Gly Val Ala Gln Asn Leu Asn Asn Arg Ile Asp Asn Val Asn
        500                 505                 510 ggc aac gcg cgc gcg ggt atc gcc caa gcg att gca acc gca ggt ttg    1584
Gly Asn Ala Arg Ala Gly Ile Ala Gln Ala Ile Ala Thr Ala Gly Leu
    515                 520                 525 gct cag gcc tat ttg ccc ggc aag agt atg atg gcg atc ggc ggc ggt    1632
Ala Gln Ala Tyr Leu Pro Gly Lys Ser Met Met Ala Ile Gly Gly Gly
530                 535                 540 act tat ctc ggc gaa gcc ggt tac gcc atc ggc tac tcg agc att tct    1680
Thr Tyr Leu Gly Glu Ala Gly Tyr Ala Ile Gly Tyr Ser Ser Ile Ser
545                 550                 555                 560 gac act ggg aat tgg gtt atc aag ggc acg gct tcc ggc aat tcg cgc    1728
Asp Thr Gly Asn Trp Val Ile Lys Gly Thr Ala Ser Gly Asn Ser Arg
                565                 570                 575 ggt cat ttc ggt act tcc gca tct gtc ggt tat cag tgg taa            1770
Gly His Phe Gly Thr Ser Ala Ser Val Gly Tyr Gln Trp
            580                 585

<210> SEQ ID NO 19
<211> LENGTH: 589
<212> TYPE: PRT
<213> ORGANISM: Neisseria meningitidis

<400> SEQUENCE: 19

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Ser Ala Thr Val Gln
        35                  40                  45

Ala Asn Ala Thr Asp Thr Asp Glu Asp Glu Glu Leu Glu Ser Val Ala
    50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
                85                  90                  95

His Asn Thr Leu His Gly Ala Thr Val Thr Leu Lys Ala Gly Asp Asn
            100                 105                 110

Leu Lys Ile Lys Gln Ser Gly Lys Asp Phe Thr Tyr Ser Leu Lys Lys
        115                 120                 125

Glu Leu Lys Asp Leu Thr Ser Val Glu Thr Glu Lys Leu Ser Phe Gly
    130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175

Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
        195                 200                 205

Ser Ile Lys Asp Val Leu Asn Ala Gly Trp Asn Ile Lys Gly Val Lys
    210                 215                 220

Thr Gly Ser Thr Thr Gly Gln Ser Glu Asn Val Asp Phe Val Arg Thr
225                 230                 235                 240
```

```
Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
        275                 280                 285

Lys Gly Lys Gly Glu Asn Gly Ser Ser Thr Asp Glu Gly Glu Gly Leu
290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
            340                 345                 350

Thr Thr Ala Thr Val Ser Lys Asp Asp Gln Gly Asn Ile Thr Val Lys
        355                 360                 365

Tyr Asp Val Asn Val Gly Asp Ala Leu Asn Val Asn Gln Leu Gln Asn
370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
        435                 440                 445

Leu Gly Ala Gly Ala Asp Ala Pro Thr Leu Ser Val Asp Asp Glu Gly
450                 455                 460

Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
                485                 490                 495

Leu Lys Gly Val Ala Gln Asn Leu Asn Asn Arg Ile Asp Asn Val Asn
            500                 505                 510

Gly Asn Ala Arg Ala Gly Ile Ala Gln Ala Ile Ala Thr Ala Gly Leu
        515                 520                 525

Ala Gln Ala Tyr Leu Pro Gly Lys Ser Met Met Ala Ile Gly Gly Gly
530                 535                 540

Thr Tyr Leu Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585

<210> SEQ ID NO 20
<211> LENGTH: 1776
<212> TYPE: DNA
<213> ORGANISM: Neisseria meningitidis
<220> FEATURE:
<221> NAME/KEY: CDS
<222> LOCATION: (1)..(1776)

<400> SEQUENCE: 20 atg aac aaa ata tac cgc atc att tgg aat agt gcc ctc aat gca tgg        48
Met Asn Lys Ile Tyr Arg Ile Ile Trp Asn Ser Ala Leu Asn Ala Trp
```

```
  1               5                   10                  15
gtc gtc gta tcc gag ctc aca cgc aac cac acc aaa cgc gcc tcc gca         96
Val Val Val Ser Glu Leu Thr Arg Asn His Thr Lys Arg Ala Ser Ala
             20                  25                  30 acc gtg aag acc gcc gta ttg gcg act ctg ttg ttt gca acg gtt cag        144
Thr Val Lys Thr Ala Val Leu Ala Thr Leu Leu Phe Ala Thr Val Gln
             35                  40                  45 gca agt gct aac aat gaa gag caa gaa gaa gat tta tat tta gac ccc        192
Ala Ser Ala Asn Asn Glu Glu Gln Glu Glu Asp Leu Tyr Leu Asp Pro
             50                  55                  60 gta caa cgc act gtt gcc gtg ttg ata gtc aat tcc gat aaa gaa ggc        240
Val Gln Arg Thr Val Ala Val Leu Ile Val Asn Ser Asp Lys Glu Gly
65               70                  75                  80 acg gga gaa aaa gaa aaa gta gaa gaa aat tca gat tgg gca gta tat        288
Thr Gly Glu Lys Glu Lys Val Glu Glu Asn Ser Asp Trp Ala Val Tyr
                 85                  90                  95 ttc aac gag aaa gga gta cta aca gcc aga gaa atc acc ctc aaa gcc        336
Phe Asn Glu Lys Gly Val Leu Thr Ala Arg Glu Ile Thr Leu Lys Ala
                100                 105                 110 ggc gac aac ctg aaa atc aaa caa aac ggc aca aac ttc acc tac tcg        384
Gly Asp Asn Leu Lys Ile Lys Gln Asn Gly Thr Asn Phe Thr Tyr Ser
            115                 120                 125 ctg aaa aaa gac ctc aca gat ctg acc agt gtt gga act gaa aaa tta        432
Leu Lys Lys Asp Leu Thr Asp Leu Thr Ser Val Gly Thr Glu Lys Leu
130             135                 140 tcg ttt agc gca aac ggc aat aaa gtc aac atc aca agc gac acc aaa        480
Ser Phe Ser Ala Asn Gly Asn Lys Val Asn Ile Thr Ser Asp Thr Lys
145                 150                 155                 160 ggc ttg aat ttt gcg aaa gaa acg gct ggg acg aac ggc gac acc acg        528
Gly Leu Asn Phe Ala Lys Glu Thr Ala Gly Thr Asn Gly Asp Thr Thr
                165                 170                 175 gtt cat ctg aac ggt att ggt tcg act ttg acc gat acg ctg ctg aat        576
Val His Leu Asn Gly Ile Gly Ser Thr Leu Thr Asp Thr Leu Leu Asn
            180                 185                 190 acc gga gcg acc aca aac gta acc aac gac aac gtt acc gat gac gag        624
Thr Gly Ala Thr Thr Asn Val Thr Asn Asp Asn Val Thr Asp Asp Glu
        195                 200                 205 aaa aaa cgt gcg gca agc gtt aaa gac gta tta aac gct ggc tgg aac        672
Lys Lys Arg Ala Ala Ser Val Lys Asp Val Leu Asn Ala Gly Trp Asn
210                 215                 220 att aaa ggc gtt aaa ccc ggt aca aca gct tcc gat aac gtt gat ttc        720
Ile Lys Gly Val Lys Pro Gly Thr Thr Ala Ser Asp Asn Val Asp Phe
225                 230                 235                 240 gtc cgc act tac gac aca gtc gag ttc ttg agc gca gat acg aaa aca        768
Val Arg Thr Tyr Asp Thr Val Glu Phe Leu Ser Ala Asp Thr Lys Thr
                245                 250                 255 acg act gtt aat gtg gaa agc aaa gac aac ggc aag aaa acc gaa gtt        816
Thr Thr Val Asn Val Glu Ser Lys Asp Asn Gly Lys Lys Thr Glu Val
            260                 265                 270 aaa atc ggt gcg aag act tct gtt att aaa gaa aaa gac ggt aag ttg        864
Lys Ile Gly Ala Lys Thr Ser Val Ile Lys Glu Lys Asp Gly Lys Leu
        275                 280                 285 gtt act ggt aaa gac aaa ggc gag aat ggt tct tct aca gac gaa ggc        912
Val Thr Gly Lys Asp Lys Gly Glu Asn Gly Ser Ser Thr Asp Glu Gly
    290                 295                 300 gaa ggc tta gtg act gca aaa gaa gtg att gat gca gta aac aag gct        960
Glu Gly Leu Val Thr Ala Lys Glu Val Ile Asp Ala Val Asn Lys Ala
305                 310                 315                 320 ggt tgg aga atg aaa aca aca acc gct aat ggt caa aca ggt caa gct       1008
Gly Trp Arg Met Lys Thr Thr Thr Ala Asn Gly Gln Thr Gly Gln Ala
```

```
                        325                 330                 335
gac aag ttt gaa acc gtt aca tca ggc aca aat gta acc ttt gct agt      1056
Asp Lys Phe Glu Thr Val Thr Ser Gly Thr Asn Val Thr Phe Ala Ser
            340                 345                 350 ggt aaa ggt aca act gcg act gta agt aaa gat gat caa ggc aac atc      1104
Gly Lys Gly Thr Thr Ala Thr Val Ser Lys Asp Asp Gln Gly Asn Ile
        355                 360                 365 act gtt atg tat gat gta aat gtc ggc gat gcc cta aac gtc aat cag      1152
Thr Val Met Tyr Asp Val Asn Val Gly Asp Ala Leu Asn Val Asn Gln
    370                 375                 380 ctg caa aac agc ggt tgg aat ttg gat tcc aaa gcg gtt gca ggt tct      1200
Leu Gln Asn Ser Gly Trp Asn Leu Asp Ser Lys Ala Val Ala Gly Ser
385                 390                 395                 400 tcg ggc aaa gtc atc agc ggc aat gtt tcg ccg agc aag gga aag atg      1248
Ser Gly Lys Val Ile Ser Gly Asn Val Ser Pro Ser Lys Gly Lys Met
                405                 410                 415 gat gaa acc gtc aac att aat gcc ggc aac aac atc gag att acc cgc      1296
Asp Glu Thr Val Asn Ile Asn Ala Gly Asn Asn Ile Glu Ile Thr Arg
            420                 425                 430 aac ggt aaa aat atc gac atc gcc act tcg atg acc ccg cag ttt tcc      1344
Asn Gly Lys Asn Ile Asp Ile Ala Thr Ser Met Thr Pro Gln Phe Ser
        435                 440                 445 agc gtt tcg ctc ggc gcg ggg gcg gat gcg ccc act ttg agc gtg gat      1392
Ser Val Ser Leu Gly Ala Gly Ala Asp Ala Pro Thr Leu Ser Val Asp
    450                 455                 460 ggg gac gca ttg aat gtc ggc agc aag aag gac aac aaa ccc gtc cgc      1440
Gly Asp Ala Leu Asn Val Gly Ser Lys Lys Asp Asn Lys Pro Val Arg
465                 470                 475                 480 att acc aat gtc gcc ccg ggc gtt aaa gag ggg gat gtt aca aac gtc      1488
Ile Thr Asn Val Ala Pro Gly Val Lys Glu Gly Asp Val Thr Asn Val
                485                 490                 495 gca caa ctt aaa ggc gtg gcg caa aac ttg aac aac cgc atc gac aat      1536
Ala Gln Leu Lys Gly Val Ala Gln Asn Leu Asn Asn Arg Ile Asp Asn
            500                 505                 510 gtg gac ggc aac gcg cgt gcg ggc atc gcc caa gcg att gca acc gca      1584
Val Asp Gly Asn Ala Arg Ala Gly Ile Ala Gln Ala Ile Ala Thr Ala
        515                 520                 525 ggt ctg gtt cag gcg tat ttg ccc ggc aag agt atg atg gcg atc ggc      1632
Gly Leu Val Gln Ala Tyr Leu Pro Gly Lys Ser Met Met Ala Ile Gly
    530                 535                 540 ggc act tat cgc ggc gaa gcc ggt tac gcc atc ggc tac tcc agt      1680
Gly Gly Thr Tyr Arg Gly Glu Ala Gly Tyr Ala Ile Gly Tyr Ser Ser
545                 550                 555                 560 att tcc gac ggc gga aat tgg att atc aaa ggc acg gct tcc ggc aat      1728
Ile Ser Asp Gly Gly Asn Trp Ile Ile Lys Gly Thr Ala Ser Gly Asn
                565                 570                 575 tcg cgc ggc cat ttc ggt gct tcc gca tct gtc ggt tat cag tgg taa      1776
Ser Arg Gly His Phe Gly Ala Ser Ala Ser Val Gly Tyr Gln Trp
            580                 585                 590

<210> SEQ ID NO 21
<211> LENGTH: 591
<212> TYPE: PRT
<213> ORGANISM: Neisseria meningitidis

<400> SEQUENCE: 21

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30
```

-continued

```
Thr Val Lys Thr Ala Val Leu Ala Thr Leu Phe Ala Thr Val Gln
         35                  40                  45

Ala Ser Ala Asn Asn Glu Glu Gln Glu Glu Asp Leu Tyr Leu Asp Pro
 50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
                115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Glu
                195                 200                 205

Lys Lys Arg Ala Ala Ser Val Lys Asp Val Leu Asn Ala Gly Trp Asn
210                 215                 220

Ile Lys Gly Val Lys Pro Gly Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270

Lys Ile Gly Ala Lys Thr Ser Val Ile Lys Glu Lys Asp Gly Lys Leu
                275                 280                 285

Val Thr Gly Lys Asp Lys Gly Glu Asn Gly Ser Ser Thr Asp Glu Gly
                290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
                355                 360                 365

Thr Val Met Tyr Asp Val Asn Val Gly Asp Ala Leu Asn Val Asn Gln
                370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
                450                 455                 460
```

```
Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttagattcca cgtcccagat t                                              21

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttcccttca aaccttcc                                                  18

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtcgcggat ccatgaacaa aatataccgc at                                  32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcacccaagc ttaagccctt accactgata ac                                  32

<210> SEQ ID NO 26
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccaaaccccg atttaacc                                                     18

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aatcgccacc cttcccttc                                                    19

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttgcaacgg ttcaggca                                                     18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tattcagcag cgtatcgg                                                     18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgcctgaacc gttgcaaa                                                     18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccgatacgct gctgaata                                                     18

<210> SEQ ID NO 32
<211> LENGTH: 1098
<212> TYPE: PRT
<213> ORGANISM: Haemophilus influenzae
```

<400> SEQUENCE: 32

```
Met Asn Lys Ile Phe Asn Val Ile Trp Asn Val Val Thr Gln Thr Trp
1               5                   10                  15

Val Val Val Ser Glu Leu Thr Arg Thr His Thr Lys Cys Ala Ser Ala
            20                  25                  30

Thr Val Ala Val Ala Val Leu Ala Thr Leu Leu Ser Ala Thr Val Glu
        35                  40                  45

Ala Asn Asn Asn Thr Pro Val Thr Asn Lys Leu Lys Ala Tyr Gly Asp
    50                  55                  60

Ala Asn Phe Asn Phe Thr Asn Asn Ser Ile Ala Asp Ala Glu Lys Gln
65                  70                  75                  80

Val Gln Glu Ala Tyr Lys Gly Leu Leu Asn Leu Asn Glu Lys Asn Ala
                85                  90                  95

Ser Asp Lys Leu Leu Val Glu Asp Asn Thr Ala Ala Thr Val Gly Asn
            100                 105                 110

Leu Arg Lys Leu Gly Trp Val Leu Ser Ser Lys Asn Gly Thr Arg Asn
        115                 120                 125

Glu Lys Ser Gln Gln Val Lys His Ala Asp Glu Val Leu Phe Glu Gly
    130                 135                 140

Lys Gly Gly Val Gln Val Thr Ser Thr Glu Asn Gly Lys His Thr
145                 150                 155                 160

Ile Thr Phe Ala Leu Ala Lys Asp Leu Gly Val Lys Thr Ala Thr Val
                165                 170                 175

Ser Asp Thr Leu Thr Ile Gly Gly Gly Ala Ala Ala Gly Ala Thr Thr
            180                 185                 190

Thr Pro Lys Val Asn Val Thr Ser Thr Thr Asp Gly Leu Lys Phe Ala
        195                 200                 205

Lys Asp Ala Ala Gly Ala Asn Gly Asp Thr Thr Val His Leu Asn Gly
    210                 215                 220

Ile Gly Ser Thr Leu Thr Asp Thr Leu Val Gly Ser Pro Ala Thr His
225                 230                 235                 240

Ile Asp Gly Gly Asp Gln Ser Thr His Tyr Thr Arg Ala Ala Ser Ile
                245                 250                 255

Lys Asp Val Leu Asn Ala Gly Trp Asn Ile Lys Gly Val Lys Ala Gly
            260                 265                 270

Ser Thr Thr Gly Gln Ser Glu Asn Val Asp Phe Val His Thr Tyr Asp
        275                 280                 285

Thr Val Glu Phe Leu Ser Ala Asp Thr Glu Thr Thr Val Thr Val
    290                 295                 300

Asp Ser Lys Glu Asn Gly Lys Arg Thr Glu Val Lys Ile Gly Ala Lys
305                 310                 315                 320

Thr Ser Val Ile Lys Glu Lys Asp Gly Lys Leu Phe Thr Gly Lys Ala
                325                 330                 335

Asn Lys Glu Thr Asn Lys Val Asp Gly Ala Asn Ala Thr Glu Asp Ala
            340                 345                 350

Asp Glu Gly Lys Gly Leu Val Thr Ala Lys Asp Val Ile Asp Ala Val
        355                 360                 365

Asn Lys Thr Gly Trp Arg Ile Lys Thr Thr Asp Ala Asn Gly Gln Asn
    370                 375                 380

Gly Asp Phe Ala Thr Val Ala Ser Gly Thr Asn Val Thr Phe Ala Ser
385                 390                 395                 400

Gly Asn Gly Thr Thr Ala Thr Val Thr Asn Gly Thr Asp Gly Ile Thr
                405                 410                 415
```

-continued

```
Val Lys Tyr Asp Ala Lys Val Gly Asp Gly Leu Lys Leu Asp Gly Asp
            420                 425                 430
Lys Ile Ala Ala Asp Thr Thr Ala Leu Thr Val Asn Asp Gly Lys Asn
435                 440                 445
Ala Asn Asn Pro Lys Gly Lys Val Ala Asp Val Ala Ser Thr Asp Glu
450                 455                 460
Lys Lys Leu Val Thr Ala Lys Gly Leu Val Thr Ala Leu Asn Ser Leu
465                 470                 475                 480
Ser Trp Thr Thr Thr Ala Ala Glu Ala Asp Gly Thr Leu Asp Gly
            485                 490                 495
Asn Ala Ser Glu Gln Glu Val Lys Ala Gly Asp Lys Val Thr Phe Lys
            500                 505                 510
Ala Gly Lys Asn Leu Lys Val Lys Gln Glu Gly Ala Asn Phe Thr Tyr
            515                 520                 525
Ser Leu Gln Asp Ala Leu Thr Gly Leu Thr Ser Ile Thr Leu Gly Thr
            530                 535                 540
Gly Asn Asn Gly Ala Lys Thr Glu Ile Asn Lys Asp Gly Leu Thr Ile
545                 550                 555                 560
Thr Pro Ala Asn Gly Ala Gly Ala Asn Asn Ala Asn Thr Ile Ser Val
            565                 570                 575
Thr Lys Asp Gly Ile Ser Ala Gly Gly Gln Ser Val Lys Asn Val Val
            580                 585                 590
Ser Gly Leu Lys Lys Phe Gly Asp Ala Asn Phe Asp Pro Leu Thr Ser
            595                 600                 605
Ser Ala Asp Asn Leu Thr Lys Gln Asn Asp Asp Ala Tyr Lys Gly Leu
            610                 615                 620
Thr Asn Leu Asp Glu Lys Gly Thr Asp Lys Gln Thr Pro Val Val Ala
625                 630                 635                 640
Asp Asn Thr Ala Ala Thr Val Gly Asp Leu Arg Gly Leu Gly Trp Val
            645                 650                 655
Ile Ser Ala Asp Lys Thr Thr Gly Gly Ser Thr Glu Tyr His Asp Gln
            660                 665                 670
Val Arg Asn Ala Asn Glu Val Lys Phe Lys Ser Gly Asn Gly Ile Asn
            675                 680                 685
Val Ser Gly Lys Thr Val Asn Gly Arg Arg Glu Ile Thr Phe Glu Leu
            690                 695                 700
Ala Lys Gly Glu Val Val Lys Ser Asn Glu Phe Thr Val Lys Glu Thr
705                 710                 715                 720
Asn Gly Lys Glu Thr Ser Leu Val Lys Val Gly Asp Lys Tyr Tyr Ser
            725                 730                 735
Lys Glu Asp Ile Asp Leu Thr Thr Gly Gln Pro Lys Leu Lys Asp Gly
            740                 745                 750
Asn Thr Val Ala Ala Lys Tyr Gln Asp Lys Gly Gly Lys Val Val Ser
            755                 760                 765
Val Thr Asp Asn Thr Glu Ala Thr Ile Thr Asn Lys Gly Ser Gly Tyr
            770                 775                 780
Val Thr Gly Asn Gln Val Ala Asp Ala Ile Ala Lys Ser Gly Phe Glu
785                 790                 795                 800
Leu Gly Leu Ala Asp Glu Ala Asp Ala Lys Arg Ala Phe Asp Asp Lys
            805                 810                 815
Thr Lys Ala Leu Ser Ala Gly Thr Thr Glu Ile Val Asn Ala His Asp
            820                 825                 830
Lys Val Arg Phe Ala Asn Gly Leu Asn Thr Lys Val Ser Ala Ala Thr
```

```
                     835                 840                 845
Val Glu Ser Thr Asp Ala Asn Gly Asp Lys Val Thr Thr Phe Val
850                 855                 860

Lys Thr Asp Val Glu Leu Pro Leu Thr Gln Ile Tyr Asn Thr Asp Ala
865                 870                 875                 880

Asn Gly Lys Lys Ile Thr Lys Val Val Lys Asp Gly Gln Thr Lys Trp
                    885                 890                 895

Tyr Glu Leu Asn Ala Asp Gly Thr Ala Asp Met Thr Lys Glu Val Thr
                900                 905                 910

Leu Gly Asn Val Asp Ser Asp Gly Lys Lys Val Val Lys Asp Asn Asp
                915                 920                 925

Gly Lys Trp Tyr His Ala Lys Ala Asp Gly Thr Ala Asp Lys Thr Lys
930                 935                 940

Gly Glu Val Ser Asn Asp Lys Val Ser Thr Asp Glu Lys His Val Val
945                 950                 955                 960

Ser Leu Asp Pro Asn Asp Gln Ser Lys Gly Lys Gly Val Val Ile Asp
                965                 970                 975

Asn Val Ala Asn Gly Asp Ile Ser Ala Thr Ser Thr Asp Ala Ile Asn
                980                 985                 990

Gly Ser Gln Leu Tyr Ala Val Ala Lys Gly Val Thr Asn Leu Ala Gly
                995                 1000                1005

Gln Val Asn Asn Leu Glu Gly Lys Val Asn Lys Val Gly Lys Arg
        1010                1015                1020

Ala Asp Ala Gly Thr Ala Ser Ala Leu Ala Ala Ser Gln Leu Pro
        1025                1030                1035

Gln Ala Thr Met Pro Gly Lys Ser Met Val Ala Ile Ala Gly Ser
        1040                1045                1050

Ser Tyr Gln Gly Gln Asn Gly Leu Ala Ile Gly Val Ser Arg Ile
        1055                1060                1065

Ser Asp Asn Gly Lys Val Ile Ile Arg Leu Ser Gly Thr Thr Asn
        1070                1075                1080

Ser Gln Gly Lys Thr Gly Val Ala Ala Gly Val Gly Tyr Gln Trp
        1085                1090                1095

<210> SEQ ID NO 33
<211> LENGTH: 2353
<212> TYPE: PRT
<213> ORGANISM: Haemophilus influenzae

<400> SEQUENCE: 33

Met Asn Lys Ile Phe Asn Val Ile Trp Asn Val Met Thr Gln Thr Trp
1               5                   10                  15

Val Val Val Ser Glu Leu Thr Arg Thr His Thr Lys Arg Ala Ser Ala
                20                  25                  30

Thr Val Glu Thr Ala Val Leu Ala Thr Leu Leu Phe Ala Thr Val Gln
                35                  40                  45

Ala Asn Ala Thr Asp Glu Asp Glu Glu Leu Asp Pro Val Val Arg Thr
                50                  55                  60

Ala Pro Val Leu Ser Phe His Ser Asp Lys Glu Gly Thr Gly Glu Lys
65                  70                  75                  80

Glu Val Thr Glu Asn Ser Asn Trp Gly Ile Tyr Phe Asp Asn Lys Gly
                    85                  90                  95

Val Leu Lys Ala Gly Ala Ile Thr Leu Lys Ala Gly Asp Asn Leu Lys
                100                 105                 110

Ile Lys Gln Asn Thr Asp Glu Ser Thr Asn Ala Ser Ser Phe Thr Tyr
```

115                 120                 125
Ser Leu Lys Lys Asp Leu Thr Asp Leu Thr Ser Val Ala Thr Glu Lys
130                 135                 140

Leu Ser Phe Gly Ala Asn Gly Asp Lys Val Asp Ile Thr Ser Asp Ala
145                 150                 155                 160

Asn Gly Leu Lys Leu Ala Lys Thr Gly Asn Gly Asn Val His Leu Asn
                    165                 170                 175

Gly Leu Asp Ser Thr Leu Pro Asp Ala Val Thr Asn Thr Gly Val Leu
                180                 185                 190

Ser Ser Ser Ser Phe Thr Pro Asn Asp Val Glu Lys Thr Arg Ala Ala
                195                 200                 205

Thr Val Lys Asp Val Leu Asn Ala Gly Trp Asn Ile Lys Gly Ala Lys
210                 215                 220

Thr Ala Gly Gly Asn Val Glu Ser Val Asp Leu Val Ser Ala Tyr Asn
225                 230                 235                 240

Asn Val Glu Phe Ile Thr Gly Asp Lys Asn Thr Leu Asp Val Val Leu
                    245                 250                 255

Thr Ala Lys Glu Asn Gly Lys Thr Thr Glu Val Lys Phe Thr Pro Lys
                260                 265                 270

Thr Ser Val Ile Lys Glu Lys Asp Gly Lys Leu Phe Thr Gly Lys Glu
                275                 280                 285

Asn Asn Asp Thr Asn Lys Val Thr Ser Asn Thr Ala Thr Asp Asn Thr
                290                 295                 300

Asp Glu Gly Asn Gly Leu Val Thr Ala Lys Ala Val Ile Asp Ala Val
305                 310                 315                 320

Asn Lys Ala Gly Trp Arg Val Lys Thr Thr Thr Ala Asn Gly Gln Asn
                    325                 330                 335

Gly Asp Phe Ala Thr Val Ala Ser Gly Thr Asn Val Thr Phe Glu Ser
                340                 345                 350

Gly Asp Gly Thr Thr Ala Ser Val Thr Lys Asp Thr Asn Gly Asn Gly
                355                 360                 365

Ile Thr Val Lys Tyr Asp Ala Lys Val Gly Asp Gly Leu Lys Phe Asp
370                 375                 380

Ser Asp Lys Lys Ile Val Ala Asp Thr Thr Ala Leu Thr Val Thr Gly
385                 390                 395                 400

Gly Lys Val Ala Glu Ile Ala Lys Glu Asp Lys Lys Leu Val
                    405                 410                 415

Asn Ala Gly Asp Leu Val Thr Ala Leu Gly Asn Leu Ser Trp Lys Ala
                420                 425                 430

Lys Ala Glu Ala Asp Thr Asp Gly Ala Leu Glu Gly Ile Ser Lys Asp
                435                 440                 445

Gln Glu Val Lys Ala Gly Glu Thr Val Thr Phe Lys Ala Gly Lys Asn
                450                 455                 460

Leu Lys Val Lys Gln Asp Gly Ala Asn Phe Thr Tyr Ser Leu Gln Asp
465                 470                 475                 480

Ala Leu Thr Gly Leu Thr Ser Ile Thr Leu Gly Gly Thr Thr Asn Gly
                    485                 490                 495

Gly Asn Asp Ala Lys Thr Val Ile Asn Lys Asp Gly Leu Thr Ile Thr
                500                 505                 510

Pro Ala Gly Asn Gly Thr Thr Gly Thr Asn Thr Ile Ser Val Thr
                515                 520                 525

Lys Asp Gly Ile Lys Ala Gly Asn Lys Ala Ile Thr Asn Val Ala Ser
530                 535                 540

-continued

```
Gly Leu Arg Ala Tyr Asp Asp Ala Asn Phe Asp Val Leu Asn Asn Ser
545                 550                 555                 560

Ala Thr Asp Leu Asn Arg His Val Glu Asp Ala Tyr Lys Gly Leu Leu
                565                 570                 575

Asn Leu Asn Glu Lys Asn Ala Asn Lys Gln Pro Leu Val Thr Asp Ser
            580                 585                 590

Thr Ala Ala Thr Val Gly Asp Leu Arg Lys Leu Gly Trp Val Val Ser
        595                 600                 605

Thr Lys Asn Gly Thr Lys Glu Glu Ser Asn Gln Val Lys Gln Ala Asp
    610                 615                 620

Glu Val Leu Phe Thr Gly Ala Gly Ala Thr Val Thr Ser Lys Ser
625                 630                 635                 640

Glu Asn Gly Lys His Thr Ile Thr Val Ser Val Ala Glu Thr Lys Ala
                645                 650                 655

Asp Cys Gly Leu Glu Lys Asp Gly Asp Thr Ile Lys Leu Lys Val Asp
            660                 665                 670

Asn Gln Asn Thr Asp Asn Val Leu Thr Val Gly Asn Gly Thr Ala
        675                 680                 685

Val Thr Lys Gly Phe Glu Thr Val Lys Thr Gly Ala Thr Asp Ala
690                 695                 700

Asp Arg Gly Lys Val Thr Val Lys Asp Ala Thr Ala Asn Asp Ala Asp
705                 710                 715                 720

Lys Lys Val Ala Thr Val Lys Asp Val Ala Thr Ala Ile Asn Ser Ala
                725                 730                 735

Ala Thr Phe Val Lys Thr Glu Asn Leu Thr Thr Ser Ile Asp Glu Asp
            740                 745                 750

Asn Pro Thr Asp Asn Gly Lys Asp Asp Ala Leu Lys Ala Gly Asp Thr
        755                 760                 765

Leu Thr Phe Lys Ala Gly Lys Asn Leu Lys Val Lys Arg Asp Gly Lys
    770                 775                 780

Asn Ile Thr Phe Asp Leu Ala Lys Asn Leu Glu Val Lys Thr Ala Lys
785                 790                 795                 800

Val Ser Asp Thr Leu Thr Ile Gly Gly Asn Thr Pro Thr Gly Gly Thr
                805                 810                 815

Thr Ala Thr Pro Lys Val Asn Ile Thr Ser Thr Ala Asp Gly Leu Asn
            820                 825                 830

Phe Ala Lys Glu Thr Ala Asp Ala Ser Gly Ser Lys Asn Val Tyr Leu
        835                 840                 845

Lys Gly Ile Ala Thr Thr Leu Thr Glu Pro Ser Ala Gly Ala Lys Ser
    850                 855                 860

Ser His Val Asp Leu Asn Val Asp Ala Thr Lys Lys Ser Asn Ala Ala
865                 870                 875                 880

Ser Ile Glu Asp Val Leu Arg Ala Gly Trp Asn Ile Gln Gly Asn Gly
                885                 890                 895

Asn Asn Val Asp Tyr Val Ala Thr Tyr Asp Thr Val Asn Phe Thr Asp
            900                 905                 910

Asp Ser Thr Gly Thr Thr Val Thr Val Thr Gln Lys Ala Asp Gly
        915                 920                 925

Lys Gly Ala Asp Val Lys Ile Gly Ala Lys Thr Ser Val Ile Lys Asp
    930                 935                 940

His Asn Gly Lys Leu Phe Thr Gly Lys Asp Leu Lys Asp Ala Asn Asn
945                 950                 955                 960

Gly Ala Thr Val Ser Glu Asp Asp Gly Lys Asp Thr Gly Thr Gly Leu
                965                 970                 975
```

```
Val Thr Ala Lys Thr Val Ile Asp Ala Val Asn Lys Ser Gly Trp Arg
            980                 985                 990

Val Thr Gly Glu Gly Ala Thr Ala  Glu Thr Gly Ala Thr  Ala Val Asn
        995                 1000                1005

Ala Gly  Asn Ala Glu Thr Val  Thr Ser Gly Thr  Ser  Val Asn Phe
    1010                1015                1020

Lys Asn  Gly Asn Ala Thr Thr  Ala Thr Val Ser  Lys  Asp Asn Gly
    1025                1030                1035

Asn Ile  Asn Val Lys Tyr  Asp Val Asn Val Gly  Asp  Gly Leu Lys
    1040                1045                1050

Ile Gly  Asp Asp Lys Lys Ile  Val Ala Asp Thr  Thr  Thr Leu Thr
    1055                1060                1065

Val Thr  Gly Gly Lys Val Ser  Val Pro Ala Gly  Ala  Asn Ser Val
    1070                1075                1080

Asn Asn  Asn Lys Lys Leu Val  Asn Ala Glu Gly  Leu  Ala Thr Ala
    1085                1090                1095

Leu Asn  Asn Leu Ser Trp Thr  Ala Lys Ala Asp  Lys  Tyr Ala Asp
    1100                1105                1110

Gly Glu  Ser Glu Gly Glu Thr  Asp Gln Glu Val  Lys  Ala Gly Asp
    1115                1120                1125

Lys Val  Thr Phe Lys Ala Gly  Lys Asn Leu Lys  Val  Lys Gln Ser
    1130                1135                1140

Glu Lys  Asp Phe Thr Tyr Ser  Leu Gln Asp Thr  Leu  Thr Gly Leu
    1145                1150                1155

Thr Ser  Ile Thr Leu Gly Gly  Thr Ala Asn Gly  Arg  Asn Asp Thr
    1160                1165                1170

Gly Thr  Val Ile Asn Lys Asp  Gly Leu Thr Ile  Thr  Leu Ala Asn
    1175                1180                1185

Gly Ala  Ala Ala Gly Thr Asp  Ala Ser Asn Gly  Asn  Thr Ile Ser
    1190                1195                1200

Val Thr  Lys Asp Gly Ile Ser  Ala Gly Asn Lys  Glu  Ile Thr Asn
    1205                1210                1215

Val Lys  Ser Ala Leu Lys Thr  Tyr Lys Asp Thr  Gln  Asn Thr Ala
    1220                1225                1230

Asp Glu  Thr Gln Asp Lys Glu  Phe His Ala Ala  Val  Lys Asn Ala
    1235                1240                1245

Asn Glu  Val Glu Phe Val Gly  Lys Asn Gly Ala  Thr  Val Ser Ala
    1250                1255                1260

Lys Thr  Asp Asn Asn Gly Lys  His Thr Val Thr  Ile  Asp Val Ala
    1265                1270                1275

Glu Ala  Lys Val Gly Asp Gly  Leu Glu Lys Asp  Thr  Asp Gly Lys
    1280                1285                1290

Ile Lys  Leu Lys Val Asp Asn  Thr Asp Gly Asn  Asn  Leu Leu Thr
    1295                1300                1305

Val Asp  Ala Thr Lys Gly Ala  Ser Val Ala Lys  Gly  Glu Phe Asn
    1310                1315                1320

Ala Val  Thr Thr Asp Ala Thr  Thr Ala Gln Gly  Thr  Asn Ala Asn
    1325                1330                1335

Glu Arg  Gly Lys Val Val Val  Lys Gly Ser Asn  Gly  Ala Thr Ala
    1340                1345                1350

Thr Glu  Thr Asp Lys Lys Lys  Val Ala Thr Val  Gly  Asp Val Ala
    1355                1360                1365

Lys Ala  Ile Asn Asp Ala Ala  Thr Phe Val Lys  Val  Glu Asn Asp
```

-continued

```
            1370                1375                1380

Asp Ser Ala Thr Ile Asp Ser Pro Thr Asp Gly Ala Asn
        1385                1390                1395

Asp Ala Leu Lys Ala Gly Asp Thr Leu Thr Leu Lys Ala Gly Lys
        1400                1405                1410

Asn Leu Lys Val Lys Arg Asp Gly Lys Asn Ile Thr Phe Ala Leu
        1415                1420                1425

Ala Asn Asp Leu Ser Val Lys Ser Ala Thr Val Ser Asp Lys Leu
        1430                1435                1440

Ser Leu Gly Thr Asn Gly Asn Lys Val Asn Ile Thr Ser Asp Thr
        1445                1450                1455

Lys Gly Leu Asn Phe Ala Lys Asp Ser Lys Thr Gly Asp Asp Ala
        1460                1465                1470

Asn Ile His Leu Asn Gly Ile Ala Ser Thr Leu Thr Asp Thr Leu
        1475                1480                1485

Leu Asn Ser Gly Ala Thr Thr Asn Leu Gly Gly Asn Gly Ile Thr
        1490                1495                1500

Asp Asn Glu Lys Lys Arg Ala Ala Ser Val Lys Asp Val Leu Asn
        1505                1510                1515

Ala Gly Trp Asn Val Arg Gly Val Lys Pro Ala Ser Ala Asn Asn
        1520                1525                1530

Gln Val Glu Asn Ile Asp Phe Val Ala Thr Tyr Asp Thr Val Asp
        1535                1540                1545

Phe Val Ser Gly Asp Lys Asp Thr Thr Ser Val Thr Val Glu Ser
        1550                1555                1560

Lys Asp Asn Gly Lys Arg Thr Glu Val Lys Ile Gly Ala Lys Thr
        1565                1570                1575

Ser Val Ile Lys Asp His Asn Gly Lys Leu Phe Thr Gly Lys Glu
        1580                1585                1590

Leu Lys Asp Ala Asn Asn Asn Gly Val Thr Val Thr Glu Thr Asp
        1595                1600                1605

Gly Lys Asp Glu Gly Asn Gly Leu Val Thr Ala Lys Ala Val Ile
        1610                1615                1620

Asp Ala Val Asn Lys Ala Gly Trp Arg Val Lys Thr Thr Gly Ala
        1625                1630                1635

Asn Gly Gln Asn Asp Asp Phe Ala Thr Val Ala Ser Gly Thr Asn
        1640                1645                1650

Val Thr Phe Ala Asp Gly Asn Gly Thr Thr Ala Glu Val Thr Lys
        1655                1660                1665

Ala Asn Asp Gly Ser Ile Thr Val Lys Tyr Asn Val Lys Val Ala
        1670                1675                1680

Asp Gly Leu Lys Leu Asp Gly Asp Lys Ile Val Ala Asp Thr Thr
        1685                1690                1695

Val Leu Thr Val Ala Asp Gly Lys Val Thr Ala Pro Asn Asn Gly
        1700                1705                1710

Asp Gly Lys Lys Phe Val Asp Ala Ser Gly Leu Ala Asp Ala Leu
        1715                1720                1725

Asn Lys Leu Ser Trp Thr Ala Thr Ala Gly Lys Glu Gly Thr Gly
        1730                1735                1740

Glu Val Asp Pro Ala Asn Ser Ala Gly Gln Glu Val Lys Ala Gly
        1745                1750                1755

Asp Lys Val Thr Phe Lys Ala Gly Asp Asn Leu Lys Ile Lys Gln
        1760                1765                1770
```

```
Ser Gly Lys Asp Phe Thr Tyr Ser Leu Lys Lys Glu Leu Lys Asp
1775                1780                1785

Leu Thr Ser Val Glu Phe Lys Asp Ala Asn Gly Gly Thr Gly Ser
1790                1795                1800

Glu Ser Thr Lys Ile Thr Lys Asp Gly Leu Thr Ile Thr Pro Ala
1805                1810                1815

Asn Gly Ala Gly Ala Ala Gly Ala Asn Thr Ala Asn Thr Ile Ser
1820                1825                1830

Val Thr Lys Asp Gly Ile Ser Ala Gly Asn Lys Ala Val Thr Asn
1835                1840                1845

Val Val Ser Gly Leu Lys Lys Phe Gly Asp Gly His Thr Leu Ala
1850                1855                1860

Asn Gly Thr Val Ala Asp Phe Glu Lys His Tyr Asp Asn Ala Tyr
1865                1870                1875

Lys Asp Leu Thr Asn Leu Asp Glu Lys Gly Ala Asp Asn Asn Pro
1880                1885                1890

Thr Val Ala Asp Asn Thr Ala Ala Thr Val Gly Asp Leu Arg Gly
1895                1900                1905

Leu Gly Trp Val Ile Ser Ala Asp Lys Thr Thr Gly Glu Pro Asn
1910                1915                1920

Gln Glu Tyr Asn Ala Gln Val Arg Asn Ala Asn Glu Val Lys Phe
1925                1930                1935

Lys Ser Gly Asn Gly Ile Asn Val Ser Gly Lys Thr Leu Asn Gly
1940                1945                1950

Thr Arg Val Ile Thr Phe Glu Leu Ala Lys Gly Glu Val Val Lys
1955                1960                1965

Ser Asn Glu Phe Thr Val Lys Asn Ala Asp Gly Ser Glu Thr Asn
1970                1975                1980

Leu Val Lys Val Gly Asp Met Tyr Tyr Ser Lys Glu Asp Ile Asp
1985                1990                1995

Pro Ala Thr Ser Lys Pro Met Thr Gly Lys Thr Glu Lys Tyr Lys
2000                2005                2010

Val Glu Asn Gly Lys Val Val Ser Ala Asn Gly Ser Lys Thr Glu
2015                2020                2025

Val Thr Leu Thr Asn Lys Gly Ser Gly Tyr Val Thr Gly Asn Gln
2030                2035                2040

Val Ala Asp Ala Ile Ala Lys Ser Gly Phe Glu Leu Gly Leu Ala
2045                2050                2055

Asp Ala Ala Glu Ala Glu Lys Ala Phe Ala Glu Ser Ala Lys Asp
2060                2065                2070

Lys Gln Leu Ser Lys Asp Lys Ala Glu Thr Val Asn Ala His Asp
2075                2080                2085

Lys Val Arg Phe Ala Asn Gly Leu Asn Thr Lys Val Ser Ala Ala
2090                2095                2100

Thr Val Glu Ser Thr Asp Ala Asn Gly Asp Lys Val Thr Thr Thr
2105                2110                2115

Phe Val Lys Thr Asp Val Glu Leu Pro Leu Thr Gln Ile Tyr Asn
2120                2125                2130

Thr Asp Ala Asn Gly Asn Lys Ile Val Lys Lys Ala Asp Gly Lys
2135                2140                2145

Trp Tyr Glu Leu Asn Ala Asp Gly Thr Ala Ser Asn Lys Glu Val
2150                2155                2160

Thr Leu Gly Asn Val Asp Ala Asn Gly Lys Lys Val Val Lys Val
2165                2170                2175
```

```
Thr Glu Asn Gly Ala Asp Lys Trp Tyr Tyr Thr Asn Ala Asp Gly
    2180            2185                2190

Ala Ala Asp Lys Thr Lys Gly Glu Val Ser Asn Asp Lys Val Ser
    2195            2200                2205

Thr Asp Glu Lys His Val Val Arg Leu Asp Pro Asn Asn Gln Ser
    2210            2215                2220

Asn Gly Lys Gly Val Val Ile Asp Asn Val Ala Asn Gly Glu Ile
    2225            2230                2235

Ser Ala Thr Ser Thr Asp Ala Ile Asn Gly Ser Gln Leu Tyr Ala
    2240            2245                2250

Val Ala Lys Gly Val Thr Asn Leu Ala Gly Gln Val Asn Asn Leu
    2255            2260                2265

Glu Gly Lys Val Asn Lys Val Gly Lys Arg Ala Asp Ala Gly Thr
    2270            2275                2280

Ala Ser Ala Leu Ala Ala Ser Gln Leu Pro Gln Ala Thr Met Pro
    2285            2290                2295

Gly Lys Ser Met Val Ala Ile Ala Gly Ser Ser Tyr Gln Gly Gln
    2300            2305                2310

Asn Gly Leu Ala Ile Gly Val Ser Arg Ile Ser Asp Asn Gly Lys
    2315            2320                2325

Val Ile Ile Arg Leu Ser Gly Thr Thr Asn Ser Gln Gly Lys Thr
    2330            2335                2340

Gly Val Ala Ala Gly Val Gly Tyr Gln Trp
    2345            2350

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 34

His His His His His His
1               5
```